(12) United States Patent
Lay et al.

(10) Patent No.: US 11,975,215 B2
(45) Date of Patent: May 7, 2024

(54) DEVICES AND RELATED METHODS FOR PHOTOTHERAPEUTIC TREATMENT OF SKIN

(71) Applicant: KNOW Bio, LLC, Durham, NC (US)

(72) Inventors: James Michael Lay, Apex, NC (US); Nicholas William Medendorp, Jr., Durham, NC (US)

(73) Assignee: KNOW Bio, LLC, Morrisville, NC (US)

( * ) Notice: Subject to any disclaimer, the term of this patent is extended or adjusted under 35 U.S.C. 154(b) by 313 days.

(21) Appl. No.: 17/325,618

(22) Filed: May 20, 2021

(65) Prior Publication Data

US 2021/0370090 A1  Dec. 2, 2021

Related U.S. Application Data

(60) Provisional application No. 63/030,058, filed on May 26, 2020.

(51) Int. Cl.
*A61N 5/06* (2006.01)

(52) U.S. Cl.
CPC ........... *A61N 5/0616* (2013.01); *A61N 5/062* (2013.01); *A61N 2005/0632* (2013.01); *A61N 2005/0647* (2013.01)

(58) Field of Classification Search
CPC .................. A61N 5/0616; A61N 5/062; A61N 2005/0632; A61N 2005/0647; A61N 2005/0652
See application file for complete search history.

(56) References Cited

U.S. PATENT DOCUMENTS

| 2,333,987 A | 11/1943 | Dandy |
| 5,228,431 A | 7/1993 | Giarretto |

(Continued)

FOREIGN PATENT DOCUMENTS

| AU | 2016100390 A4 | 7/2016 |
| CN | 101687101 A | 3/2010 |

(Continued)

OTHER PUBLICATIONS

Notice of Allowance for U.S. Appl. No. 16/884,858, dated Mar. 9, 2022, 7 pages.

(Continued)

*Primary Examiner* — Nathan J Jenness
(74) *Attorney, Agent, or Firm* — Withrow & Terranova, P.L.L.C.

(57) ABSTRACT

Systems, devices, and related methods for phototherapeutic treatment of skin, and more particularly phototherapeutic treatments for skin conditioning and/or the treatment of skin wrinkles are disclosed. Certain aspects relate to impinging light having a first peak wavelength on skin tissue at a first radiant flux, a second peak wavelength on the skin tissue at a second radiant flux, and, optionally, a third peak wavelength on skin tissue at a third radiant flux. The first wavelength may be selected to produce nitric oxide in the skin and/or to release endogenous stores of nitric oxide; the second wavelength may be selected to promote collagen production. Certain methods involve impinging light having a third peak wavelength that may be selected to reduce inflammation. Devices are disclosed that include combinations of housings, light-transmissive elements, and flexible substrates that are configured to deliver such light to one or more targeted areas.

15 Claims, 36 Drawing Sheets

(56) References Cited

U.S. PATENT DOCUMENTS

| | | |
|---|---|---|
| 5,549,639 A | 8/1996 | Ross |
| 5,616,140 A | 4/1997 | Prescott |
| 5,913,883 A * | 6/1999 | Alexander ........... A61N 5/0616 |
| | | D24/231 |
| 6,096,066 A | 8/2000 | Chen et al. |
| 6,171,332 B1 | 1/2001 | Whitehurst |
| 6,283,956 B1 | 9/2001 | McDaniel |
| 6,290,713 B1 | 9/2001 | Russell |
| 6,443,978 B1 | 9/2002 | Zharov |
| 6,497,719 B2 | 12/2002 | Pearl et al. |
| 6,645,230 B2 | 11/2003 | Whitehurst |
| 6,663,659 B2 | 12/2003 | McDaniel |
| 6,676,655 B2 | 1/2004 | McDaniel |
| 6,887,260 B1 | 5/2005 | McDaniel |
| 6,918,922 B2 | 7/2005 | Oron |
| 6,936,044 B2 | 8/2005 | McDaniel |
| 6,955,684 B2 | 10/2005 | Savage, Jr. et al. |
| 6,989,023 B2 | 1/2006 | Black |
| 7,201,764 B2 | 4/2007 | Pearl et al. |
| 7,201,765 B2 | 4/2007 | McDaniel |
| 7,267,673 B2 | 9/2007 | Pilcher et al. |
| 7,303,578 B2 | 12/2007 | De Taboada et al. |
| 7,304,201 B2 | 12/2007 | Holloway et al. |
| 7,309,348 B2 | 12/2007 | Streeter et al. |
| 7,494,503 B2 | 2/2009 | McDaniel |
| D599,954 S | 9/2009 | Michaels et al. |
| D631,604 S | 1/2011 | Michaels et al. |
| D635,686 S | 4/2011 | Tucker et al. |
| D639,751 S | 6/2011 | Tucker et al. |
| D640,793 S | 6/2011 | Britt |
| 8,053,977 B2 | 11/2011 | Lifka et al. |
| 8,146,607 B2 | 4/2012 | Rabin et al. |
| 8,192,473 B2 | 6/2012 | Tucker et al. |
| 8,252,033 B2 | 8/2012 | Tucker et al. |
| 8,518,029 B2 | 8/2013 | Birmingham et al. |
| 8,556,951 B2 | 10/2013 | Witt et al. |
| 8,641,702 B2 | 2/2014 | Pilcher et al. |
| 8,651,111 B2 | 2/2014 | McDaniel |
| 8,747,446 B2 | 6/2014 | Chen et al. |
| 8,758,215 B2 | 6/2014 | Legendre et al. |
| 8,771,327 B2 | 7/2014 | Pearl et al. |
| 8,807,131 B1 | 8/2014 | Tunnell et al. |
| D712,561 S | 9/2014 | Hagenauer |
| 8,845,704 B2 | 9/2014 | Dunning et al. |
| D716,493 S | 10/2014 | Michaels et al. |
| 8,900,282 B2 | 12/2014 | Brawn |
| 8,900,283 B2 | 12/2014 | Johnson et al. |
| 9,017,391 B2 | 4/2015 | McDaniel |
| 9,040,103 B2 | 5/2015 | Marrot et al. |
| 9,132,279 B2 | 9/2015 | Roersma et al. |
| 9,144,690 B2 | 9/2015 | McDaniel |
| 9,192,780 B2 | 11/2015 | McDaniel |
| 9,215,921 B2 | 12/2015 | Thiebaut et al. |
| 9,227,082 B2 | 1/2016 | McDaniel |
| D754,897 S | 4/2016 | Michaels et al. |
| 9,308,389 B2 | 4/2016 | Brawn |
| 9,415,237 B2 | 8/2016 | Wagenaar Cacciola et al. |
| D777,339 S | 1/2017 | Chen |
| 9,545,524 B2 | 1/2017 | Maas et al. |
| 9,554,963 B2 | 1/2017 | Pilcher et al. |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,724,536 B1 | 8/2017 | Rabin et al. |
| D804,047 S | 11/2017 | Michaels et al. |
| 10,525,275 B2 | 1/2020 | Stasko et al. |
| 2002/0128648 A1 | 9/2002 | Weber et al. |
| 2003/0076281 A1 | 4/2003 | Morgan et al. |
| 2003/0130709 A1 | 7/2003 | D.C. et al. |
| 2003/0167080 A1 | 9/2003 | Hart et al. |
| 2003/0236487 A1 | 12/2003 | Knowlton |
| 2004/0044384 A1 | 3/2004 | Leber et al. |
| 2004/0073079 A1 | 4/2004 | Altshuler et al. |
| 2004/0162549 A1 | 8/2004 | Altshuler |
| 2004/0162596 A1 | 8/2004 | Altshuler et al. |
| 2005/0045189 A1 | 3/2005 | Jay |
| 2005/0070977 A1 * | 3/2005 | Molina ............... A61N 2/02 |
| | | 607/88 |
| 2005/0143792 A1 | 6/2005 | Jay |
| 2006/0227844 A1 | 10/2006 | Guenter |
| 2006/0258896 A1 | 11/2006 | Haber et al. |
| 2006/0287696 A1 | 12/2006 | Wright et al. |
| 2007/0060819 A1 | 3/2007 | Altshuler et al. |
| 2007/0073366 A1 | 3/2007 | Porco |
| 2007/0106856 A1 | 5/2007 | Nomura et al. |
| 2007/0179571 A1 | 8/2007 | De Taboada et al. |
| 2007/0185553 A1 | 8/2007 | Kennedy |
| 2007/0208395 A1 | 9/2007 | Leclerc et al. |
| 2007/0208396 A1 | 9/2007 | Whatcott et al. |
| 2007/0213792 A1 | 9/2007 | Yaroslavsky et al. |
| 2007/0233208 A1 | 10/2007 | Kurtz et al. |
| 2007/0248930 A1 | 10/2007 | Brawn |
| 2008/0033516 A1 | 2/2008 | Altshuler et al. |
| 2008/0269849 A1 | 10/2008 | Lewis |
| 2008/0319430 A1 | 12/2008 | Zenzie et al. |
| 2009/0177256 A1 | 7/2009 | Ripper et al. |
| 2009/0254156 A1 | 10/2009 | Powell et al. |
| 2009/0318802 A1 | 12/2009 | Boyden et al. |
| 2009/0319008 A1 | 12/2009 | Mayer |
| 2010/0004645 A1 | 1/2010 | Jeong et al. |
| 2010/0049180 A1 | 2/2010 | Wells et al. |
| 2010/0076529 A1 | 3/2010 | Tucker et al. |
| 2010/0106077 A1 | 4/2010 | Rabin et al. |
| 2010/0204762 A1 | 8/2010 | De Taboada et al. |
| 2010/0242155 A1 | 9/2010 | Carullo, Jr. |
| 2010/0289506 A1 | 11/2010 | Moon |
| 2010/0331928 A1 | 12/2010 | Dunning et al. |
| 2011/0015707 A1 | 1/2011 | Tucker et al. |
| 2011/0054573 A1 | 3/2011 | Mitchell |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0264174 A1 | 10/2011 | McNeill et al. |
| 2011/0301673 A1 | 12/2011 | Hoffer et al. |
| 2012/0059440 A1 | 3/2012 | Hamid |
| 2012/0065709 A1 | 3/2012 | Dunning et al. |
| 2013/0041432 A1 | 2/2013 | Tucker et al. |
| 2013/0066404 A1 * | 3/2013 | Tapper ............... A61F 9/045 |
| | | 607/90 |
| 2013/0090873 A1 | 4/2013 | Lundstrum et al. |
| 2013/0131762 A1 | 5/2013 | Oversluizen et al. |
| 2013/0144364 A1 | 6/2013 | Wagenaar Cacciola et al. |
| 2014/0074193 A1 | 3/2014 | Luzon et al. |
| 2014/0128941 A1 | 5/2014 | Williams |
| 2014/0128942 A1 | 5/2014 | Bembridge et al. |
| 2014/0148879 A1 | 5/2014 | Mersch |
| 2014/0243933 A1 | 8/2014 | Ginggen |
| 2014/0276248 A1 | 9/2014 | Hall et al. |
| 2014/0303693 A1 | 10/2014 | Haarlander et al. |
| 2014/0350643 A1 | 11/2014 | Pepitone et al. |
| 2015/0005854 A1 | 1/2015 | Said |
| 2015/0013214 A1 | 1/2015 | Isserow et al. |
| 2015/0112411 A1 | 4/2015 | Beckman et al. |
| 2015/0127072 A1 * | 5/2015 | Pomar ............... A61N 5/0616 |
| | | 607/90 |
| 2015/0134033 A1 | 5/2015 | Tapper et al. |
| 2015/0297914 A1 | 10/2015 | Hamid et al. |
| 2016/0051835 A1 | 2/2016 | Tapper et al. |
| 2016/0106999 A1 | 4/2016 | Michaels et al. |
| 2016/0271420 A1 | 9/2016 | Pina |
| 2016/0310757 A1 * | 10/2016 | Pepitone ............ A61N 5/0617 |
| 2017/0028216 A1 * | 2/2017 | Medendorp, Jr. .... A61N 5/0616 |
| 2019/0262567 A1 * | 8/2019 | Davis ............... A61B 5/4818 |
| 2022/0152417 A1 * | 5/2022 | Kim ................. A61N 5/0616 |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 203169848 U | 9/2013 |
| CN | 103930162 A | 7/2014 |
| CN | 204317834 U | 5/2015 |
| EP | 2508229 A1 | 10/2012 |

(56) References Cited

FOREIGN PATENT DOCUMENTS

| | | | | |
|---|---|---|---|---|
| EP | 3069762 A1 | 9/2016 | | |
| KR | 101823123 B1 | * 1/2018 | ............... | A61N 5/06 |
| KR | 20190018383 A | * 2/2019 | ........... | A61N 5/0616 |
| WO | 2004033040 A1 | 4/2004 | | |
| WO | 2008131343 A1 | 10/2008 | | |
| WO | 2008144157 A1 | 11/2008 | | |
| WO | 2013036558 A1 | 3/2013 | | |
| WO | 2014146029 A1 | 9/2014 | | |
| WO | 2015006309 A1 | 1/2015 | | |
| WO | WO 2020/040435 A1 | * 2/2020 | ............... | A61N 5/06 |

OTHER PUBLICATIONS

Non-Final Office Action for U.S. Appl. No. 16/884,858, dated Sep. 1, 2021, 14 pages.
Non-Final Office Action for U.S. Appl. No. 17/750,872, dated Nov. 8, 2022, 15 pages.
Office Action for Chinese Patent Application No. 201680054311.3, dated Dec. 20, 2021, 27 pages.
Notification to Grant for Chinese Patent Application No. 201680054311.3, dated Jan. 14, 2022, 3 pages.
Final Office Action for U.S. Appl. No. 16/884,858, dated Dec. 21, 2021, 16 pages.
Notice of Allowance for Brazilian Patent Application No. BR112018001857-0, dated Sep. 6, 2022, 6 pages.
Abeyakirthi, Sharnika, "Nitric oxide," DermNet NZ, 2009,4 pages, http://www.dermnetnz.org/topics/nitric oxide/.
Adamskaya, Natalia et al., "Light therapy by blue LED improves wound healing in an excision model in rats," Injury, 2010, 5 pages.
Andrew, Penelope J. et al., "Enzymatic function of nitric oxide synthases," Cardiovascular Research, vol. 43, No. 3, Aug. 15, 1999, pp. 521-531.
Author Unknown, "Brilliant Light Therapy," In Light Wellness Systems, eBrochure, Date Unknown, 5 pages.
Author Unknown, "Healed by Light," Digi-Key Electronics, Jul. 1, 2014, 4 pages, www.digikey.com/es/rticles/techzone/2014/jul/healed-by-light.
Author Unknown, "illuMask," La Lumiere, Date Unknown, 2 pages, http://www.illumask.com/dimming/.
Author Unknown, "IPL Hair Removal," Spectrum Science & Beauty, Spectrum Blog, Sep. 16, 2014, 3 Pages, http://www.spectrumsciencebeauty.com.au/ipl-hair-removal/#prettyPhoto.
Author Unknown, "Near-IR Photoluminescent Dyes for Molecular Labeling," NanoQuantum, Technology, 2013, 7 pages, http://www.nanoquantum.com/Technology.html.
Author Unknown, "Theradome Laser Helmet Review—A 120 Day Continuous Journal," Prevent Hair Loss Products, Jan. 14, 2014, retrieved Jun. 27, 2017, https://web.archive.org/web/20140610024017/http://preventhairlossproducts.com:80/theradome-laser-helmet-review-120-day-continuous-journal/, pp. 1-4.
Author Unknown, "Ultraviolet Light Therapy," Wound Care Centers, Date Unknown, 3 pages, http://www.woundcarecenters.org/article/wound-therapies/ultraviolet-light-therapy.
Author Unknown, "What is Light Therapy used for?" Rio, The Dezac Group, Ltd, Date Unknown, 4 pages, http://www.lightmask.com/uses_for_It.htm#top.
Avci, Pinar et al., "Low-Level Laser {Light) Therapy {LLL T) for Treatment of Hair Loss," Lasers in Surgery and Medicine, vol. 46, 2014, pp. 144-151.
Avci, Pinar et al., "Low-Level Laser {Light) Therapy {LLL T) in Skin: Stimulating, Healing, Restoring," Seminars in Cutaneous Medicine and Surgery, vol. 32, No. 1, 2013, pp. 41-52.
Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.
Barolet, Daniel, "Light-Emitting Diodes (LEOs) in Dermatology," Seminars in Cutaneous Medicine and Surgery, vol. 27, No. 4, Dec. 1, 2008, pp. 227-238.
Cals-Grierson, M.-M. et al., "Nitric oxide function in the skin," Nitric Oxide, vol. 10, No. 4, Jun. 2004, pp. 179-193.
Chaves, Maria Emilia De Abreu et al., "Effects of low-power light therapy on wound healing: LASER x LED," Anais Brasileiros de Dermatologia, vol. 89, No. 4, Jul./Aug. 2014, pp. 616-623.
Farivar, Shirin et al., "Biological Effects of Low Level Laser Therapy," Journal of Lasers in Medical Sciences, vol. 5, No. 2, Spring 2014, pp. 58-62.
Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.
Gupta, Asheesh et al., "History and Fundamentals of Low-Level Laser {Light) Therapy," Handbook of Dhotomedicine, Chapter 5, CRC Press, 2014, pp. 43-52.
Hamblin, Michael, et al., "Mechanisms of Low Level Light Therapy," Proceedings of the SPIE, vol. 6140, Feb. 10, 2006, pp. 614001-1 to 641001-12.
Hamblin, Michael R, "Mechanisms of Low Level Light Therapy," Aug. 14, 2008, 22 pages, http://photobiology_info/Hamblin.html.
Hamblin, Michael R, The Role of Nitric Oxide in Low Level Light Therapy, Proceedings of SPIE, vol. 6846, 2008, p. 684602-1 to 684602-14.
Karu, Tiina I., "Low-Power Laser Therapy," Biomedical Photonics Handbook, Chapter 48, CRC Press, 2003, pp. 48-1 to 48-25.
Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.
Kovacs, Izabella et al., "Nitric oxide-based protein modification: formation and site-specificity of protein~itrosylation," Frontiers in Plant Science, vol. 4, Article 137, May 14, 2013, 10 pages.
Leong, Mimi, "Effects of Light-Emitiing Diode Photostimulation on Burn Wound Healing," hesis, The University of Texas Graduate School of Biomedical Sciences at Galveston, May 2006, 92 pages.
Mandel, Arkady, et al., "A renaissance in low-level laser {light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Phurrough, Steve et al., "Decision Memo for Infrared Therapy Devices {CAG-00291 N)," Centers for Medicare & Medicaid Services, Oct. 24, 2006, 37 pages.
Poyton, Roberto et al., "Therapeutic Photobiomodulation: Nitric Oxide and a Novel Function of Mitochondrial:;ytochrome C Oxidase," Discovery Medicine, Feb. 20, 2011, 11 pages.
Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.
Non-Final Office Action for U.S. Appl. No. 15/222,292, dated Aug. 6, 2019, 13 pages.
Notice of Allowance and Examiner-Initiated Interview Summary for U.S. Appl. No. 15/222,292, dated Feb. 25, 2020, 9 pages.
Extended European Search Report for European Patent Application No. 20194978.1, dated Jun. 2, 2021, 14 pages.
International Search Report and Written Opinion for PCT/US2016/44403, dated Dec. 16, 2016, 11 pages.
Final Office Action for U.S. Appl. No. 17/750,872, dated May 10, 2023, 16 pages.
Advisory Action for U.S. Appl. No. 17/750,872, dated Aug. 17, 2023, 3 pages.
Non-Final Office Action for U.S. Appl. No. 18/315,795, mailed Dec. 20, 2023, 17 pages.
Non-Final Office Action for U.S. Appl. No. 18/315,819, mailed Dec. 21, 2023, 16 pages.
International Search Report and Written Opinion for International Patent Application No. PCT/US2023/072693, mailed Nov. 21, 2023, 12 pages.

(56) References Cited

OTHER PUBLICATIONS

Non-Final Office Action for U.S. Appl. No. 17/750,872, mailed Nov. 8, 2023, 18 pages.

* cited by examiner

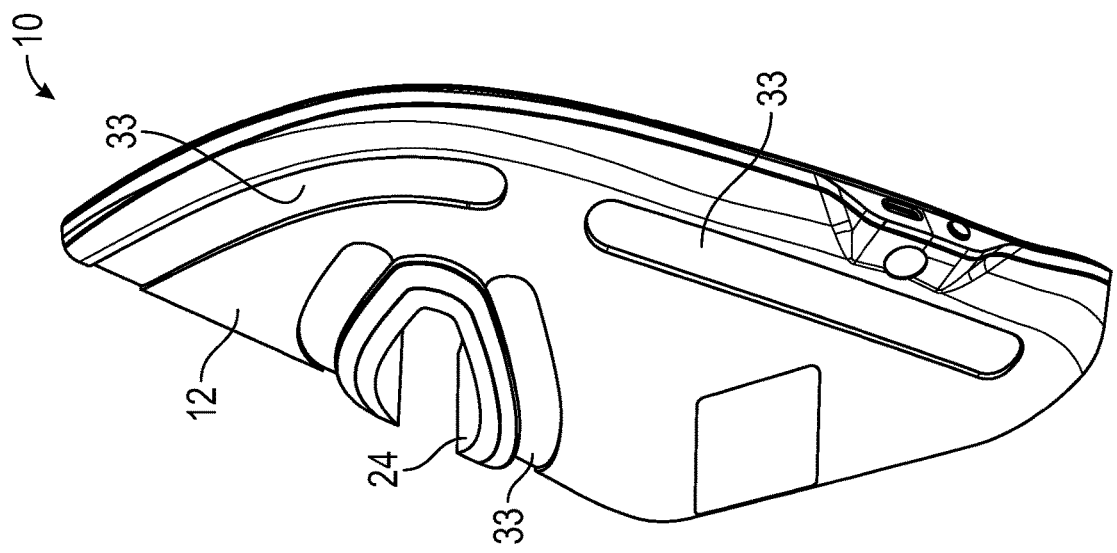
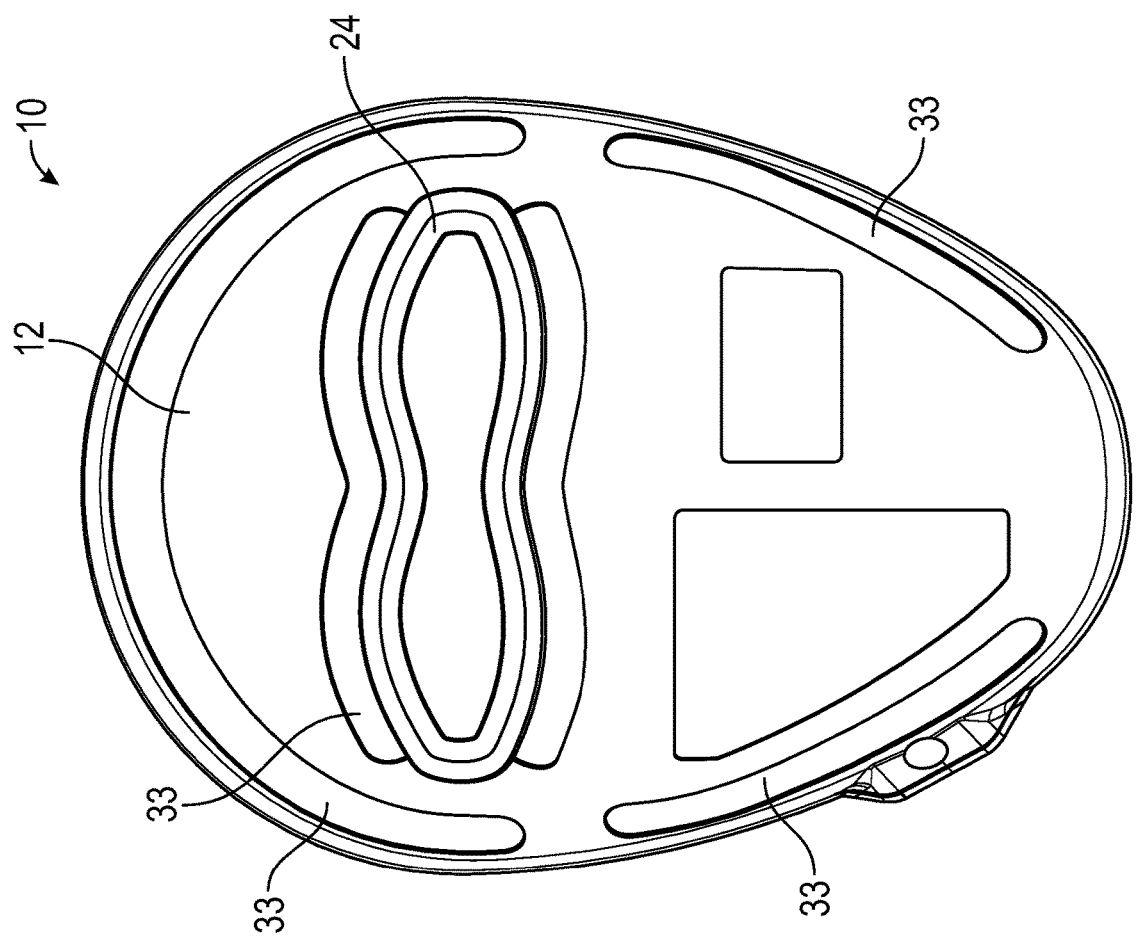

DEVICES AND RELATED METHODS FOR PHOTOTHERAPEUTIC TREATMENT OF SKIN

RELATED APPLICATIONS

This application claims the benefit of provisional patent application Ser. No. 63/030,058, filed May 26, 2020, the disclosure of which is hereby incorporated herein by reference in its entirety.

FIELD OF THE DISCLOSURE

The present disclosure relates to systems, devices, and related methods for phototherapeutic treatments of skin, and more particularly to phototherapeutic treatments of skin for skin conditioning and/or the treatment of skin wrinkles.

BACKGROUND

The term "phototherapy" relates to the therapeutic use of light. Various light therapies (e.g., including low-level light therapy (LLLT) and photodynamic therapy (PDT)) have been publicly reported or claimed to provide various health-related medical benefits. These benefits include reducing inflammation of the skin, conditioning and treating skin tissue, skin tissue rejuvenation, skin tissue wound healing, and reducing wrinkles and scars.

Several biological responses have been suggested by which phototherapy may provide therapeutic benefits such as: increasing circulation (e.g., through formation of new capillaries); stimulating production of collagen (referred to herein as collagen-promoting light, collagen-producing light, and collagen-stimulating light, i.e., light that causes collagen to be produced and/or that causes an increase in collagen production); stimulating the release of adenosine triphosphate (ATP); enhancing porphyrin production; reducing excitability of nervous system; stimulating fibroblast activity; increasing phagocytosis; inducing thermal effects; stimulating skin tissue granulation and connective skin tissue projections; reducing inflammation; and stimulating acetylcholine release.

Phototherapy has also been suggested as a way to stimulate cells to generate nitric oxide. Various biological functions attributed to nitric oxide include use of its role as a signaling messenger, a cytotoxin, an antiapoptotic agent, an antioxidant, and a regulator of microcirculation. Nitric oxide is known to relax vascular smooth muscles, dilate blood vessels, inhibit aggregation of platelets, and modulate T-cell-mediate immune response.

Nitric oxide is produced by multiple cell types in skin, and is formed by the conversion of the amino acid L-arginine to L-citrulline and nitric oxide, mediated by the enzymatic action of nitric oxide synthases (NOSs). NOS is a nicotinamide adenine dinucleotide phosphate hydrogen (NADPH)-dependent enzyme that catalyzes the following reaction:

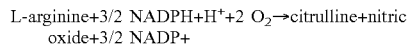

L-arginine+3/2 NADPH+H$^+$+2 O$_2$→citrulline+nitric oxide+3/2 NADP+

In mammals, three distinct genes encode NOS isozymes: neuronal (nNOS or NOS-I), cytokine-inducible (iNOS or NOS-II), and endothelial (eNOS or NOS-III). iNOS and nNOS are soluble and found predominantly in the cytosol, while eNOS is membrane associated. Many cells in mammals synthesize iNOS in response to inflammatory conditions.

Skin has been shown to upregulate inducible nitric oxide synthase expression and subsequent production of nitric oxide in response to electromagnetic irradiation stress. Nitric oxide serves a predominantly antioxidant role in the high levels generated in response to that radiation.

Nitric oxide is a free radical capable of diffusing across membranes and into various skin tissues; moreover, it is very reactive, with a half-life of only a few seconds. Due to its unstable nature, nitric oxide rapidly reacts with other molecules to form more stable products. For example, in the blood, nitric oxide rapidly oxidizes to nitrite, and is then further oxidized with oxyhaemoglobin to produce nitrate. Nitric oxide also reacts directly with oxyhaemoglobin to produce methaemoglobin and nitrate. Nitric oxide is also endogenously stored on a variety of nitrosated biochemical structures including nitrosoglutathione (GSNO), nitrosoalbumin, nitrosohemoglobin, and a large number of nitrosocysteine residues on other critical blood/skin tissue proteins. The term "nitroso" is defined as a nitrosated compound (RSNO or RNNO), via either S- or N-nitrosation. Metal nitrosyl (M-NO) complexes are another endogenous store of circulating nitric oxide, most commonly found as ferrous nitrosyl complexes in the body; however, metal nitrosyl complexes are not restricted to complexes with iron-containing metal centers. Nitric oxide-loaded chromophores including the enzyme cytochrome c oxidase (CCO-NO) represent additional endogenous stores of nitric oxide.

When nitric oxide is auto-oxidized into nitrosative intermediates, the nitric oxide is bound covalently in the body (in a "bound" state). Thus, conventional efforts to produce nitric oxide in skin tissue seems to have a limited therapeutic effect, since nitric oxide in its "gaseous" state is short-lived, and cells stimulated to produce nitric oxide may become depleted of NADPH or L-arginine to the point where they become unable to sustain nitric oxide production.

While light therapy associated with nitric oxide release may be useful in treating certain disorders, it would be advantageous to have additional therapeutic methods.

SUMMARY

Aspects of the present disclosure relate to systems, devices, and related methods for phototherapeutic treatments of skin, and more particularly to phototherapeutic treatments of skin for skin conditioning and/or the treatment of skin wrinkles. Certain aspects relate to phototherapeutic treatment of skin with light of at least two different wavelengths. Light having a first peak wavelength and a first radiant flux may be selected to stimulate enzymatic generation of nitric oxide to increase stores of endogenous nitric oxide or releases endogenous stores of nitric oxide. Light having a second peak wavelength and a second radiant flux may be selected to stimulate collagen production in the skin. Light having a third peak wavelength and a third radiant flux can also be used in conjunction with skin treatment for wrinkles, where the light at the third wavelength and third radiant flux provides an anti-inflammatory effect. Devices are disclosed that include combinations of housings, light-transmissive elements, and flexible substrates that are configured to deliver such light to one or more targeted areas.

Some embodiments of the present disclosure are methods that comprise impinging light having the first peak wavelength on the target skin tissue at a first radiant flux, and impinging light having the second peak wavelength on the target skin tissue at a second radiant flux. In some of such embodiments, a third peak wavelength impinges on the target skin tissue at a third radiant flux. In another aspect of such methods, the first and second wavelengths may impinge simultaneously, and in another aspect of this method, the first and second wavelengths may impinge sequentially.

In certain embodiments, the second peak wavelength may be greater than the first peak wavelength by 230 nanometers (nm), for example.

In certain embodiments, each of the first radiant flux and the second radiant flux may be in a range of from 1 milliwatt per square centimeter (mW/cm$^2$) to 60 mW/cm$^2$, e.g., an average of 4 mW/cm$^2$ to 5 mW/cm$^2$.

In certain embodiments, skin tissue is impinged with light of radiant exposure in the range of from about 0.3 joules per square centimeter (J/cm$^2$) to about 30 J/cm$^2$ (e.g., 4.5 mW/cm$^2$ for 10 minutes, or 1 mW/cm$^2$ for 45 minutes, or 0.1 mW/cm$^2$ for 450 minutes, etc.).

In another aspect, the disclosure relates to a device for conditioning skin to minimize wrinkle formation, and in particular, for increasing collagen production in the skin. The device includes means for impinging light having the first peak wavelength on skin tissue at a first radiant flux, and for impinging light having the second peak wavelength on skin tissue at a second radiant flux.

In certain embodiments, the device further includes driver circuitry configured to drive at least one first light-emitting device and at least one additional light-emitting device.

In some embodiments, the device includes at least one first solid state light-emitting device configured to impinge light having the first peak wavelength on skin tissue, and can further comprise at least one second solid state light-emitting device configured for light impingement having the second peak wavelength on skin tissue. The device additionally includes driver circuitry configured to drive at least one first solid state light-emitting device and at least one second solid state light-emitting device.

In certain embodiments of the device, each of the first radiant flux and the second radiant flux is in a range of from 1 mW/cm$^2$ to 60 mW/cm$^2$, e.g., an average of 4 mW/cm$^2$ to 5 mW/cm$^2$.

The first peak wavelength of light selected to be directed at the skin either promotes nitric oxide production or releases existing stores of nitric oxide within the skin. In one embodiment, the first peak wavelength may be in a range of from 610 nm to 630 nm. In some embodiments, at least 50 percent of light emitted from the first solid state light emitter(s) is of energy in a range of from about 1.97 electronvolts (eV) to about 2.03 eV. In some embodiments, at least 90 percent of light emitted from the first solid state light emitter(s) is of energy in a range of from about 1.97 eV to about 2.03 eV.

The second peak wavelength is selected to stimulate collagen production in the skin. The second peak wavelength may be between about 840 nm and about 860 nm, more specifically, between about 845 nm and about 855 nm, still more specifically, around 850 nm. In some embodiments, at least 50 percent of light emitted from the first solid state light emitter(s) is of energy in a range of from about 1.44 eV to about 1.48 eV. In some embodiments, at least 90 percent of light emitted from the first solid state light emitter(s) is of energy in a range of from about 1.44 eV to about 1.48 eV.

In some embodiments, a third wavelength can be directed at the skin to reduce inflammation. The third peak wavelength may be between about 640 nm and about 660 nm, specifically, between about 645 nm and about 655 nm, still more specifically, around 650 nm. In some embodiments, at least 50 percent of light emitted from the first solid state light emitter(s) is of energy in a range of from about 1.86 eV to about 1.94 eV. In some embodiments, at least 90 percent of light emitted from the first solid state light emitter(s) is of energy in a range of from about 1.86 eV to about 1.94 eV.

In one aspect of this embodiment, the first peak wavelength is in a range of from 615 nm to 625 nm and the second peak wavelength is in a range of from 845 nm to 855 nm.

In some aspects of the present disclosure, there are provided devices for treating living skin tissue, each of such devices comprising: a substrate; and at least first and second groups of light emitters.

In other aspects of the present disclosure, there are provided face-engaging devices, each of such devices comprising: a substrate; one or more eyepieces; and a headband.

In one aspect of the present disclosure, there is provided a device for treating living skin tissue, the device comprising: a substrate; at least first and second groups of light emitters; a circuit board; and a light-transmissive element, each of the first group of light emitters configured to emit light of wavelength in a range of from about 610 nm to about 630 nm, each of the second group of light emitters configured to emit light of wavelength in a range of from about 840 nm to about 860 nm, the circuit board comprising electrically-conductive regions and non-electrically-conductive regions, the circuit board in or on the substrate, the light-transmissive element on the circuit board, the circuit board configured to deliver electrical current to the first group of light emitters and to the second group of light emitters.

In another aspect of the present disclosure, there is provided a device for treating living skin tissue, the device comprising: a substrate; at least a first eyepiece; at least first and second groups of light emitters; a circuit board; and a light-transmissive element, the circuit board comprising electrically-conductive regions and non-electrically-conductive regions, the circuit board in or on the substrate, the light-transmissive element on the circuit board, the circuit board configured to deliver electrical current to the first group of light emitters and to the second group of light emitters, the first eyepiece engaged by the substrate, the device configured to conform to at least a portion of a human face, the substrate comprising at least a first eye opening, the first eyepiece in contact with portions of the substrate that extend around the first eye opening.

In another aspect of the present disclosure, there is provided a face-engaging device, the device comprising: a substrate; one or more eyepieces; a headband; and at least first and second headband engagement features, the one or more eyepieces engaged by the substrate, the substrate comprising one or more eye openings, the one or more eyepieces in contact with portions of the substrate that extend around the one or more eye opening, a first region of the headband engaged with the first headband engagement feature, a second region of the headband engaged with the second headband engagement feature, the device configured to be engaged with a human user, with a first surface of the device conforming to the human user's face, with the headband extending around the human user's head and exerting force that pushes the device toward the human user's face, and with at least 80 percent of said force being applied against a combination of (1) the human user's forehead and (2) areas of the human user's face that the one or more eyepieces contact.

In another aspect of the present disclosure, there is provided a face-engaging device, the device comprising: a substrate; a headband; and at least first and second headband engagement features, a first region of the headband engaged with the first headband engagement feature, a second region of the headband engaged with the second headband engagement feature, the device configured to be engaged with a human user, with a first surface of the device conforming to the human user's face, and with: a first imaginary line that bisects the headband along a portion of the headband extending away from the first headband engagement feature, and an imaginary line that bisects a region of the device that conforms to a forehead of the human user with whom the device is engaged, and that extends vertically, with the human user's head oriented upright and (a) intersecting at a location that is below the human user's forehead, with the human user's head oriented upright, and (b) forming an angle in a range of from about 50 degrees to about 70 degrees.

In another aspect of the present disclosure, there is provided a method of treating living skin tissue, comprising: positioning a device as described herein within 5 centimeters (cm) of a body, and supplying electricity to a circuit board of the device to cause light emitters of the device to emit light.

In another aspect of the present disclosure, there is provided a method of treating living skin tissue, comprising: positioning a device as described herein within 5 cm of a user's body, and positioning a strap of the device around a portion of the user's body.

In another aspect of the present disclosure, there is provided a method, comprising: positioning a device as described herein such that a portion of the device is in contact with a human user's forehead and a portion of one or more eyepieces of the device, and positioning a headband of the device around a portion of the user's head.

In another aspect, any of the foregoing aspects, and/or various separate aspects and features as described herein, may be combined for additional advantage. Any of the various features and elements as disclosed herein may be combined with one or more other disclosed features and elements unless indicated herein otherwise.

In an embodiment, a substrate may be used to apply the first peak wavelength and the second peak wavelength to skin.

In another embodiment, a substrate may be shaped to apply a first peak wavelength and a second peak wavelength to the skin of the face.

In another embodiment, a flexible substrate may be conformable to skin for applying a first peak wavelength and a second peak wavelength to the skin.

In certain aspects, a method of treating skin comprises: impinging light having a first peak wavelength on skin tissue, wherein the first peak wavelength is selected to at least one of stimulate nitric oxide production in skin and release endogenous stores of nitric oxide, and impinging light having a second peak wavelength on skin tissue, wherein the second peak wavelength is selected to stimulate collagen production. In certain embodiments, the first peak wavelength is in a range of from 610 nm to 630 nm. In certain embodiments, the second peak wavelength is in a range from 840 nm to 860 nm. In certain embodiments, the first peak wavelength is provided with a first radiant flux that is at least 1 mW/cm$^2$. In certain embodiments, the first radiant flux is not more than 60 mW/cm$^2$. In certain embodiments, the impinging of the light having the first peak wavelength is performed during a first time window, the impinging of the light having the second peak wavelength is performed during a second time window, and the second time window overlaps with the first time window. In certain embodiments, the impinging of the light having the first peak wavelength is performed during a first time window, the impinging of light having the second peak wavelength is performed during a second time window, and the second time window is non-overlapping with the first time window. In certain embodiments, the impinging of the light having the first peak wavelength on the skin tissue includes impinging more than one discrete pulse of the light having the first peak wavelength on the skin tissue during a first time window; and the impinging of the light having the second peak wavelength on the skin tissue includes impinging more than one discrete pulse of the light having the second peak wavelength on the skin tissue during a second time window. In certain embodiments, the method further comprises impinging light having a third peak wavelength on the skin tissue, wherein the third peak wavelength is selected to provide an anti-inflammatory effect to the skin tissue. In certain embodiments, the third peak wavelength is in a range from 640 nm to 660 nm.

In another aspect, a device for treating living skin tissue comprises: a housing; a light-transmissive element; a flexible printed circuit board that is arranged between the housing and the light-transmissive element; and a plurality of first light-emitting diodes (LEDs) and a plurality of second LEDs that are both mounted on the flexible printed circuit board in an arrangement to provide light through the light-transmissive element to impinge the light on skin tissue; wherein the plurality of first LEDs are configured to emit light of a first peak wavelength that is selected to at least one of stimulate nitric oxide production in the skin tissue and release endogenous stores of nitric oxide in the skin tissue; and the plurality of second LEDs are configured to emit light of a second peak wavelength that stimulates collagen production. In certain embodiments, the light-transmissive element, and the flexible printed circuit board form an eye opening that extends through the housing, the light-transmissive element, and the flexible printed circuit board. In certain embodiments, the device further comprises an eyepiece that resides within the eye opening. In certain embodiments, a portion of the eyepiece extends beyond the light-transmissive element. In certain embodiments, the device further comprises a covering element that is arranged to cover one or more portions of the housing, wherein the eye opening extends through the covering element, and wherein the housing forms a plurality of recesses that are arranged to receive one or more portions of the covering element. In certain embodiments, the device further comprises a headband that is configured to secure the housing, the light-transmissive element, and the flexible printed circuit board along a forehead of a user. In certain embodiments, the headband is provided at an angle that is non-perpendicular with portions of the light-transmissive element that are parallel with the forehead of the user. In certain embodiments, the angle is in a range from 45 degrees to about 75 degrees. In certain embodiments, the angle is in a range from 55 degrees to about 65 degrees. In certain embodiments, the first peak wavelength is in a range of from 610 nm to 630 nm and the second peak wavelength is in a range from 840 nm to 860 nm. In certain embodiments, the plurality of first LEDs and the plurality of second LEDs are non-uniformly arranged on the flexible printed circuit board. In certain embodiments, the housing, the light-transmissive element, and the flexible printed circuit board form a mask for delivering light to a face of a user, and a portion of the mask is configured to extend below a chin of the user for delivering the light of the first peak wavelength and the light of the second peak wavelength to a neck of the user. In certain embodiments, the device further comprises a plurality of third LEDs mounted on the flexible printed circuit board in an arrangement to provide light through the light-transmissive element to impinge the light on the skin tissue. In certain embodiments, the plurality of third LEDs are configured to emit light having a third peak wavelength that is in a range from 640 nm to 660 nm. In certain embodiments, the light-transmissive element comprises a lenticular lens structure.

In another aspect, any of the foregoing aspects individually or together, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWING FIGURES

The accompanying drawing figures incorporated in and forming a part of this specification illustrate several aspects of the disclosure, and together with the description serve to explain the principles of the disclosure.

FIGS. 3A, 3B, 3C, 3D, 3E, 3F and 3G show a perspective view, a back view, a left side view, a front view, a right side view, a top view and a bottom view, respectively, of the mask shown in FIGS. 1 and 2.

Figure 7:
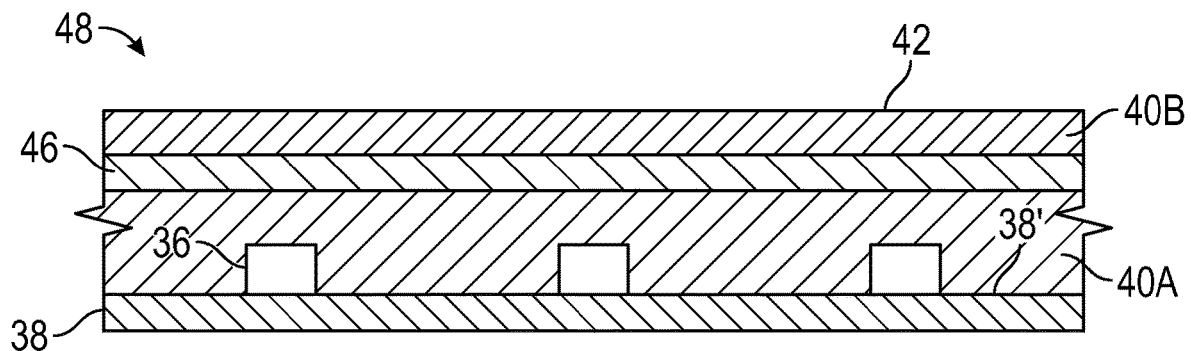

FIG. 7 is a side cross-sectional schematic view of a portion of a device for delivering light energy to living skin tissue, the device including multiple direct view light-emitting sources supported by a substrate and covered with two encapsulating material layers, with at least one functional material (e.g., wavelength conversion and/or scattering material) sheet or layer disposed between the encapsulating material layers.

Figure 8:
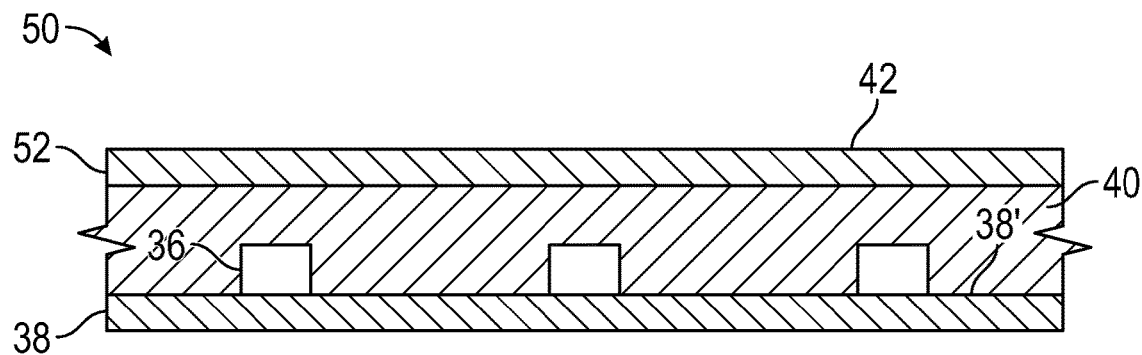

FIG. 8 is a side cross-sectional schematic view of a portion of a device for delivering light energy to living skin tissue.

Figure 9:
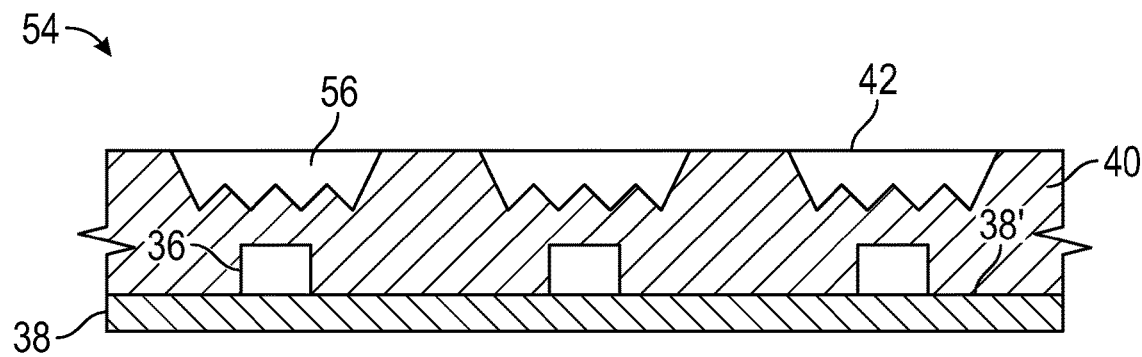

FIG. 9 is a side cross-sectional schematic view of a portion of a device for delivering light energy to living skin tissue, the device including multiple direct view light-emitting sources supported by a substrate.

Figure 10:
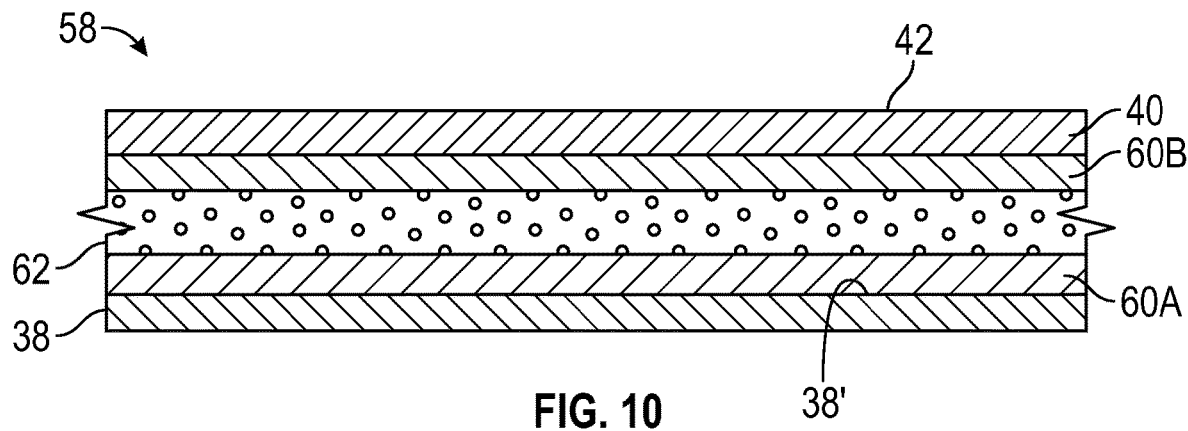

FIG. 10 is a side cross-sectional schematic view of a portion of a device for delivering light energy to living skin tissue, the device including a flexible substrate, a passive-matrix organic light-emitting diode (OLED) structure (embodied in an anode layer, a cathode layer, and an OLED stack between the anode and cathode layers).

Figure 11:
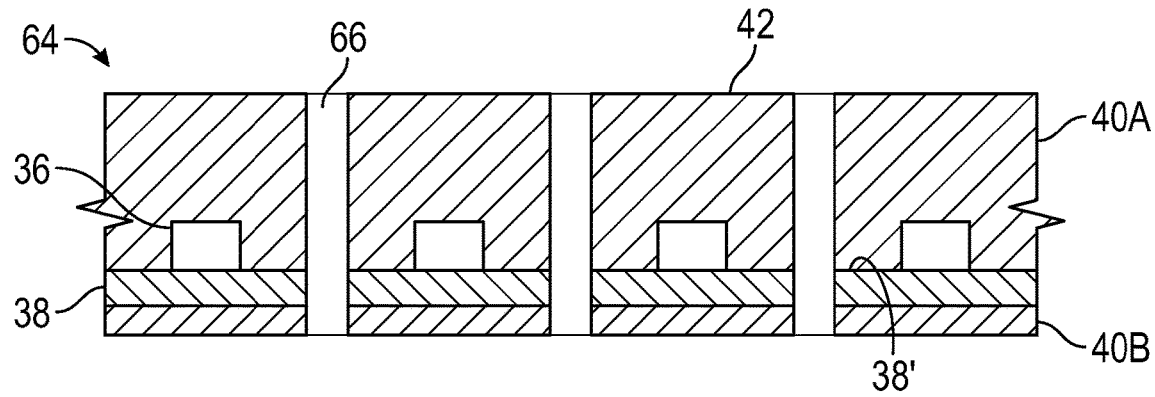

FIG. 11 is a side cross-sectional schematic view of a portion of a device for delivering light energy to living skin tissue, the device including a flexible substrate, multiple direct view light-emitting sources supported by the substrate, and encapsulating material layers arranged above and below the substrate, respectively.

Figure 12:
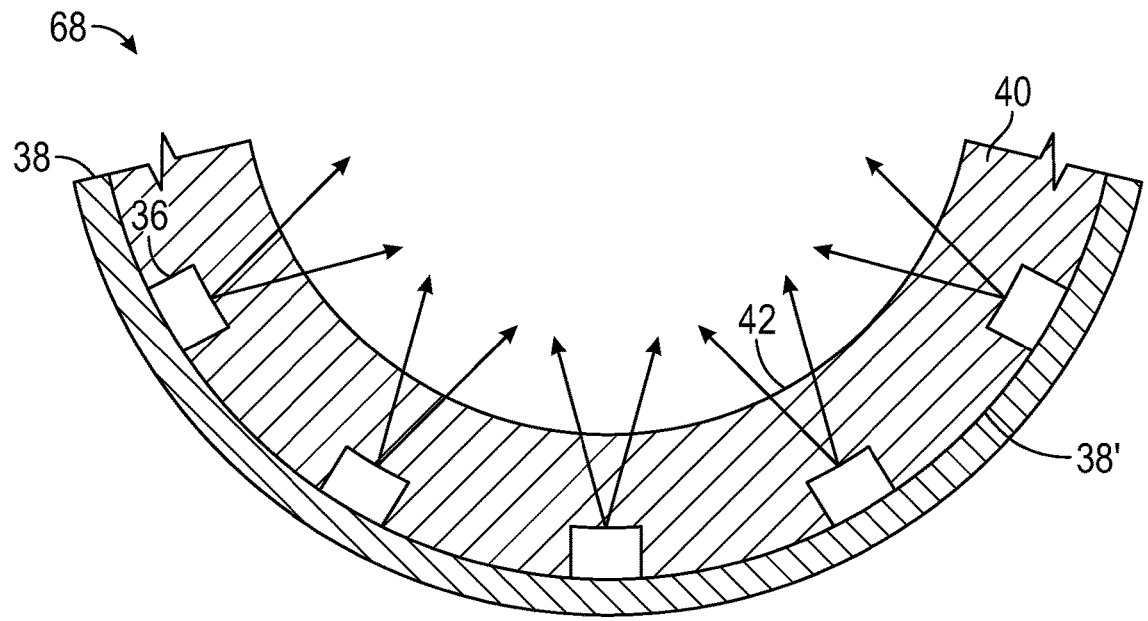

FIG. 12 is a side cross-sectional schematic view of a portion of a device for delivering light energy to living skin tissue, wherein the device includes multiple direct view light-emitting sources supported by a flexible substrate and covered by an encapsulating layer.

Figure 13:
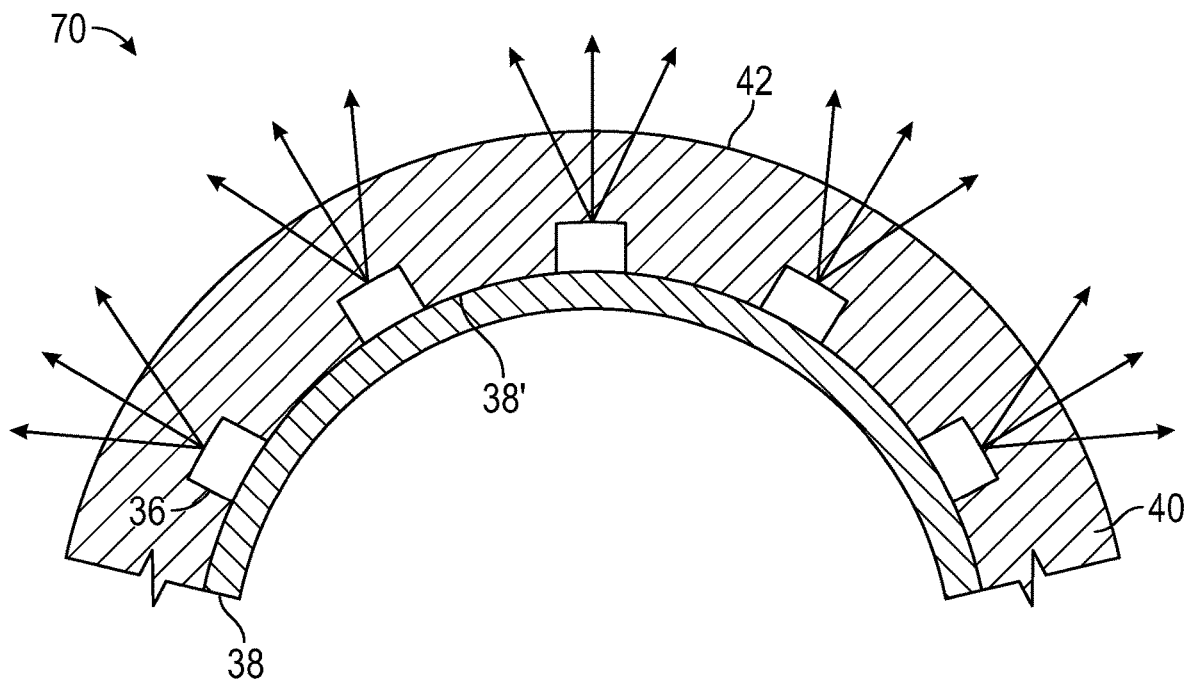

FIG. 13 is a side cross-sectional schematic view of a portion of a device for delivering light energy to living skin tissue, wherein the device includes multiple direct view light-emitting sources supported by a flexible substrate and covered by an encapsulating layer.

Figure 14A:
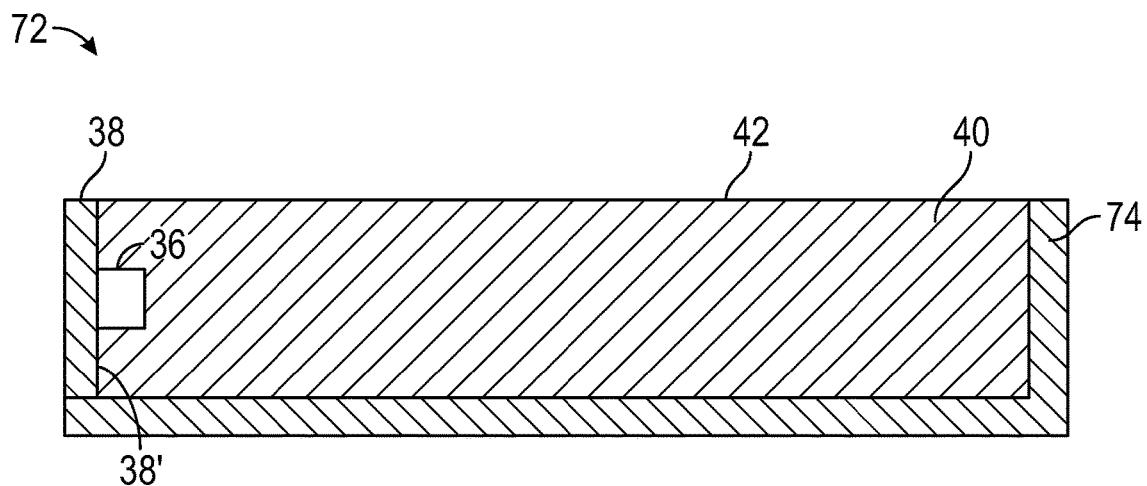

FIG. 14A is a side cross-sectional schematic view of a portion of a device for delivering light energy to living skin tissue, wherein the device is edge lit with one or more light-emitting sources supported by a flexible printed circuit board (PCB) that preferably includes a reflective surface.

Figure 14B:
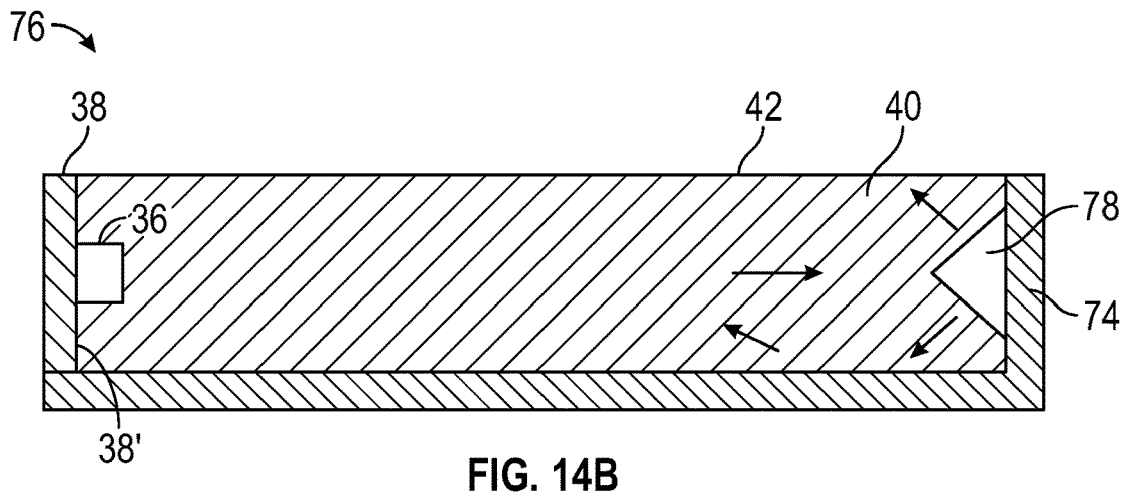

FIG. 14B is a side cross-sectional schematic view of a portion of a device for delivering light energy to living skin tissue, wherein the device is edge lit with one or more light-emitting sources supported by a flexible PCB that preferably includes a reflective surface, and the device comprises a reflective element.

Figure 15:
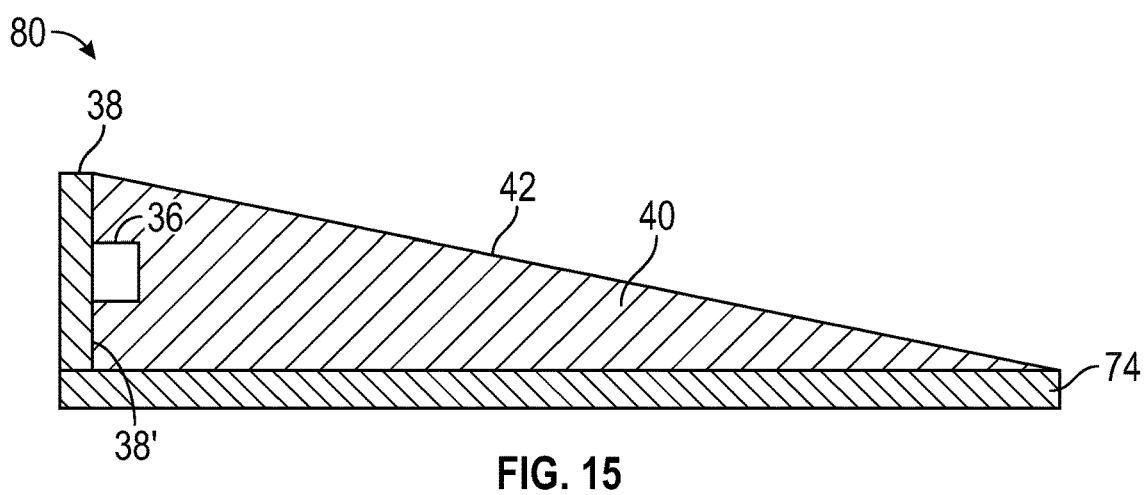

FIG. 15 is a side cross-sectional schematic view of a portion of a device for delivering light energy to living skin tissue, wherein the device is edge lit with one or more light-emitting sources supported by a flexible PCB that preferably includes a reflective surface. A non-light-transmitting face of the device is bounded by a flexible reflective substrate arranged to reflect light toward a light-transmissive outer surface of the device. The flexible PCB, the light-emitting source(s), and the flexible reflective substrate are covered with an encapsulating material.

Figure 16:
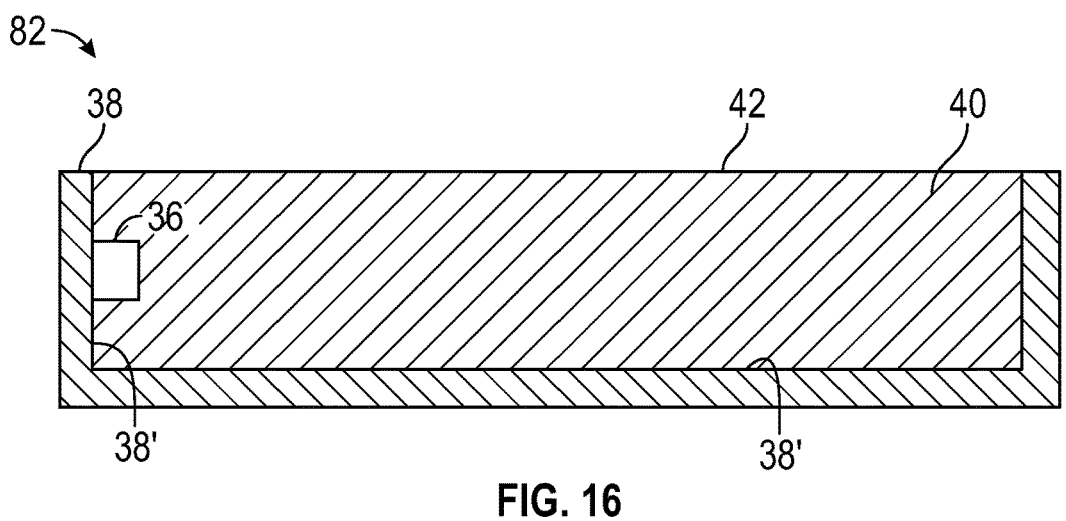

FIG. 16 is a side cross-sectional schematic view of a portion of a device for delivering light energy to living skin tissue, wherein the device is edge lit with one or more light-emitting sources supported by a flexible PCB that bounds multiple edges and a face of the device.

Figure 17:
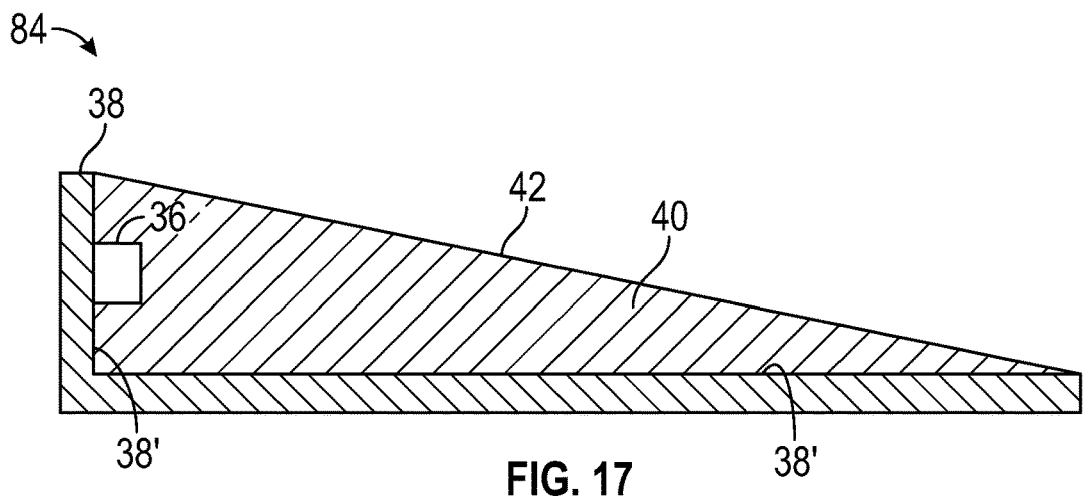

FIG. 17 is a side cross-sectional schematic view of a portion of a device for delivering light energy to living skin tissue, wherein the device is edge lit with one or more light-emitting sources supported by a flexible PCB that bounds one edge and one face of the device.

Figure 18:
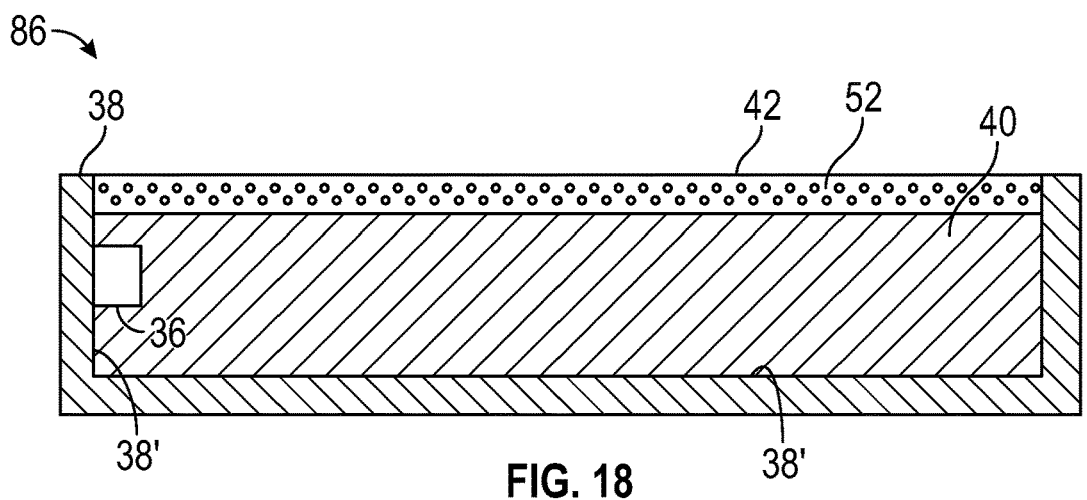

FIG. 18 is a side cross-sectional schematic view of a portion of a device for delivering light energy to living skin tissue, wherein the device is edge lit with one or more light-emitting sources supported by a flexible PCB that bounds multiple edges and a face of the device.

Figure 19:
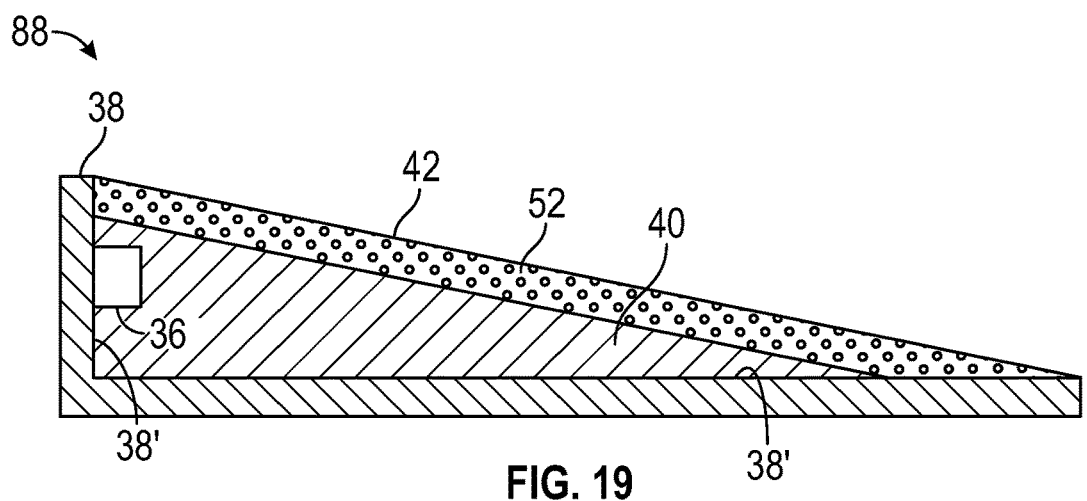

FIG. 19 is a side cross-sectional schematic view of a portion of a device for delivering light energy to living skin tissue, wherein the device is edge lit with one or more light-emitting sources supported by a flexible PCB that bounds one edge and one face of the device.

Figure 20:
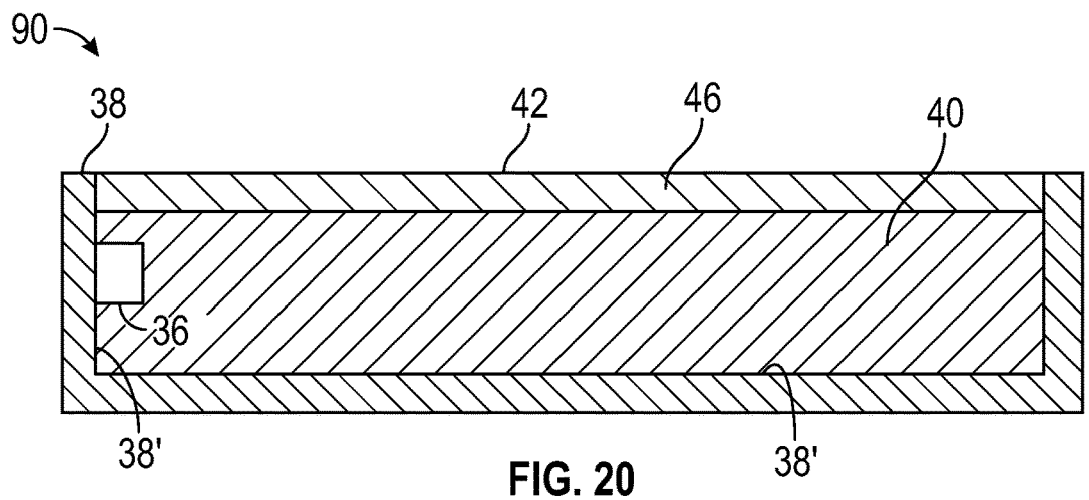

FIG. 20 is a side cross-sectional schematic view of a portion of a device for delivering light energy to living skin tissue, wherein the device is edge lit with one or more light-emitting sources supported by a flexible PCB that bounds multiple edges and a face of the device.

Figure 21:
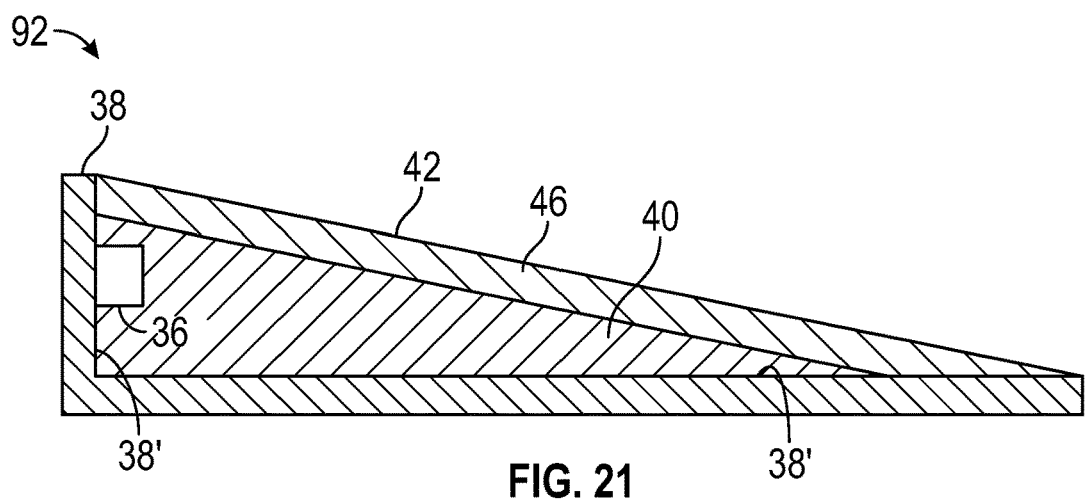

FIG. 21 is a side cross-sectional schematic view of a portion of a device for delivering light energy to living skin tissue, wherein the device is edge lit with one or more light-emitting sources supported by a flexible PCB that bounds one edge and one face of the device.

Figure 22:
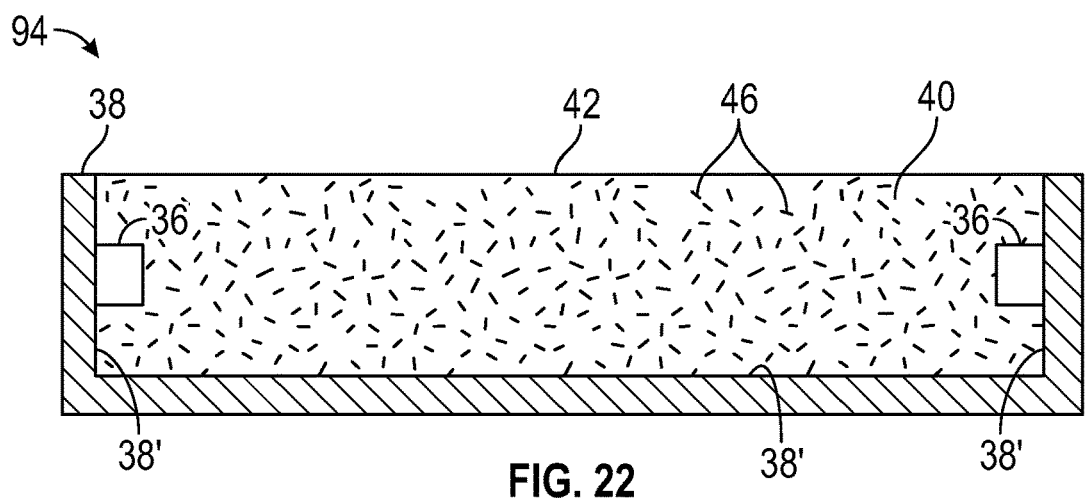

FIG. 22 is a side cross-sectional schematic view of a portion of a device for delivering light energy to living skin tissue, wherein the device is edge lit along multiple edges with multiple light-emitting sources supported by a flexible PCB having a reflective surface arranged to reflect light toward a light-transmissive outer surface of the device. The flexible PCB and light-emitting sources are covered with an encapsulating material, and a wavelength conversion material is distributed in the encapsulating material.

Figure 23A:
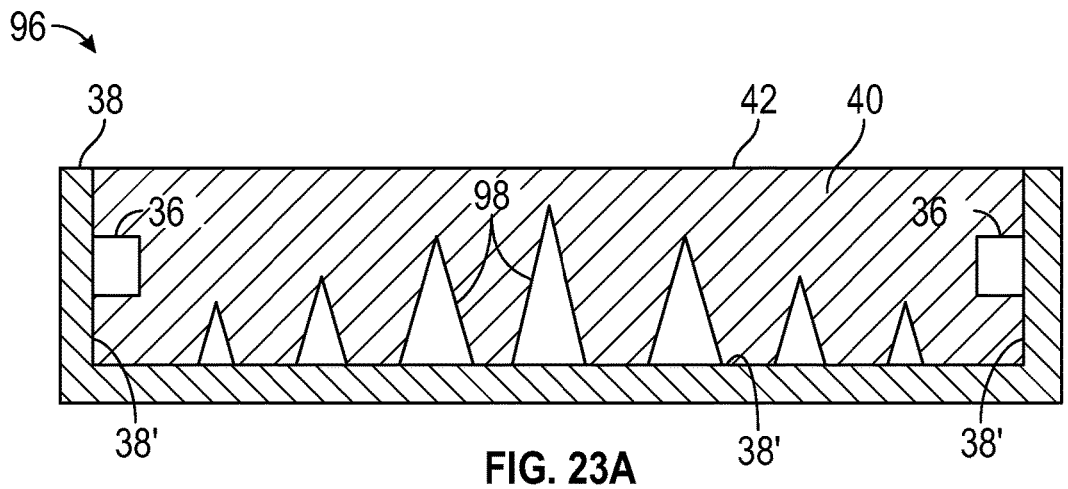

FIG. 23A is a side cross-sectional schematic view of a portion of a device for delivering light energy to living skin tissue, wherein the device is edge lit along multiple edges with multiple light-emitting sources supported by a flexible PCB having a reflective surface arranged to reflect light toward a light-transmissive outer surface of the device. The device further includes raised light extraction features supported by the flexible PCB, with such features serving to reflect laterally-transmitted light toward the outer surface. An encapsulating material is provided over the flexible PCB, the light-emitting sources, and the light extraction features.

Figure 23B:
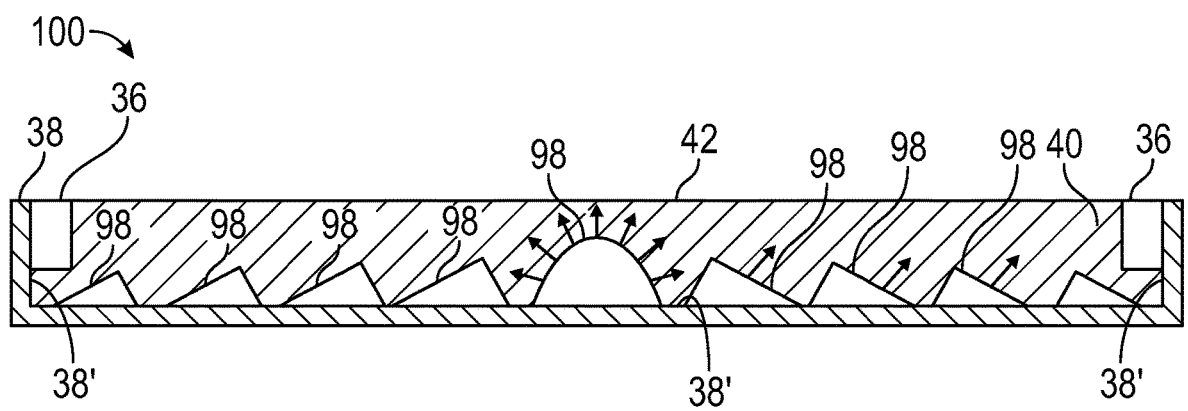

FIG. 23B is a side cross-sectional schematic view of a portion of a device for delivering light energy to living skin tissue, wherein the device is edge lit along multiple edges with multiple light-emitting sources supported by a flexible PCB having a reflective surface arranged to reflect light toward a light-transmissive outer surface of the device. The device further includes raised light extraction features supported by the flexible PCB, with such features serving to reflect laterally-transmitted light toward the outer surface. An encapsulating material is provided over the flexible PCB, the light-emitting sources, and the light extraction features.

Figure 24:
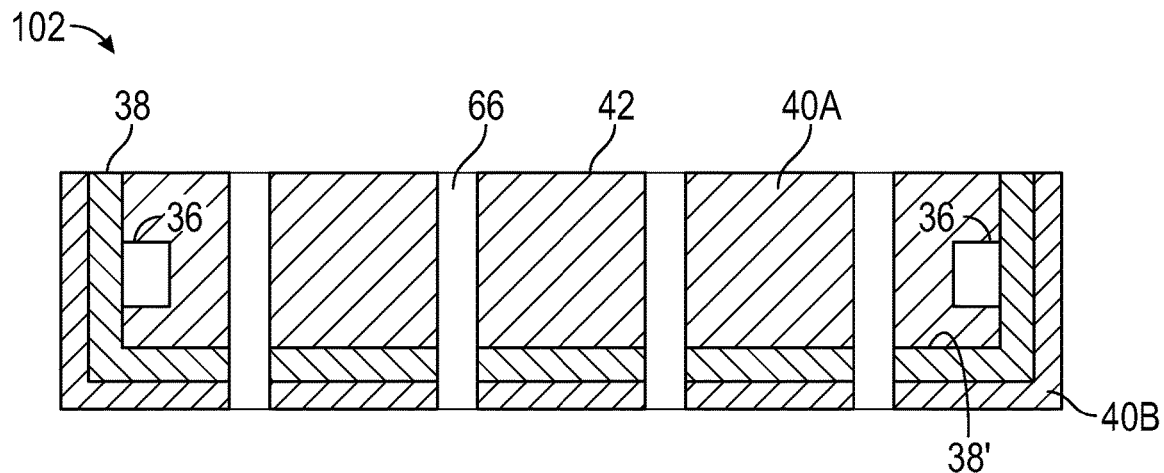

FIG. 24 is a side cross-sectional schematic view of a portion of a device for delivering light energy to living skin tissue, wherein the device is edge lit along multiple edges with multiple light-emitting sources supported by a flexible PCB having a reflective surface arranged to reflect light toward a light-transmissive outer surface of the device.

Figure 25C:
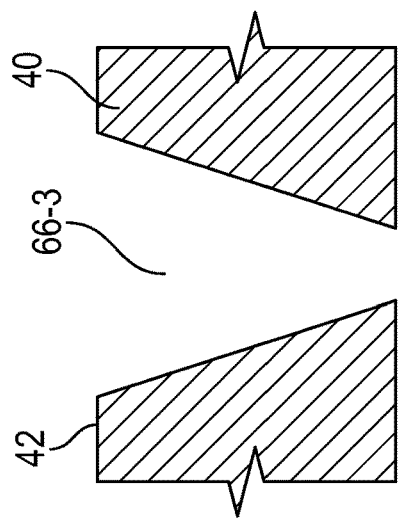
Figure 25B:
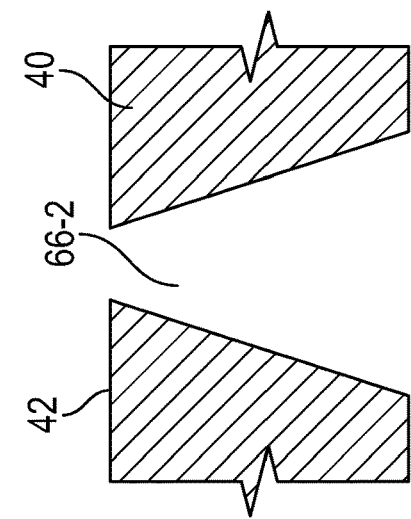
Figure 25A:
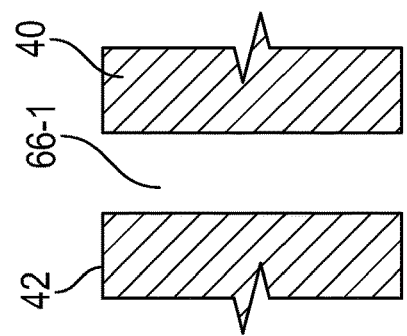

FIG. 25A is a cross-sectional view of a first exemplary hole definable through a device for delivering light energy to living skin tissue, the hole having a diameter that is substantially constant with depth.

FIG. 25B is a cross-sectional view of a second exemplary hole definable through a device for delivering light energy to living skin tissue, the hole having a diameter that increases with increasing depth.

FIG. 25C is a cross-sectional view of a second exemplary hole definable through a device for delivering light energy to living skin tissue, the hole having a diameter that decreases with increasing depth.

Figure 26:
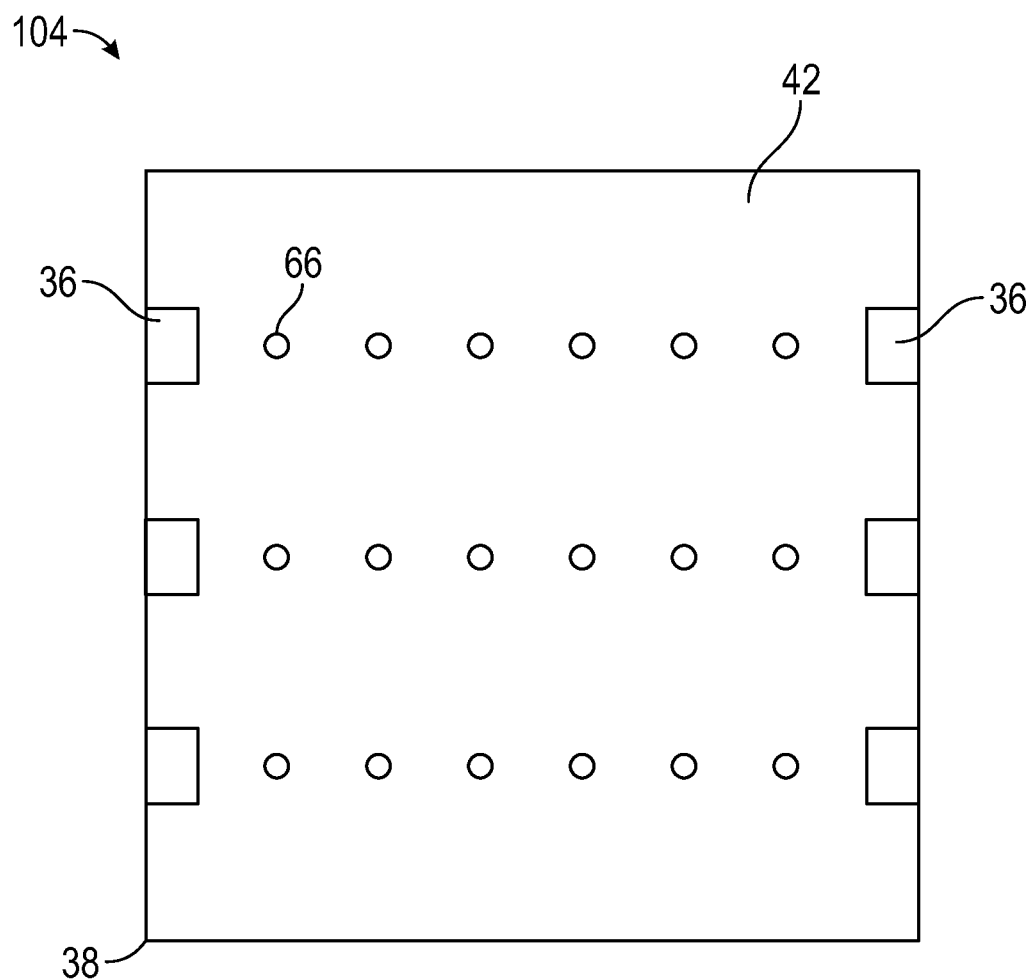

FIG. 26 is a top schematic view of at least a portion of a device for delivering light energy to living skin tissue, wherein the device is edge-lit along multiple edges with multiple light-emitting sources supported by a flexible PCB, and multiple holes or perforations of substantially uniform size and substantially uniform distribution are defined through the flexible PCB.

Figure 27:
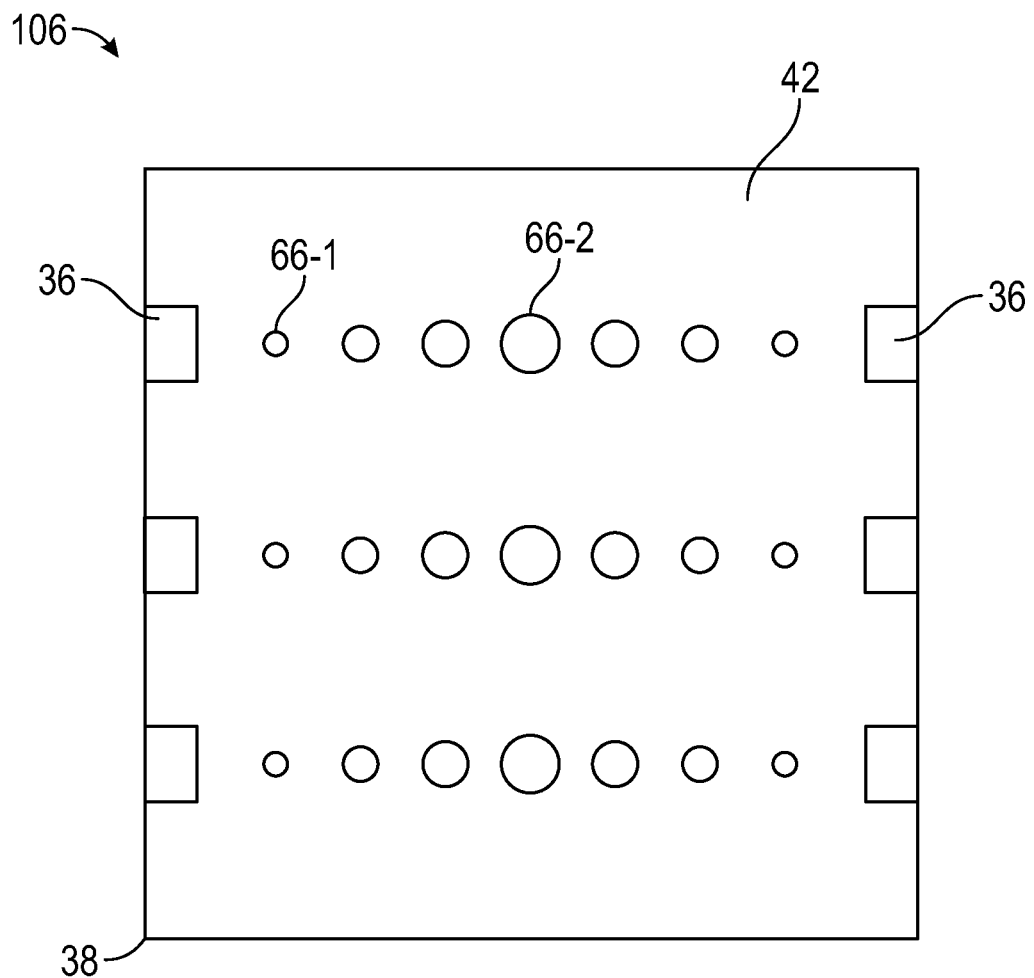

FIG. 27 is a top schematic view of at least a portion of a device for delivering light energy to living skin tissue, wherein the device is lighted along multiple edges with multiple light-emitting sources supported by a flexible PCB, and multiple holes or perforations of different sizes but with a substantially uniform distribution are defined through the flexible PCB.

Figure 28:
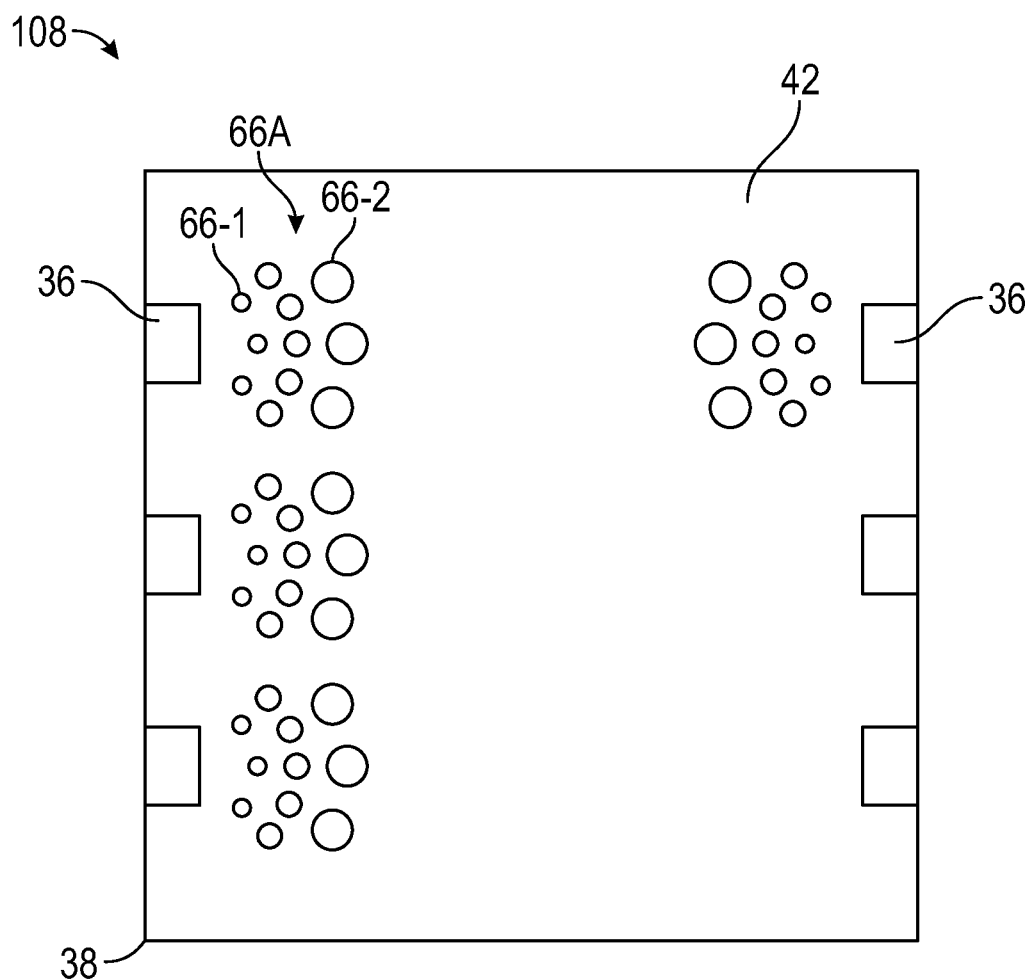

FIG. 28 is a top schematic view of at least a portion of a device for delivering light energy to living skin tissue, wherein the device is lighted along multiple edges with multiple light-emitting sources supported by a flexible PCB, and multiple holes or perforations of different sizes are provided in clusters and defined through the flexible PCB proximate to selected light-emitting sources.

Figure 29:
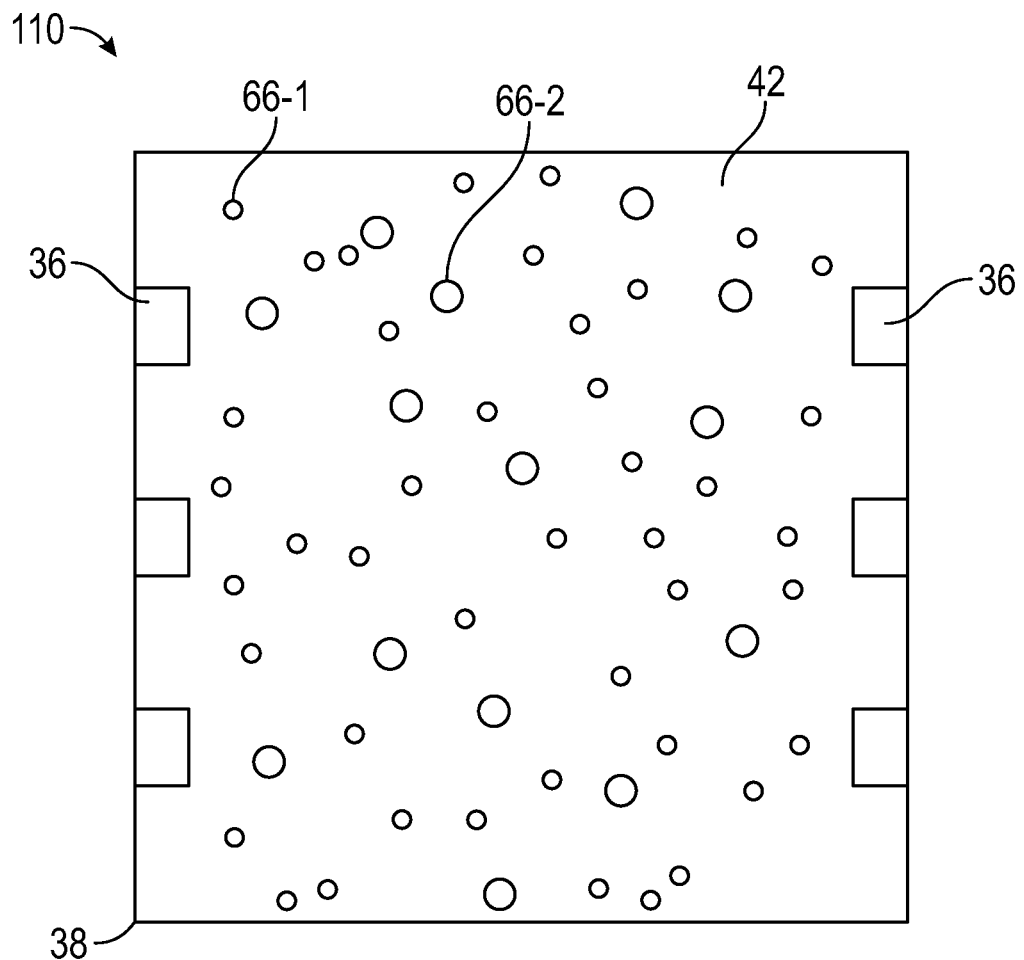

FIG. 29 is a top schematic view of at least a portion of a device for delivering light energy to living skin tissue, wherein the device is lighted along multiple edges with multiple light-emitting sources supported by a flexible PCB, and multiple holes or perforations of different sizes and with a non-uniform (e.g., random) distribution are defined through the flexible PCB.

Figure 30A:
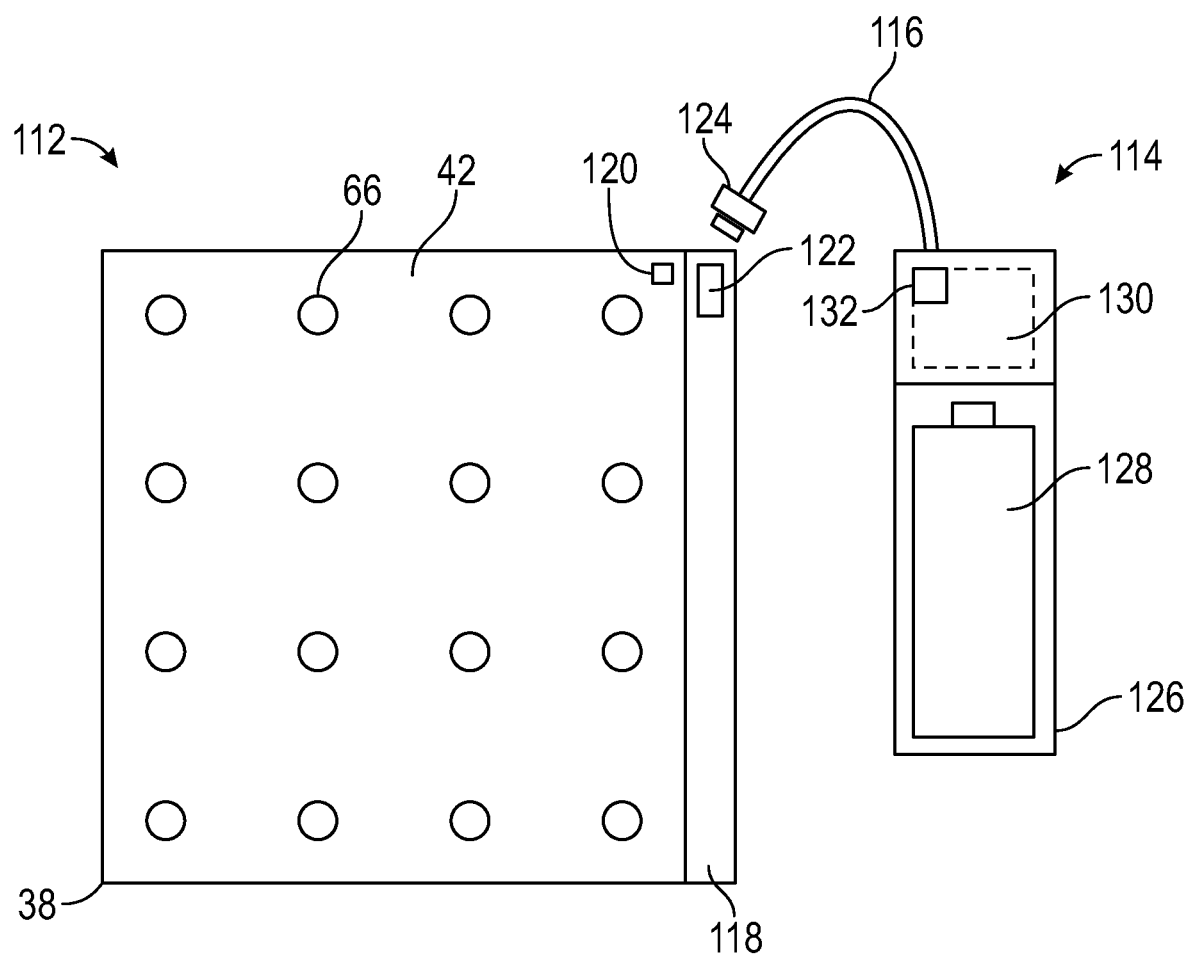

FIG. 30A is a top schematic view of at least a portion of a light-emitting device for delivering light energy to living skin tissue and at least a portion of a battery/control module, wherein an elongated electrical cord is associated with the battery/control module for connecting the battery/control module to the light-emitting device.

Figure 30B:
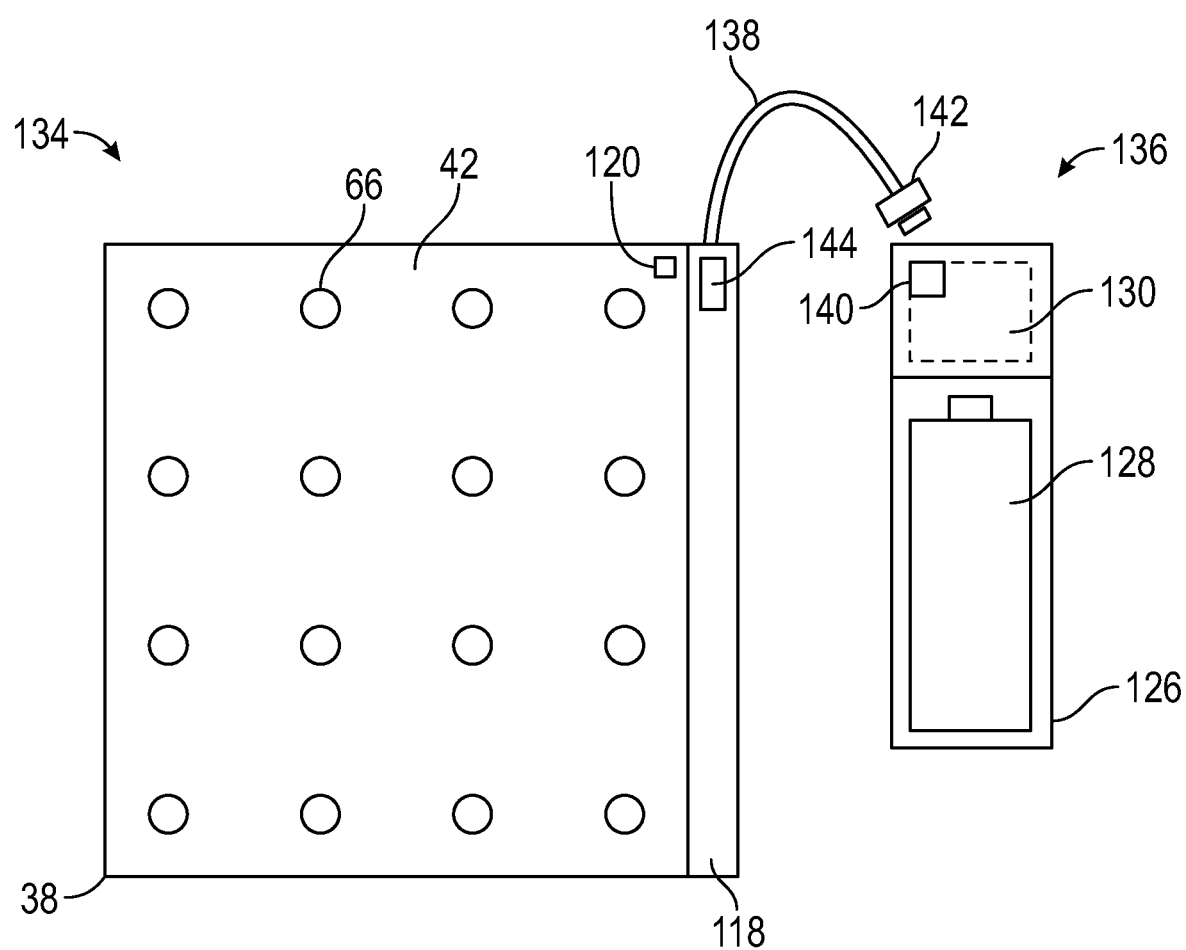

FIG. 30B is a top schematic view of at least a portion of a light-emitting device for delivering light energy to living skin tissue and at least a portion of a battery/control module, wherein an elongated electrical cord is associated with the light-emitting device for connecting the light-emitting device to the battery/control module.

Figure 31:
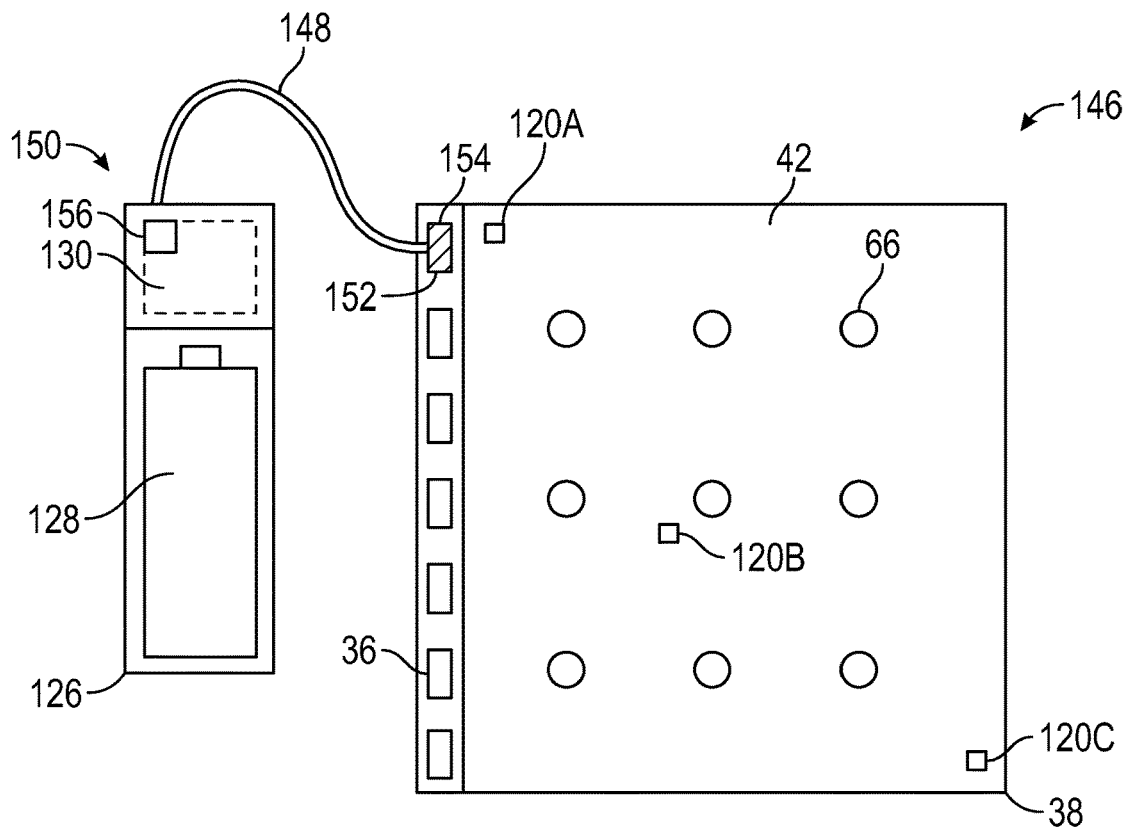

FIG. 31 is a top schematic view of at least a portion of a light-emitting device for delivering light energy to living skin tissue and being connected via an electrical cord to a battery/control module, wherein the light-emitting device includes multiple light emitters, multiple holes or perforations, and multiple sensors.

Figure 32A:
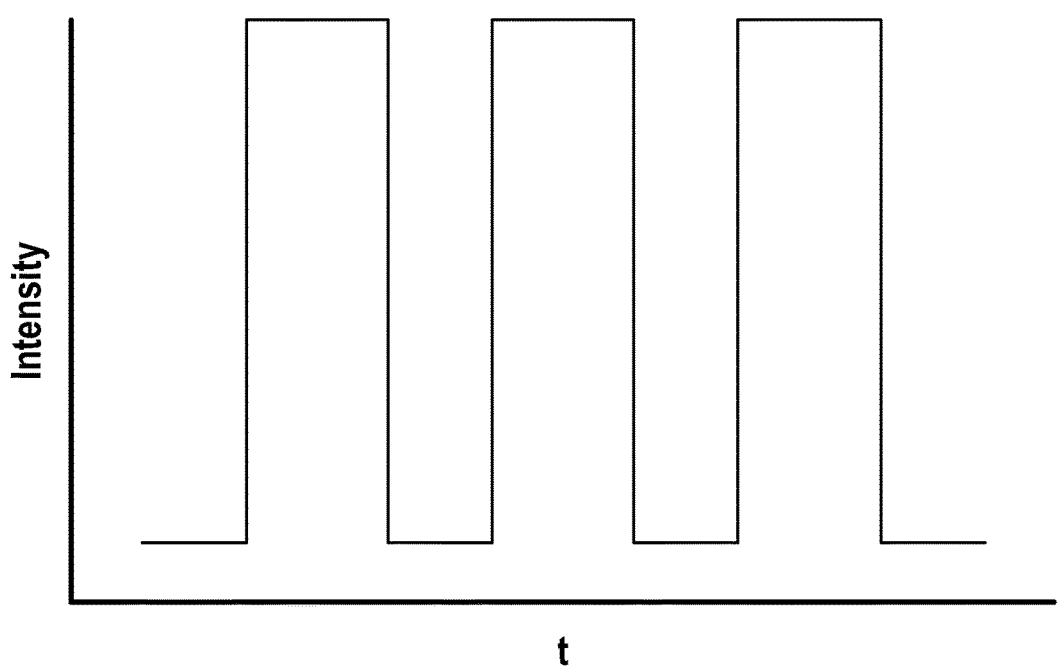

FIG. 32A is a plot of intensity versus time embodying a first exemplary illumination cycle that may be used with at least one emitter of a light-emitting device for delivering light energy to living skin tissue as disclosed herein.

Figure 32B:
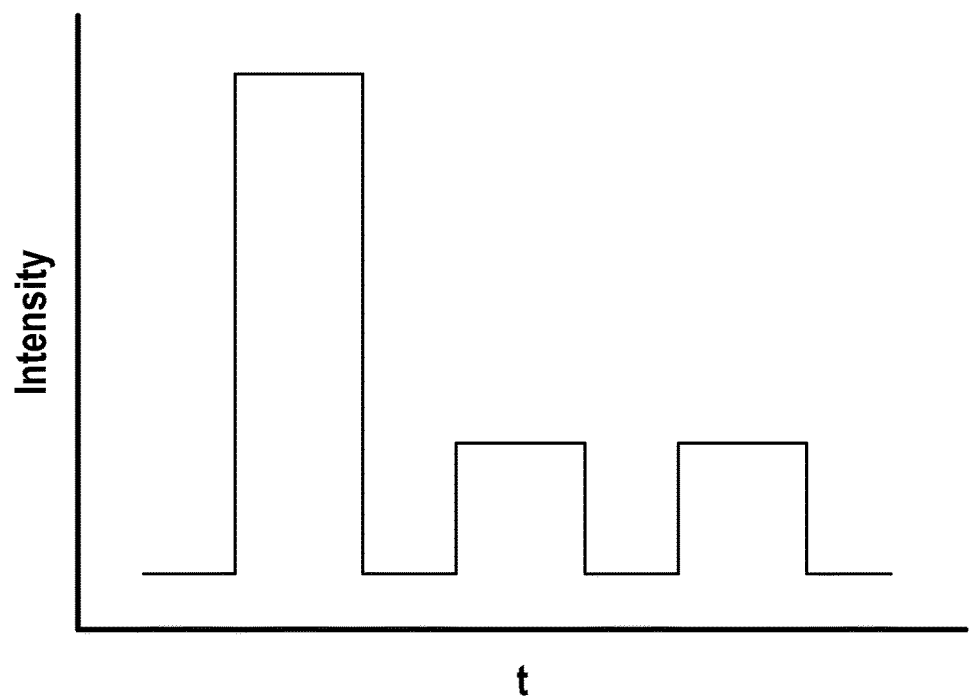

FIG. 32B is a plot of intensity versus time embodying a second exemplary illumination cycle that may be used with at least one emitter of a light-emitting device for delivering light energy to living skin tissue as disclosed herein.

Figure 32C:
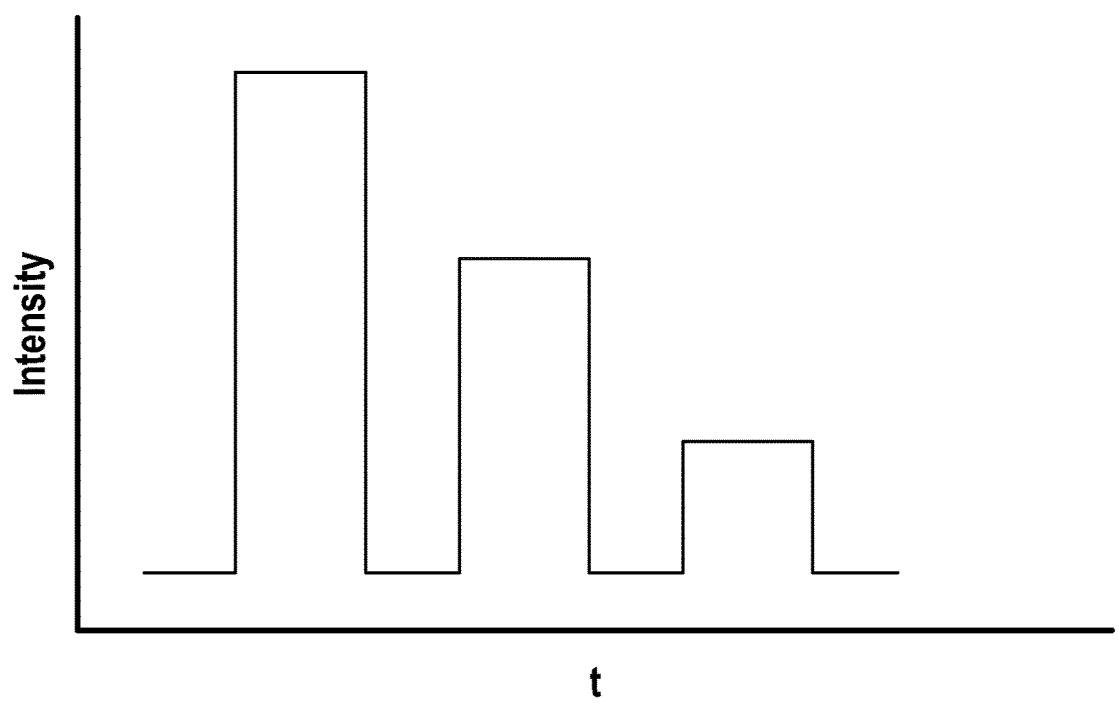

FIG. 32C is a plot of intensity versus time embodying a third exemplary illumination cycle that may be used with at least one emitter of a light-emitting device for delivering light energy to living skin tissue as disclosed herein.

Figure 33:
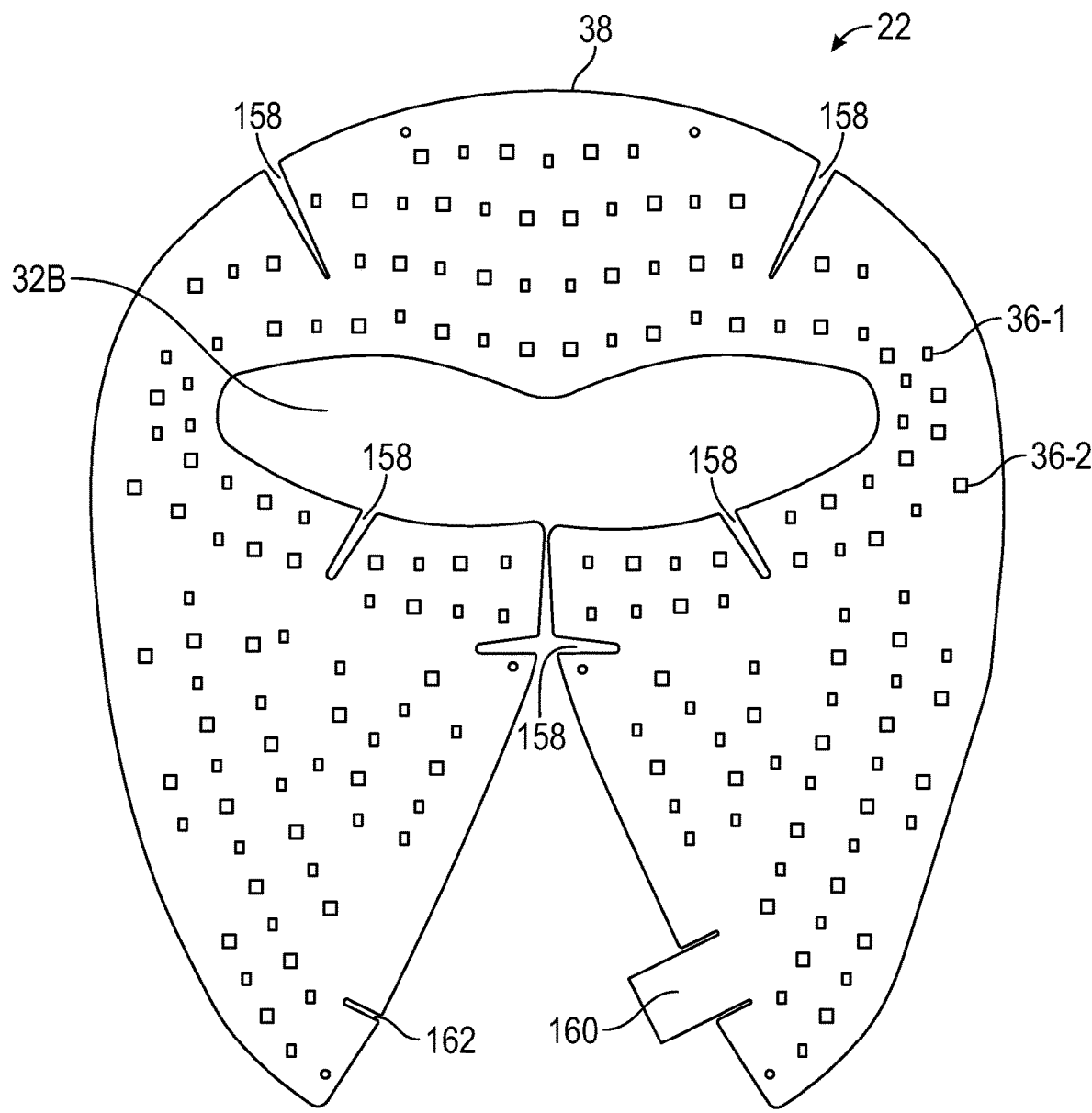

FIG. 33 is a schematic plan view of a flexible PCB configured for placement of infrared light-emitting diodes (LEDs) (which emit light of wavelength in the range of from about 840 nanometers (nm) to about 860 nm and are represented by smaller boxes) and red LEDs (which emit light of wavelength in the range of from about 610 nm to about 630 nm and are represented by slightly larger boxes).

Figure 34A:
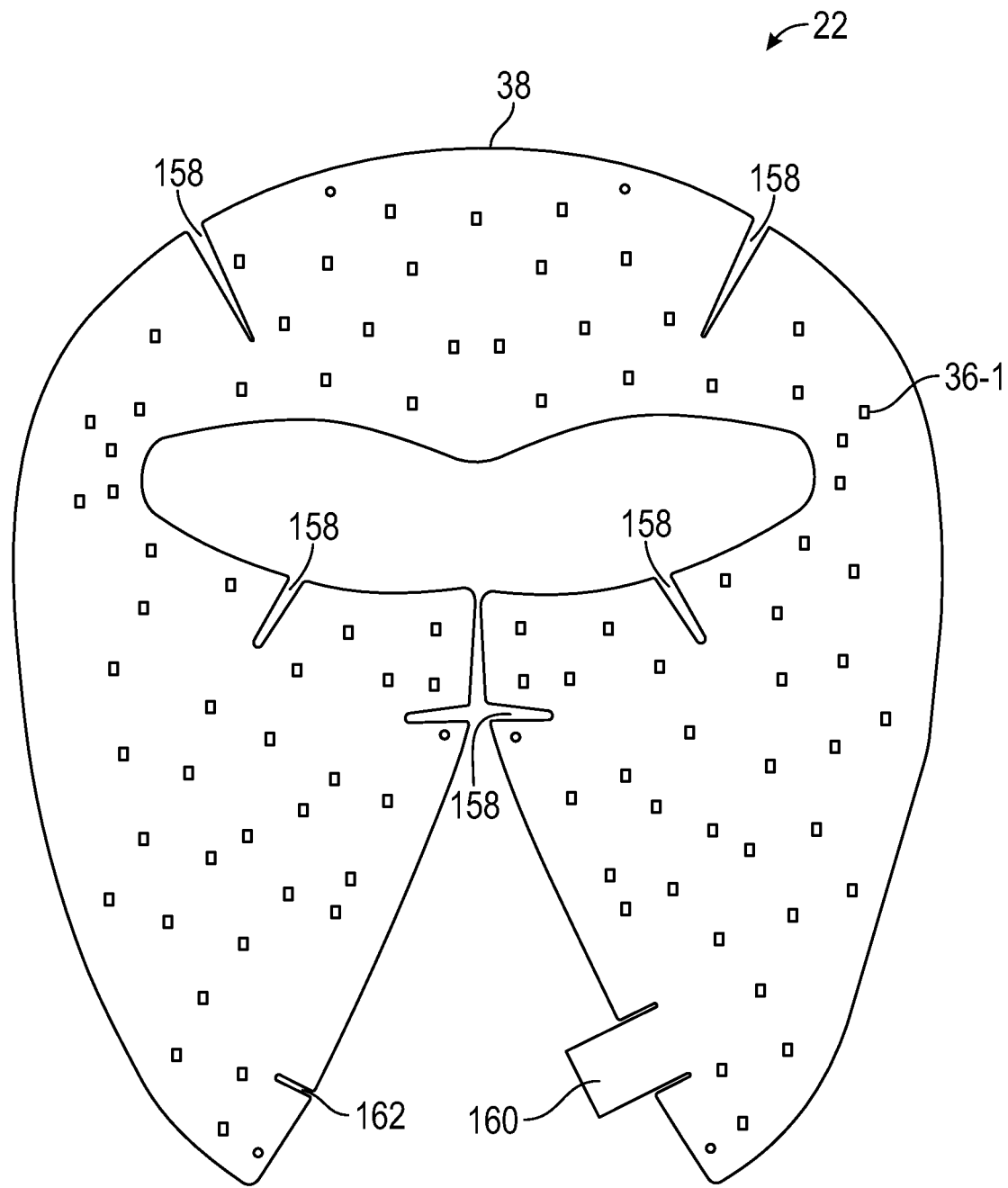

FIG. 34A is a schematic plan view of the flexible PCB of FIG. 33 showing only the placement of infrared LEDs (smaller boxes).

Figure 34B:
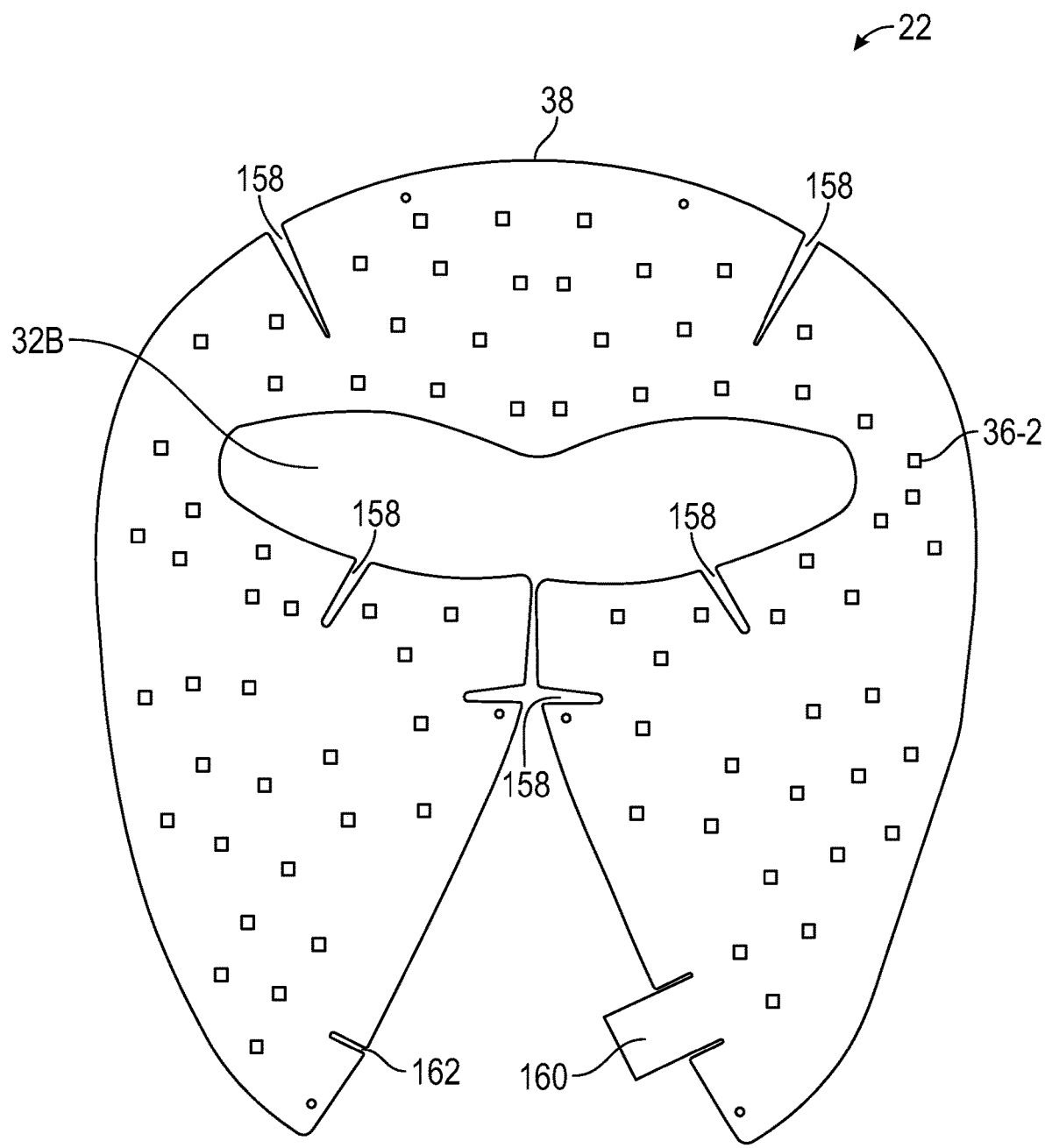

FIG. 34B is a schematic plan view of the flexible PCB of FIG. 33 showing only the placement of red LEDs (slightly larger boxes).

Figure 35:
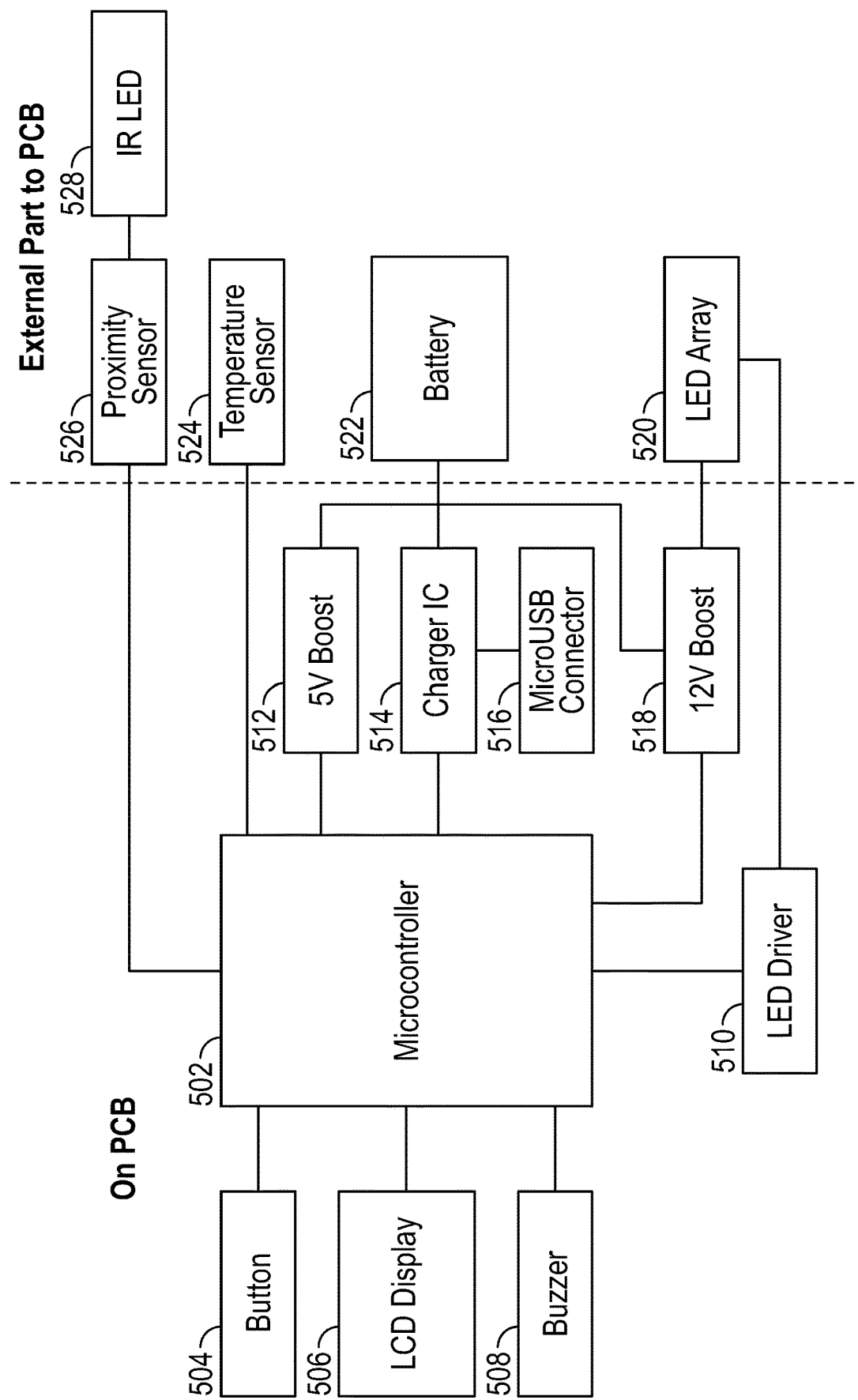

FIG. 35 is a schematic diagram showing interconnections between components of a light-emitting device or delivering light energy to skin tissue of a patient according to one embodiment.

Figure 36:
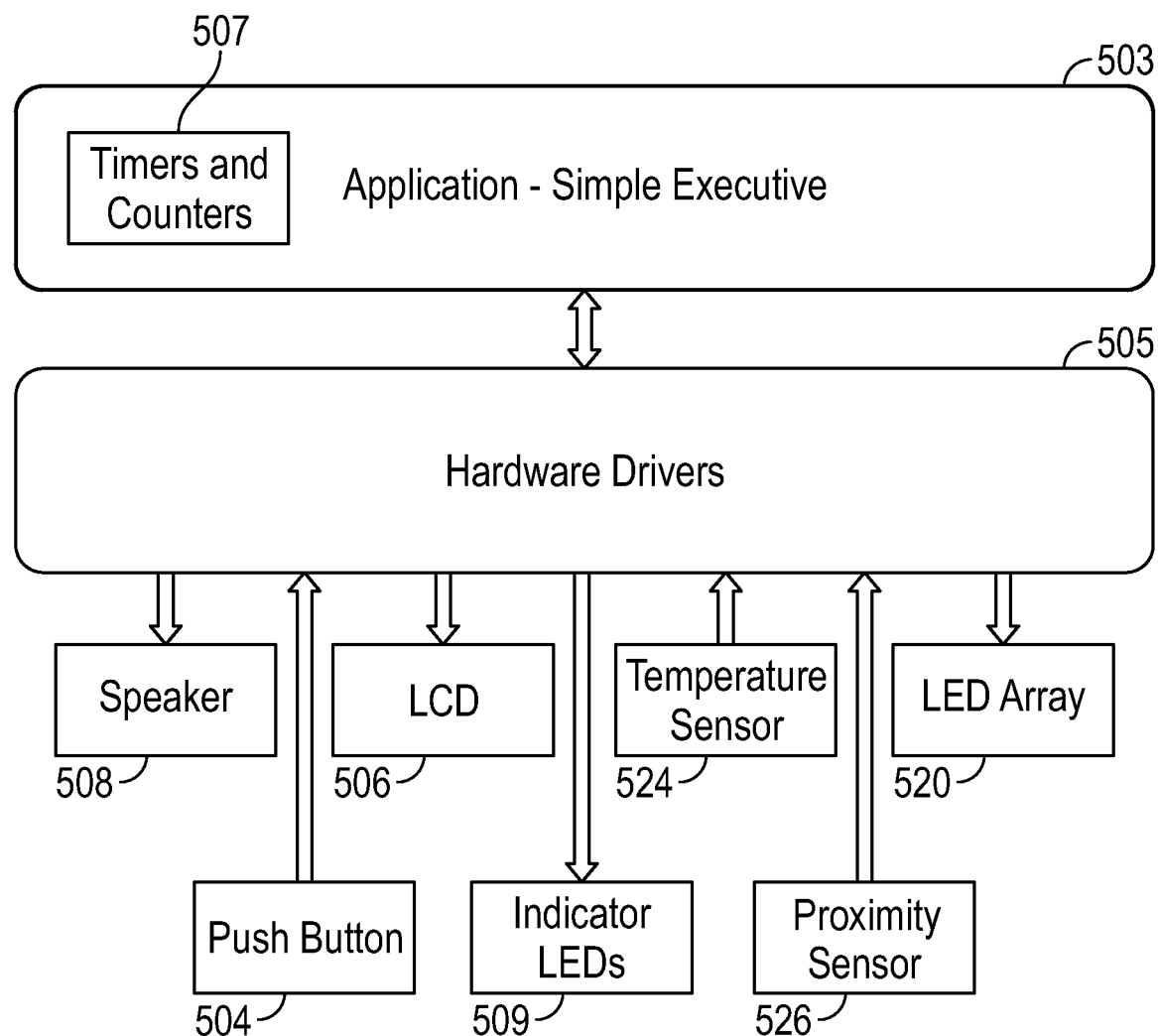

FIG. 36 is a schematic diagram depicting an interface between hardware drivers, functional components, and a software application suitable for operating a light-emitting device according to FIG. 35.

Figure 37:
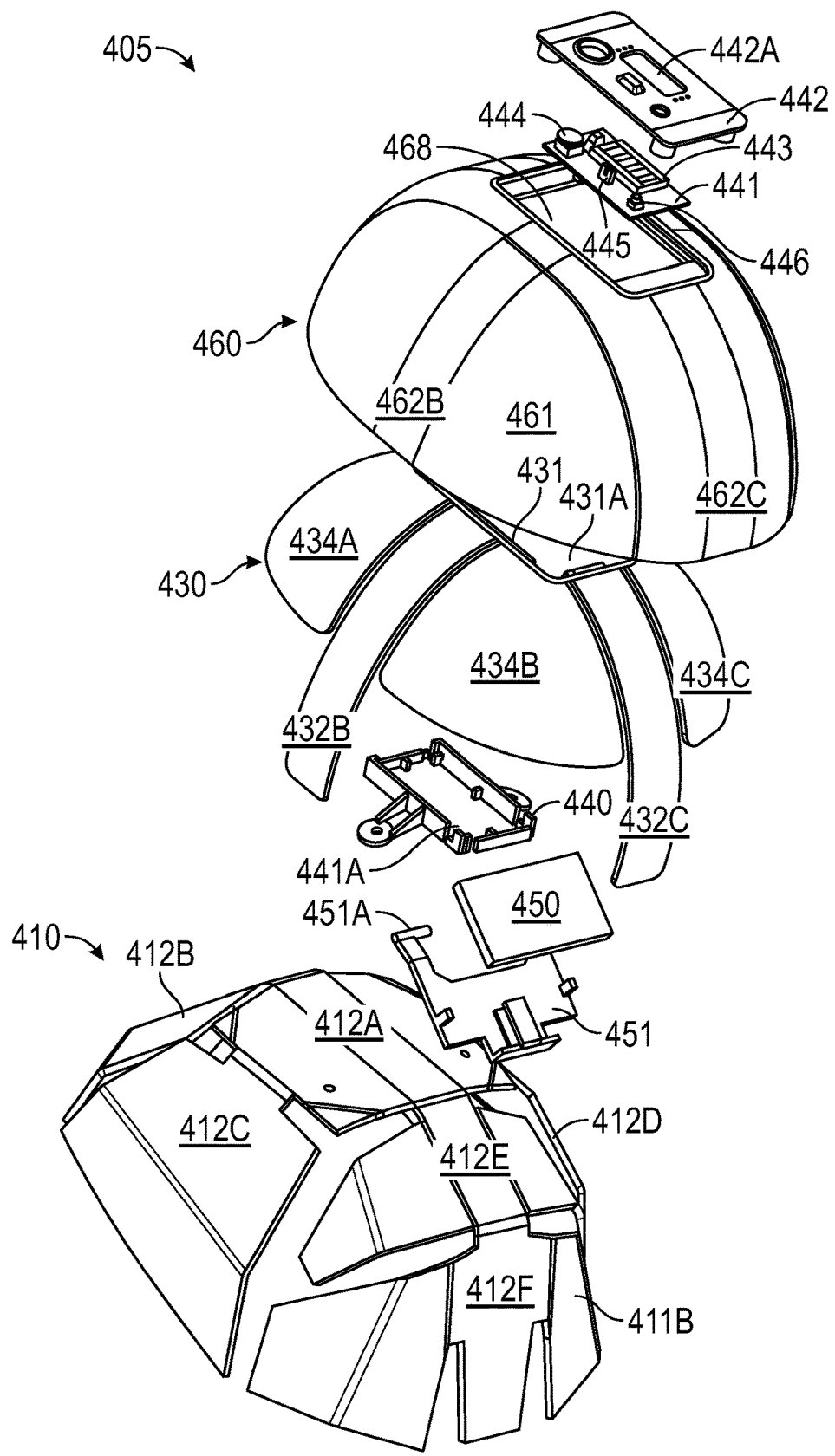

FIG. 37 is an exploded view of a light-emitting device embodied in a wearable cap for delivering light energy to a scalp of a patient, the device including at least one light emitter supported by a flexible PCB arranged in a concave configuration, a concave support member shaped to receive the flexible PCB and support a battery and control module, and a fabric covering arranged to cover the support member and flexible PCB.

Figure 38:
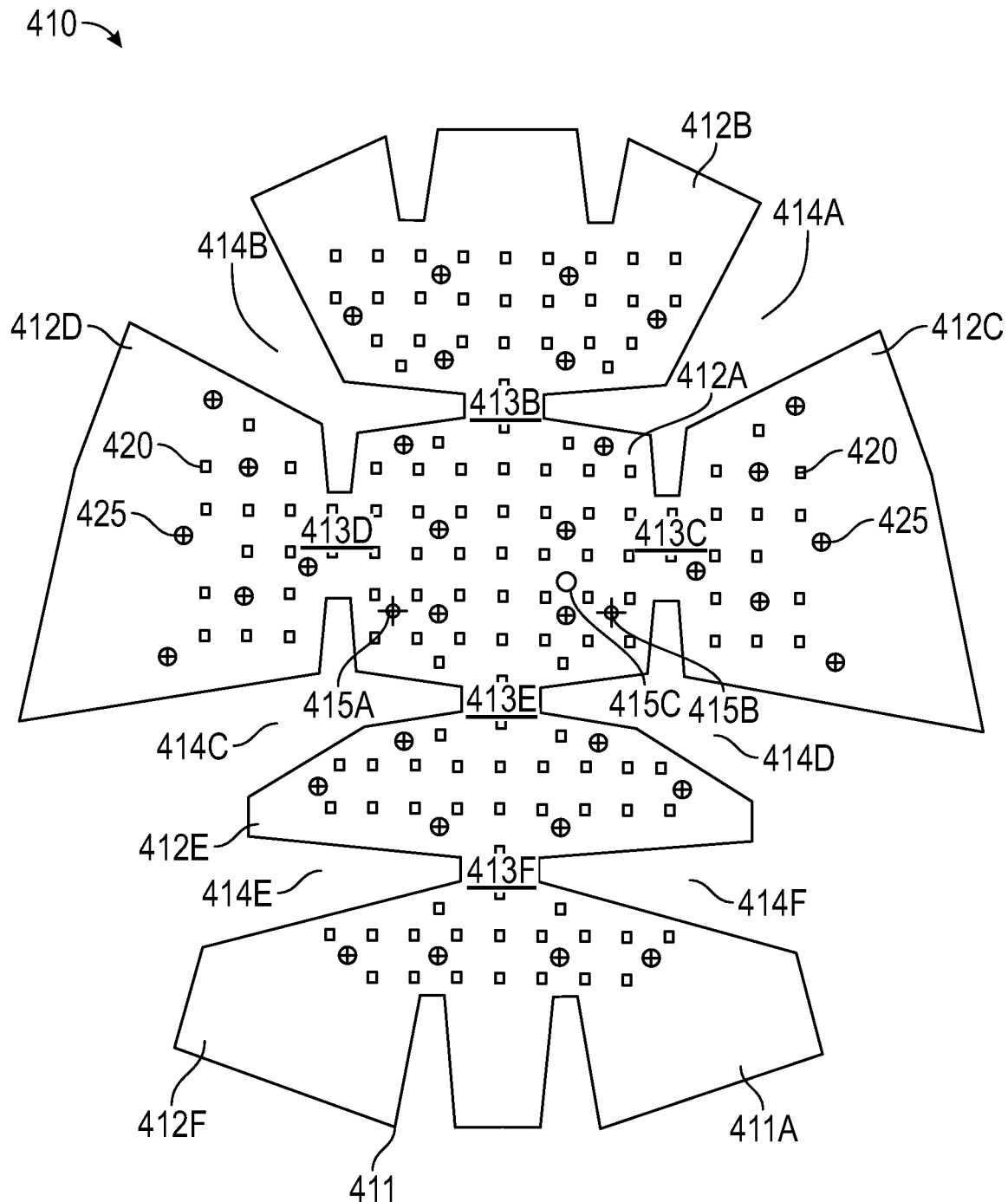

FIG. 38 is a bottom plan view of the flexible PCB of FIG. 31 prior to being shaped into a concave configuration.

Figure 39:
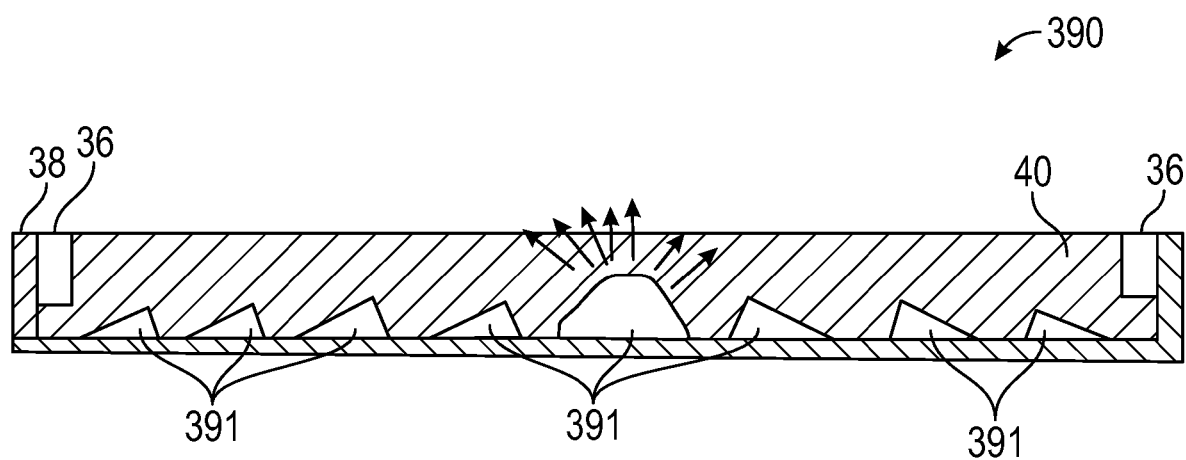

FIG. 39 schematically depicts a region of a lens (e.g., a lens that can be used as the lens in FIGS. 1 and 2) that comprises a plurality of light scattering regions.

Figure 40:
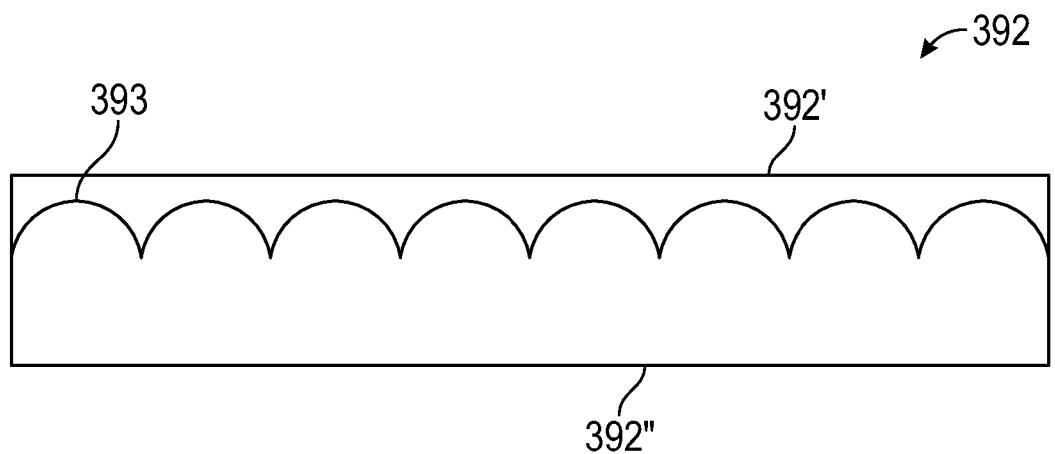

FIG. 40 schematically depicts a region of a lens (e.g., a lens that can be used as the lens in FIGS. 1 and 2) that comprises a lenticular lens region.

Figure 1:
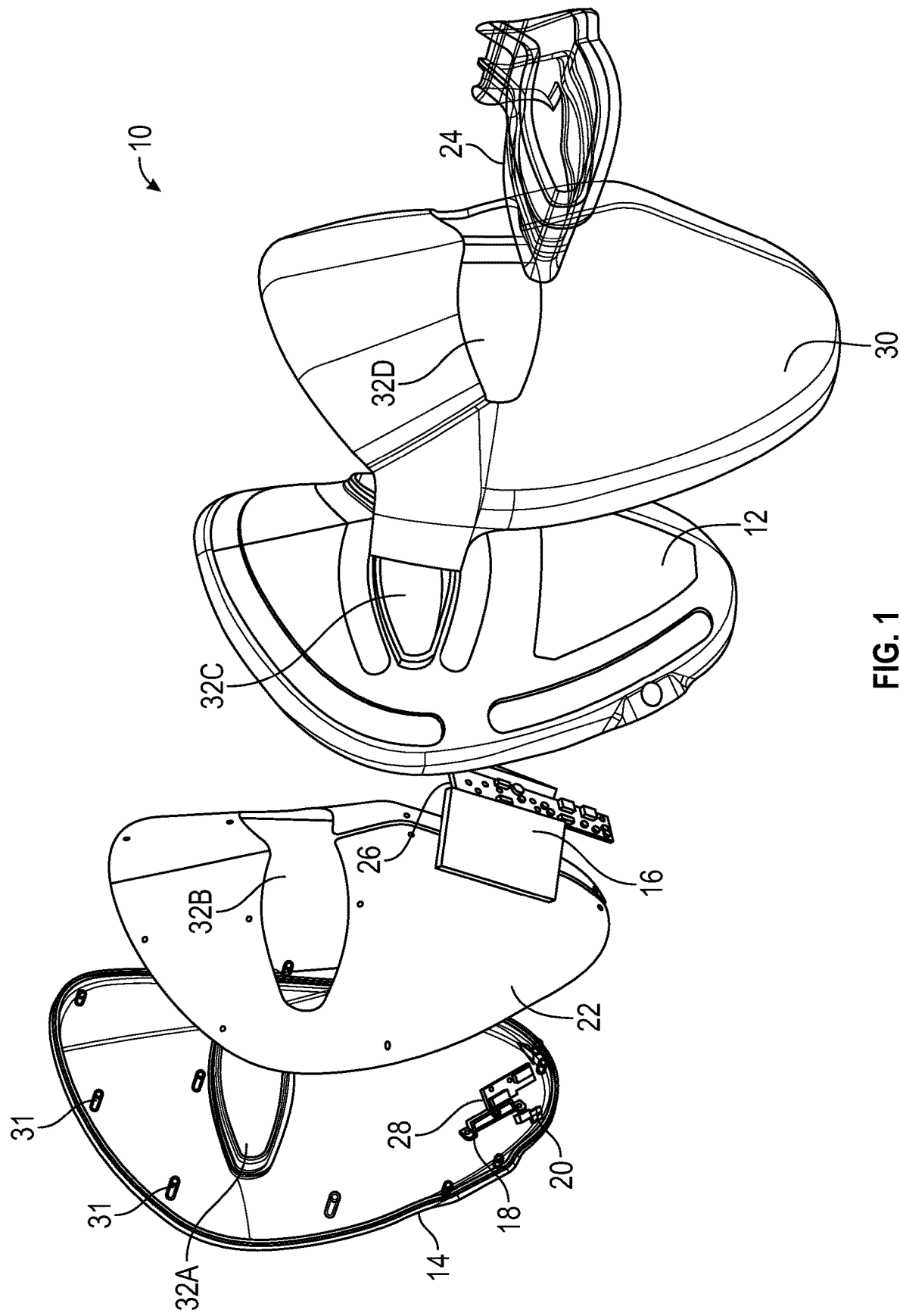
FIG. 1 is an exploded view of one embodiment of a mask for delivering light energy to living skin tissue as described herein, showing a front, left side, perspective view of a mask, where the mask includes multiple direct view light-emitting sources supported by a substrate and covered with an encapsulating material layer.
Figure 2:
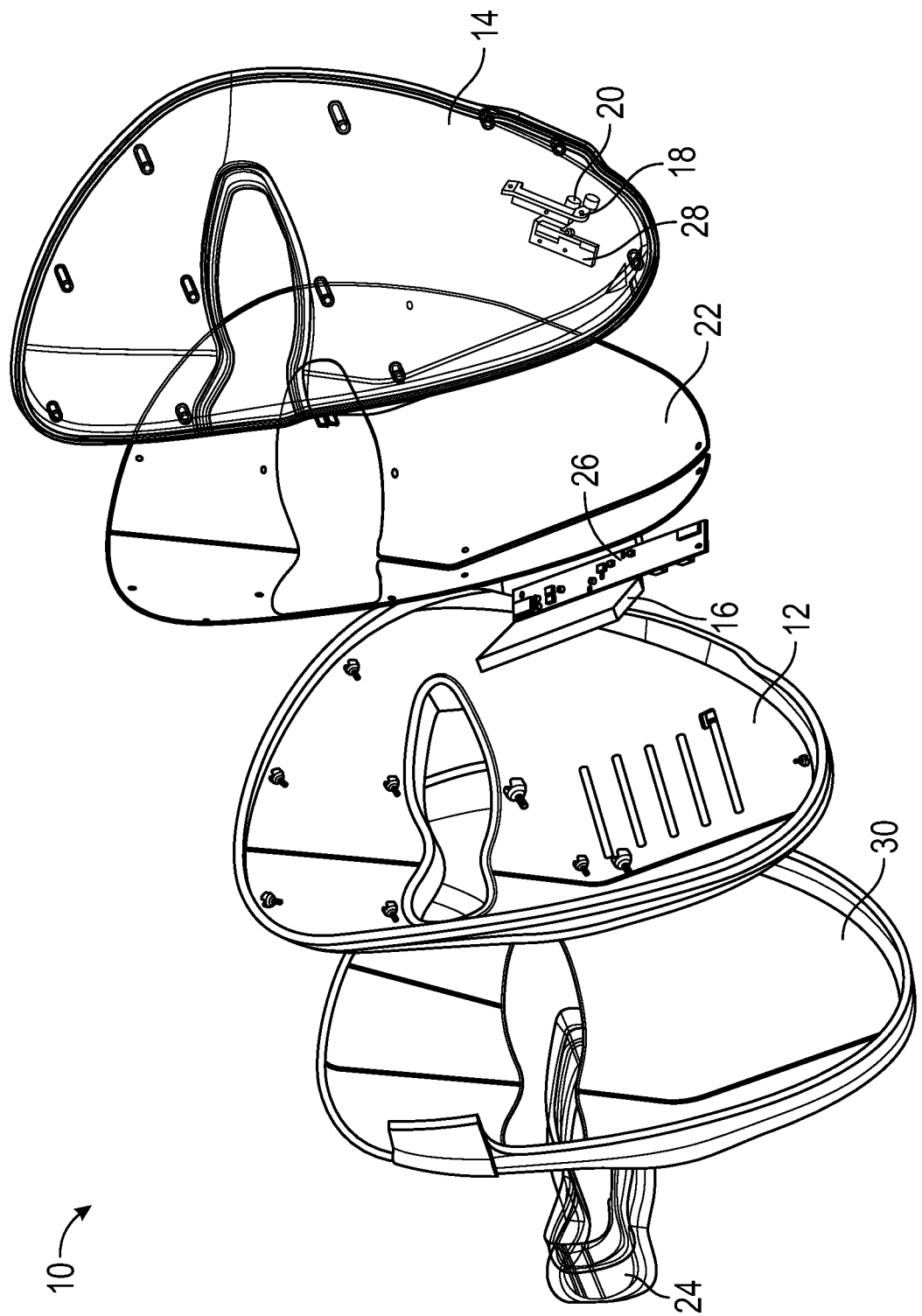
FIG. 2 is a rear, right side, exploded view of a portion of the mask of FIG. 1 for delivering light energy to living skin tissue, the mask having three layers including a face-engaging layer, an intermediate layer, and an exterior layer that carries the substrate covered with the encapsulating material layer with light-emitting sources.
Figure 3A:
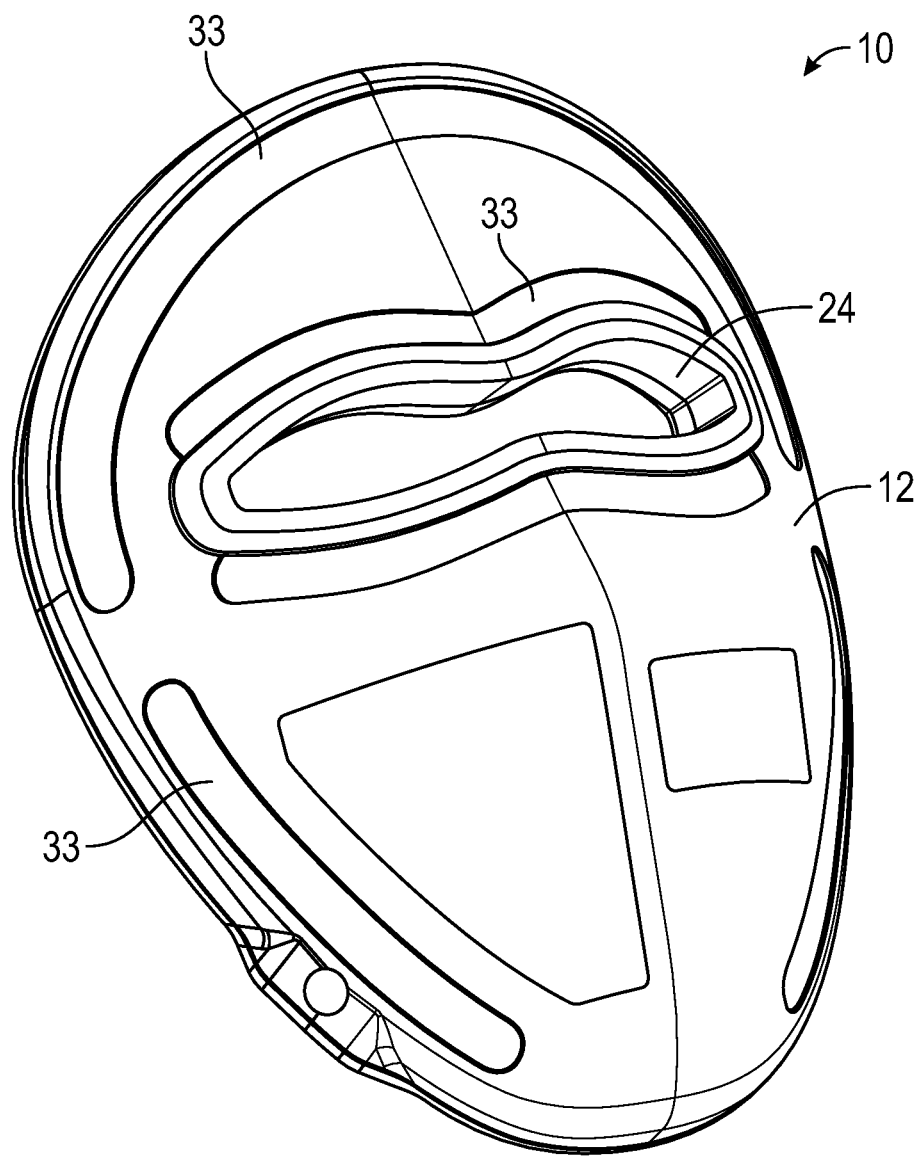
Figure 3C:
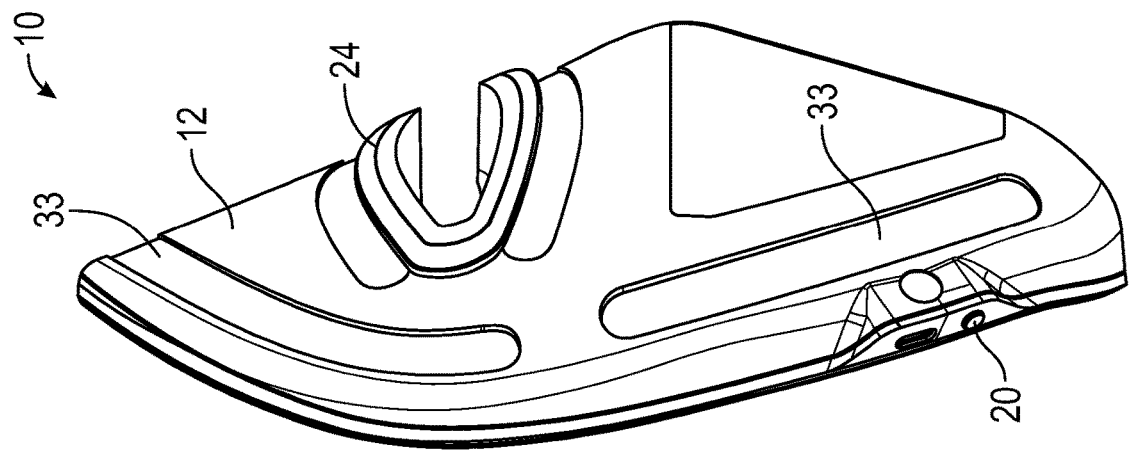
Figure 3B:
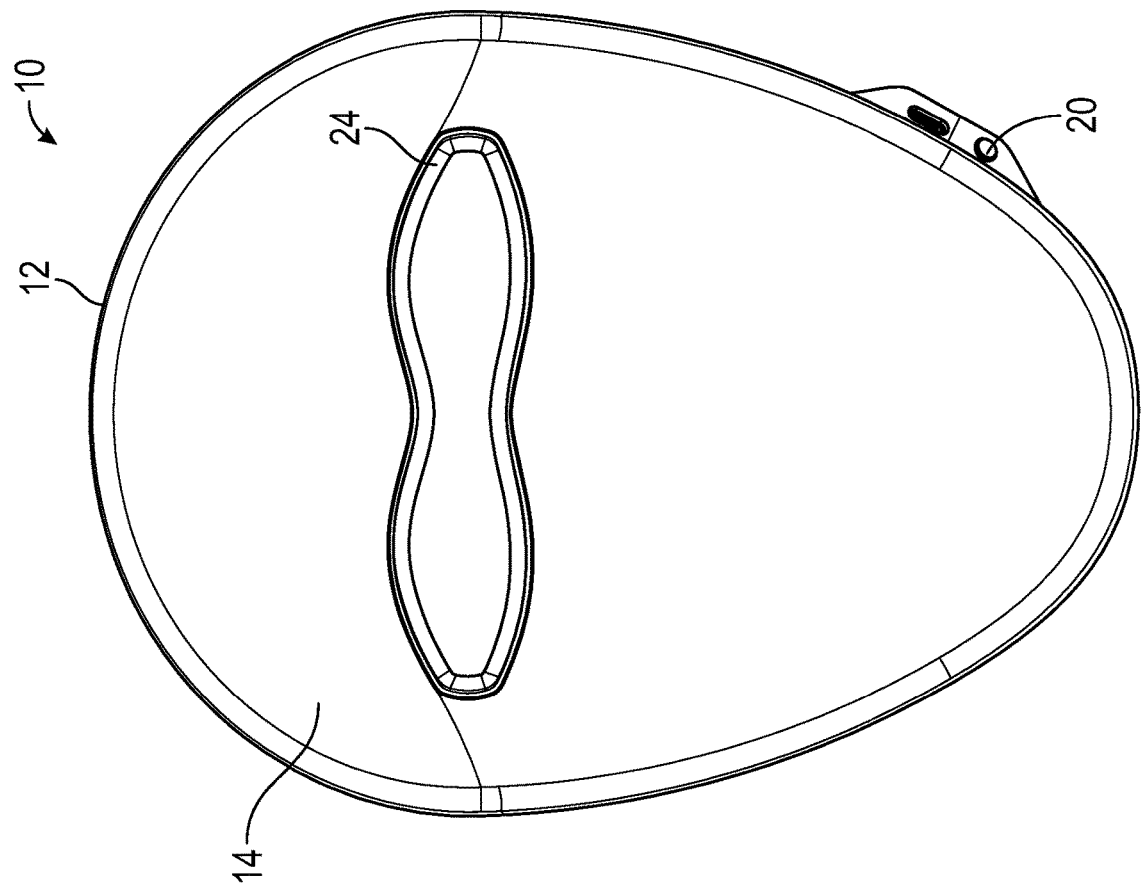
Figure 3F:
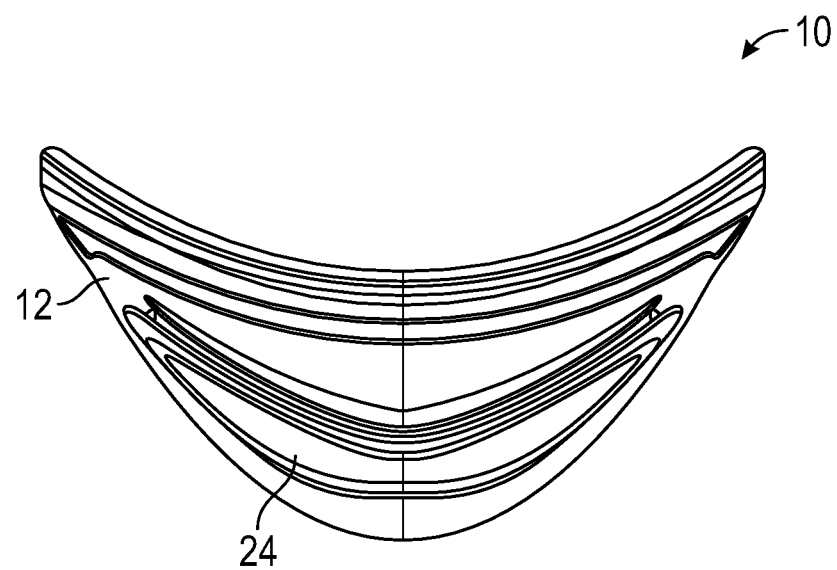
Figure 3G:
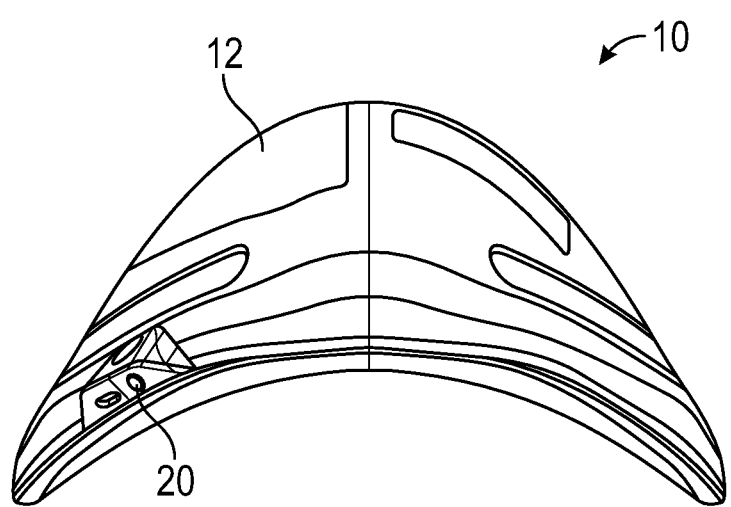
Figure 41:
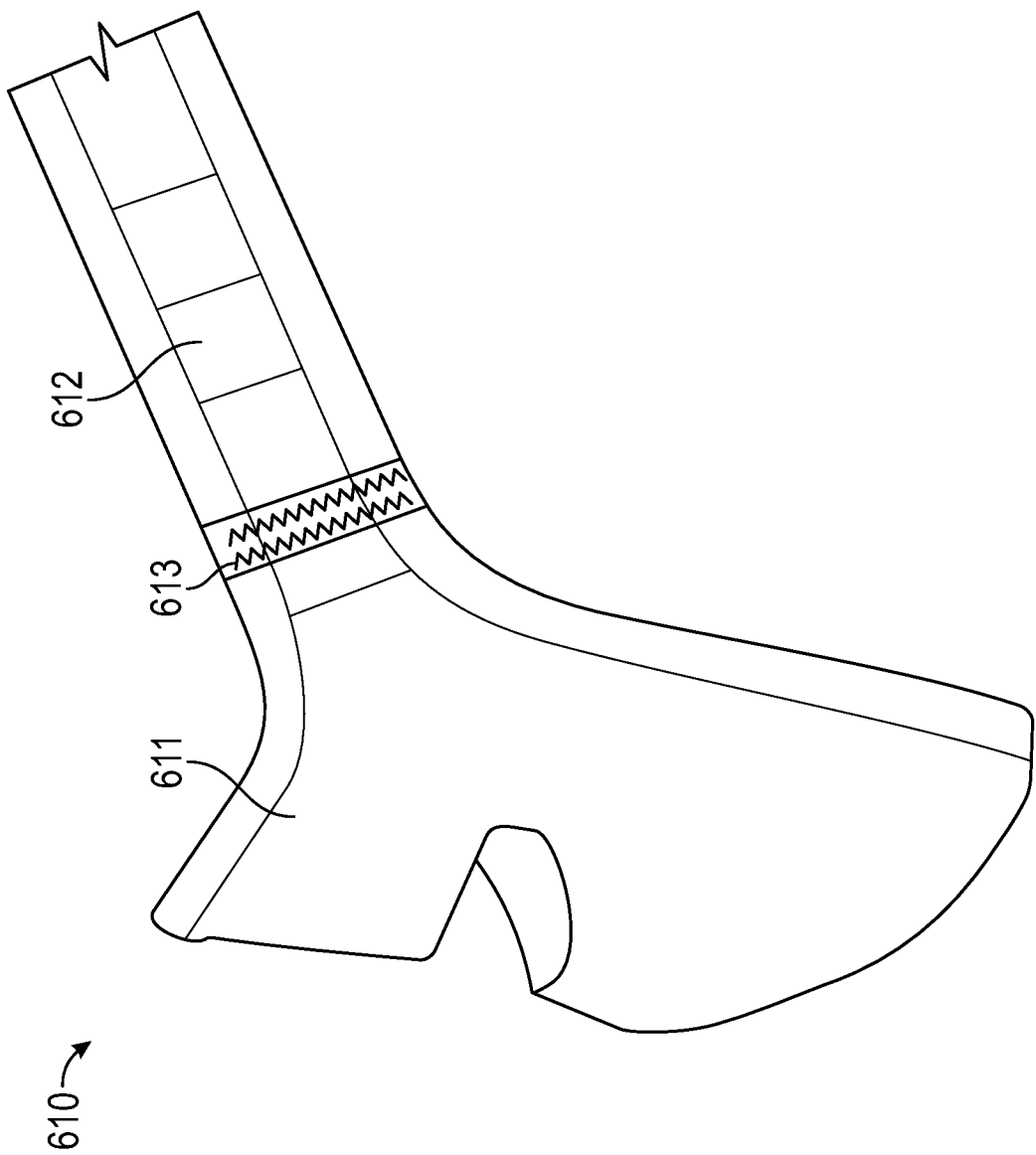

FIG. 41 schematically depicts a face-engaging device for a mask as described in FIGS. 1 and 2 that includes a headband.

Figure 42:
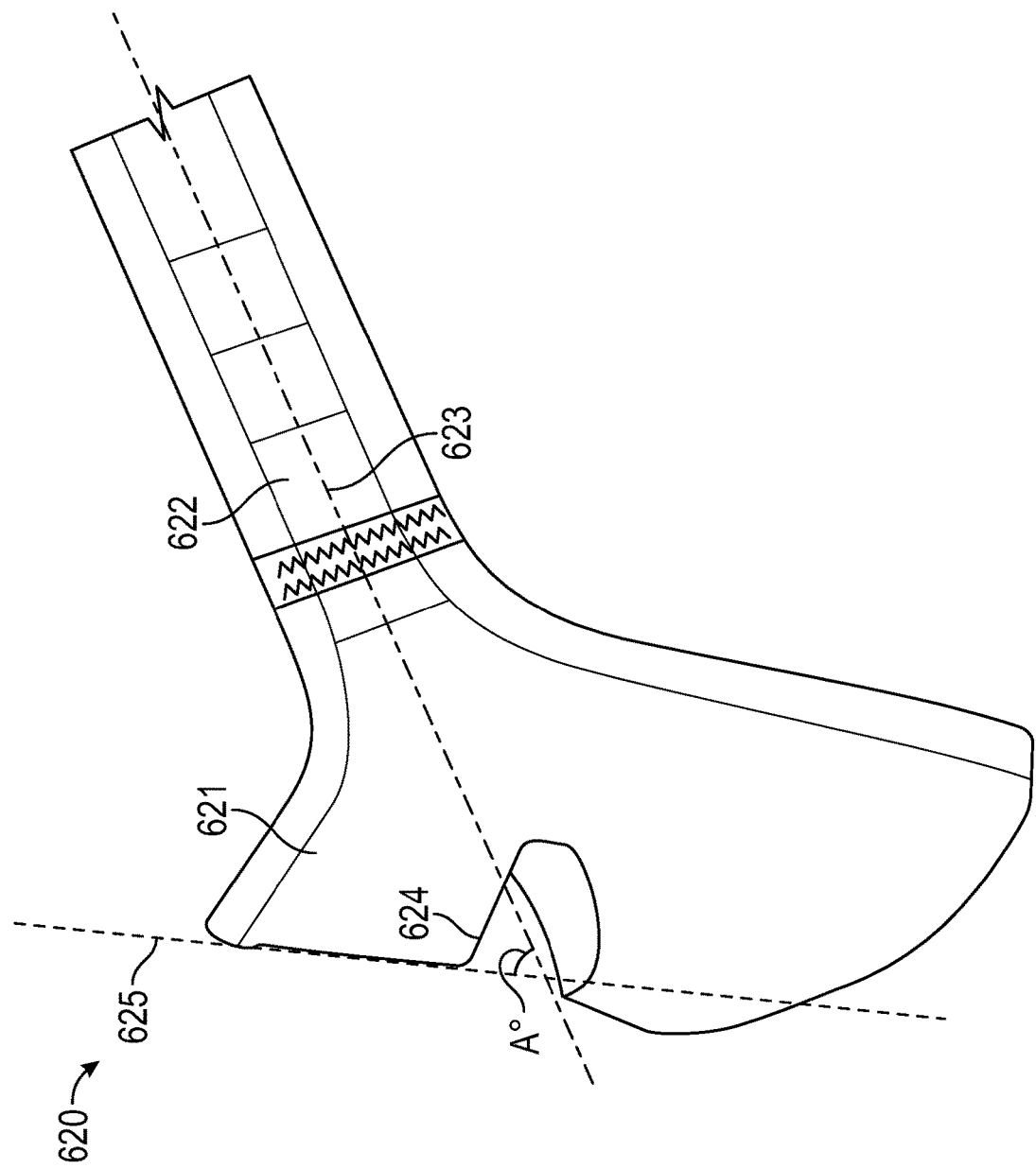

FIG. 42 schematically depicts a face-engaging device that is similar to the device of FIG. 40 and includes superimposed lines showing an angle formed of a headband relative to other portions of the device.

Figure 43:
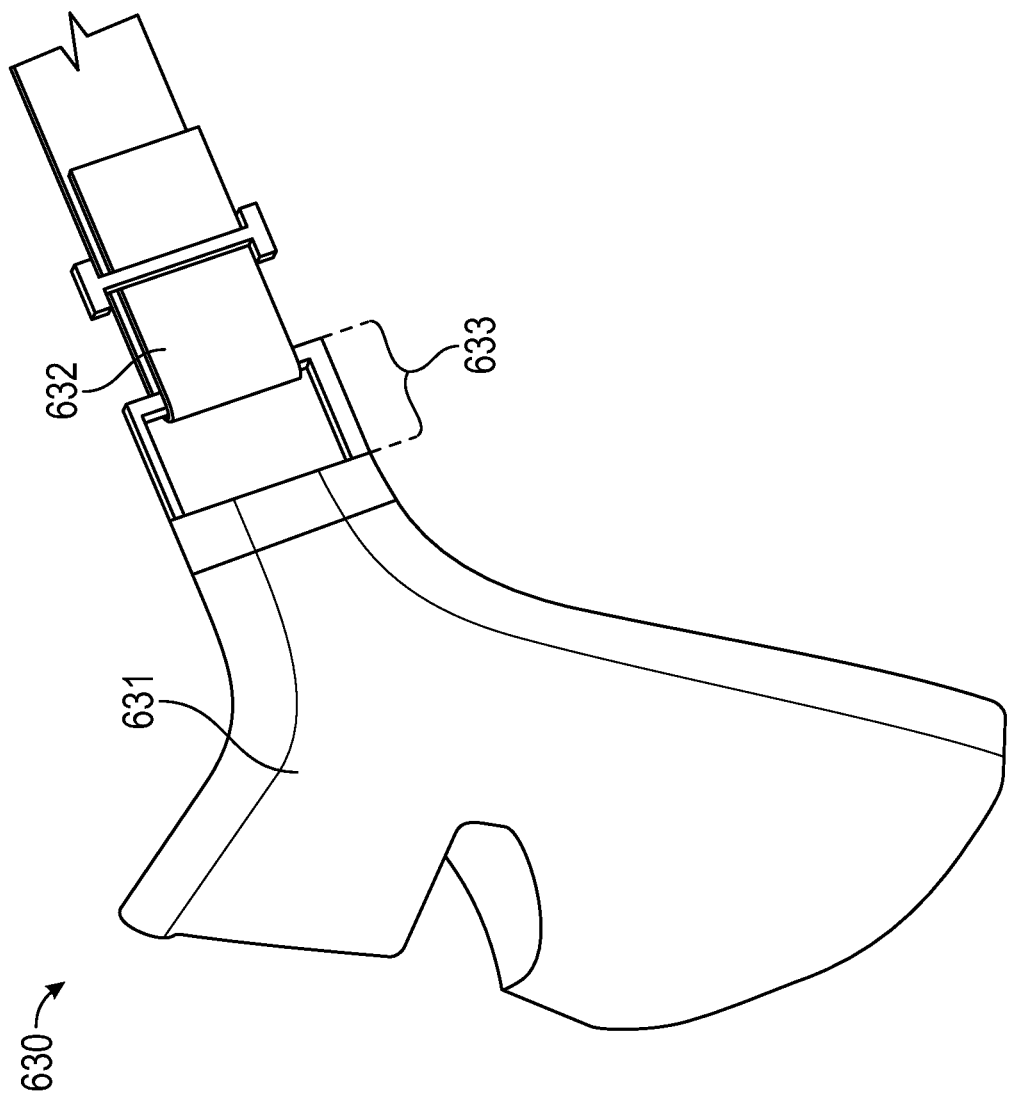

FIG. 43 schematically depicts a face-engaging device for a mask as described in FIGS. 1 and 2 that includes one or more headband engagement features for adjusting the headband.

Figure 44:
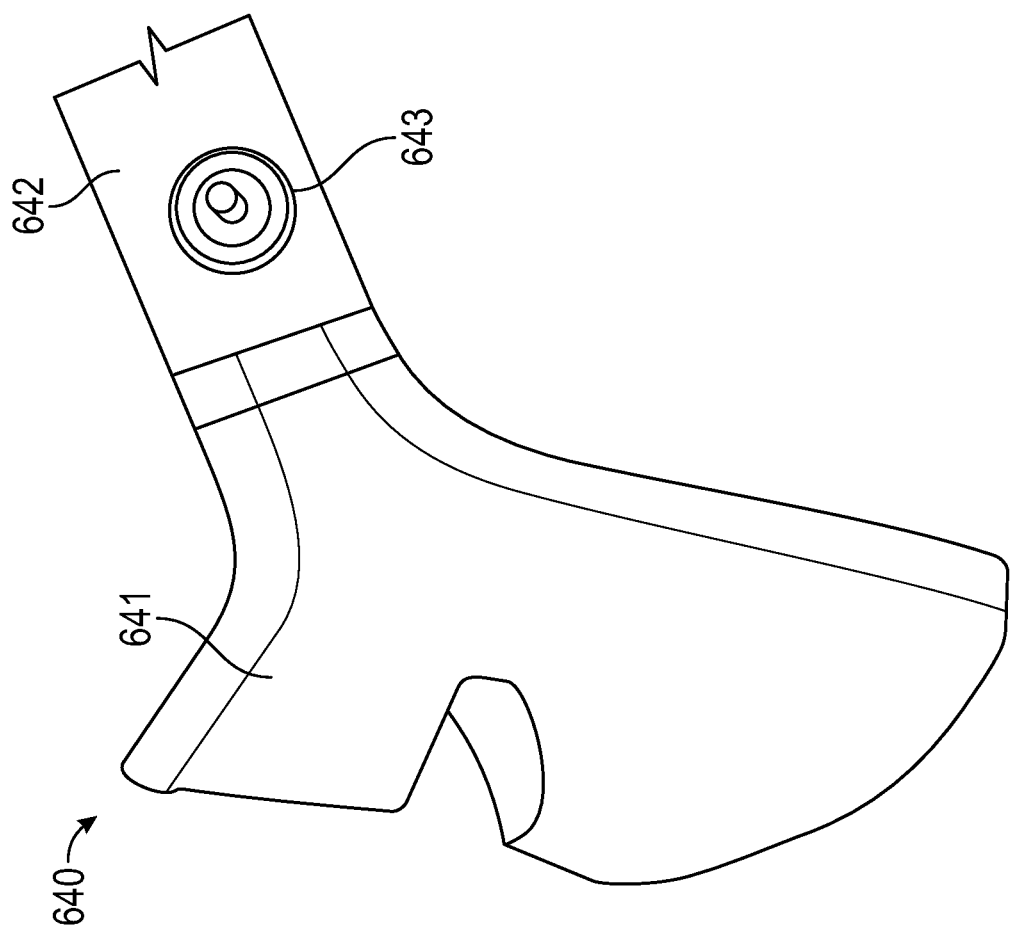

FIG. 44 schematically depicts a face-engaging device for a mask as described in FIGS. 1 and 2 that includes one or more alternative headband engagement features for adjusting the headband.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

Aspects of the present disclosure relate to systems, devices, and related methods for phototherapeutic treatments of skin, and more particularly to phototherapeutic treatments of skin for skin conditioning and/or the treatment of skin wrinkles. Certain aspects relate to phototherapeutic treatment of skin with light of at least two different wavelengths. Light having a first peak wavelength and a first radiant flux may be selected to stimulate enzymatic generation of nitric oxide to increase stores of endogenous nitric oxide or releases endogenous stores of nitric oxide. Light having a second peak wavelength and a second radiant flux may be selected to stimulate collagen production in the skin. Light having a third peak wavelength and a third radiant flux can also be used in conjunction with skin treatment for wrinkles, where the light at the third wavelength and third radiant flux provides an anti-inflammatory effect. Devices are disclosed that include combinations of housings, light-transmissive elements, and flexible substrates that are configured to deliver such light to one or more targeted areas.

Aspects of the disclosure relate to the treatment or conditioning of skin using light having at least two wavelengths. The phrase "treatment of skin" is used herein in the sense of applying light energy with the expectation of a physical response that improves wrinkles in the skin (in comparison to if such light energy were not applied). In particular, the combination of wavelengths may reduce wrinkles in skin (e.g., due to loss of skin collagen in skin tissue), and/or reduce the development of skin wrinkles (e.g., due to loss of skin collagen in skin tissue). The phrase "conditioning of skin" is used in a similar manner but may include a prophylactic aspect, that is, stimulating a change in the skin in anticipation of a need for treatment in order to mitigate or eliminate the need for treatment.

The expression "light" is used herein in accordance with common usage to refer to electromagnetic radiation of any wavelength or any combination of wavelengths, and to refer to one or more photon. Accordingly, the expression "light," as used herein, can refer to visible light or to non-visible light (in particular, ultraviolet (UV) light or infrared light). The expression "light," as used herein, can refer to a single photon of a single wavelength, or it can refer to a plurality of photons that may be of the same wavelength, or one or more photons of each of two or more wavelengths. Accordingly, as an example, the expression "light of wavelength within a range of from about 610 nm to about 630 nm" encompasses, e.g., [i] a single photon of a wavelength in the range of from about 610 nm to about 630 nm, [ii] plural photons of substantially a single wavelength in the range of from about 610 nm to about 630 nm, and [iii] one or more photons of each of a plurality of wavelengths in the range of from about 610 nm to about 630 nm (e.g., a spectrum having a dominant wavelength of 620 nm and a full width at half maximum of 20 nm). The expression "light that comprises at least one wavelength within [a particular range, e.g., about 610 nm to about 630 nm]" encompasses [a] light that consists of photons within the specified wavelength range and [b] light that comprises some photons within the specified wavelength range and some photons outside the specified wavelength range.

The expression "dominant wavelength," is used herein according to its well known and accepted meaning to refer to the perceived color of a spectrum, i.e., the single wavelength of light which produces a color sensation most similar to the color sensation perceived from viewing light emitted by the light source (i.e., it is roughly akin to "hue"), as opposed to "peak wavelength," which is well known to refer to the spectral line with the greatest power in the spectral power distribution of the light source. Because the human eye does not perceive all wavelengths equally (it perceives yellow and green better than red and blue), and because the light emitted by many solid state light emitters (e.g., light-emitting diodes (LEDs)) is actually a range of wavelengths, the color perceived (i.e., the dominant wavelength) is not necessarily equal to (and often differs from) the wavelength with the highest power (peak wavelength). A truly monochromatic light such as a laser has the same dominant and peak wavelengths.

The expression "peak wavelength" is used herein according to its well known and accepted meaning to refer to the wavelength that is of the greatest radiant flux of the light emitted by a light emitter.

The expression "layer," as used herein, refers to a structure of any size, shape and relative dimensions, e.g., a "layer" is not limited in terms of its thickness in relation to other dimensions, or in terms of its uniformity of thickness or any other dimension.

The expression "conform," as used herein, in the context of a first structure conforming to a second structure (e.g., in the expression "the device is configured to conform to at least a portion of a face of a living being"), means that the first structure can be positioned in relation to the second structure such that the contours of the respective structures that are facing each other are similar or analogous. For example, where a first structure can be positioned relative to a second structure such that any concave regions of the first structure are generally facing any convex regions of the second structure, and any convex regions of the second structure are generally facing any concave regions of the second structure, the first and second structures conform to each other. For example, human face masks are designed to conform to human faces. A mask that can be positioned relative to a human face such that at least 80% of the surface area of one major surface of the mask is within 5 cm of the human face "conforms" to the human face.

The expression "major surface" as used herein, means a surface which has a surface area that comprises at least 25% of the surface area of the entire structure, and in some cases at least 40% of the surface area of the entire structure (e.g., a substrate that has a first major surface that conforms to a human face, a second major surface opposite the first major surface, and that is comparatively thin between the first major surface and the second major surface, i.e., the thickness is much smaller than the dimensions of the first and second major surfaces).

The term "engage" (e.g., in an expression that "the first eyepiece is engaged by the substrate" or "a first region of the strap is engaged with the first strap engagement feature") is used herein to refer to any structure and/or any force (e.g., friction) that can hold one element in place (within a range of acceptable movement) relative to another element. "Engage" encompasses where a first element is removably held in place relative to a second element (e.g., by a friction fit, by contact between plastic material having a surface of hooks and fiber material having a surface of loops (such as Velcro®), by a snap, by a removable screw, etc.) and where a first element is non-removably held in place relative to a second element (e.g., by stitching, riveting, etc.).

The expression "removable," as used herein, means that the element that is described as being removable can be removed (e.g., an eyepiece can be removable from a substrate, a strap can be removable from a substrate or a covering element, etc.) without severing any material, e.g., by using a small amount of force (e.g., less than 5 N) to remove an eyepiece from a friction fit in an eyehole of a substrate.

The expression "impinge," as used herein in the context of light impinging on a thing (e.g., in the expression "at least one first solid state light-emitting device configured to impinge light having the first peak wavelength on skin tissue"), means that the light is incident on the thing.

The term "moldable," as used herein, means that the element (or elements) that is/are being described as being moldable can be molded to some degree, i.e., the element's shape can be altered by applying relatively light force (e.g., up to 10 N) and the element will remain in the altered shape (or substantially in the altered shape), or will remain in a shape that differs to some extent from the shape it had prior to being molded.

In some embodiments, treatment of skin and conditioning of skin is performed by applying light of at least two peak wavelengths (each of a respective peak radiant flux) to the skin of interest. Light having a first peak wavelength (and of a first radiant flux, which can be substantially constant or which can be variable, and/or which can be uniform across the treatment area or which can differ in different regions) is applied to the skin in order (1) to stimulate enzymatic generation of nitric oxide to increase endogenous stores of nitric oxide, and/or (2) to stimulate release of nitric oxide from the endogenous stores.

Light having a second peak wavelength (and of a second radiant flux, which can be substantially constant or which can be variable and/or uniform or non-uniform, and which may be the same or different from the first radiant flux) stimulates collagen production. The second peak wavelength differs from the first peak wavelength, and in one aspect, the second peak wavelength is at least 230 nm greater than the first peak wavelength. Light from a third peak wavelength (and of a third radiant flux) may be applied to reduce inflammation.

As indicated above, some embodiments of the present disclosure comprise stimulating, by photo-production, endogenous stores of nitric oxide ("NO") in the skin, effectively regenerating "gaseous" (or unbound) nitric oxide that is auto-oxidized into nitrosative intermediates and bound covalently in the body in the "bound" state. By stimulating release of nitric oxide from endogenous stores to a gaseous state, the gaseous nitric oxide may be maintained for an extended time in an expanded spatial zone and serve as a source of chemical energy for body processes.

As noted previously, nitric oxide is endogenously stored on a variety of nitrosated biochemical structures. Upon receiving the required excitation energy from the photon radiation, both nitroso and nitrosyl compounds undergo hemolytic cleavage of S—N, N—N, or M-N bonds to yield free radical nitric oxide. Nitrosothiols and nitrosamines are photoactive and can be triggered to release nitric oxide by wavelength specific excitation.

The effect of light at certain wavelengths in the production and/or release of nitric oxide is described in U.S. Pat. No. 10,525,275, the contents of which are hereby incorporated in their entirety by reference.

It has been reported that NO may diffuse in mammalian skin tissue (hereinafter, "skin tissue" for convenience) by a distance of up to about 500 microns. In certain embodiments, photons of a first energy hv1 may be supplied to skin tissue to stimulate enzymatic generation of NO to increase endogenous stores of NO in a first diffusion zone. Photons of a second energy hv2 may be supplied to skin tissue in a region within or overlapping the first diffusion zone to trigger release of NO from endogenous stores, thereby creating a second diffusion zone. Alternatively, or additionally, photons of a second energy hv2 may be supplied to stimulate enzymatic generation of NO to increase endogenous stores of NO in the second diffusion zone. Photons of a third energy hv3 may be supplied to skin tissue in a region within or overlapping the second diffusion zone to trigger release of endogenous stores of NO, thereby creating a third diffusion zone. Alternatively, or additionally, photons of a third energy hv3 may be supplied to stimulate enzymatic generation of NO to increase endogenous stores of NO in the third diffusion zone. In certain embodiments, the first, second, and third diffusion zones may have different average depths relative to an outer epidermal surface. In certain embodiments, the first photon energy hv1, the second photon energy hv2, and the third photon energy hv3 may be supplied at different peak wavelengths, wherein different peak wavelengths may penetrate skin to different depths— since longer wavelengths typically provide greater penetration depth. In certain embodiments, sequential or simultaneous impingement of increasing wavelengths of light may serve to "push" a nitric oxide diffusion zone deeper within skin tissue than might otherwise be obtained by using a single (e.g., long) wavelength of light.

Light having a first peak wavelength and a first radiant flux that stimulates enzymatic generation of nitric oxide to increase endogenous stores of nitric oxide may be referred to herein as "endogenous stores increasing light" or "ES increasing light." Light having a first peak wavelength and a first radiant flux to release nitric oxide from the endogenous stores may be referred to herein as "endogenous store releasing light" or "ES releasing light."

In another aspect, light of a different wavelength is applied to the skin to stimulate collagen production. Nitric oxide promotes increased vasculature, which supports the produced collagen.

In certain embodiments, light of at least three peak wavelengths is used, including one peak wavelength to provide an anti-inflammatory effect, in combination with a peak wavelength of ES releasing light, and a peak wavelength of ES increasing light to stimulate collagen production.

In certain embodiments, each of the collagen-stimulating and ES increasing light and/or ES releasing light has a radiant flux in a range of at least 1 milliwatt per square centimeter ($mW/cm^2$), or at least 4 $mW/cm^2$, or at least 10 $mW/cm^2$, or at least 15 $mW/cm^2$, or at least 20 $mW/cm^2$, or at least 30 $mW/cm^2$, or at least 40 $mW/cm^2$, or at least 50 $mW/cm^2$, or in a range of from 4 $mW/cm^2$ to 60 $mW/cm^2$, or in a range of from 4 $mW/cm^2$ to 30 $mW/cm^2$, or in a range of from 4 $mW/cm^2$ to 20 $mW/cm^2$, or in a range of from 4 $mW/cm^2$ to 10 $mW/cm^2$, or in a range of from 10 $mW/cm^2$ to 60 $mW/cm^2$, or in a range of from 20 $mW/cm^2$ to 60 $mW/cm^2$, or in a range of from 30 $mW/cm^2$ to 60 $mW/cm^2$, or in a range of from 40 $mW/cm^2$ to 60 $mW/cm^2$, or in another range specified herein.

In certain embodiments, the ES increasing and/or ES releasing light has a greater radiant flux than the collagen-stimulating light. In certain embodiments, the collagen-producing light has a greater radiant flux than the ES increasing and/or ES releasing light.

In certain embodiments, skin tissue is impinged with light of radiant exposure in the range of from about 0.3 joules per square centimeter ($J/cm^2$) to about 30 $J/cm^2$ (e.g., 4.5 $mW/cm^2$ for 10 minutes, or 1 $mW/cm^2$ for 45 minutes, or 0.1 $mW/cm^2$ for 450 minutes, etc.). In certain embodiments, skin tissue is impinged with light of radiant exposure in the range of from about 1.0 $J/cm^2$ to about 10 $J/cm^2$. In certain embodiments, skin tissue is impinged with light of radiant exposure in the range of from about 1.0 $J/cm^2$ to about 5 $J/cm^2$. In certain embodiments, skin tissue is impinged with light of radiant exposure of about 3.0 $J/cm^2$.

In certain embodiments, one or both of the collagen-producing light and ES increasing and/or ES releasing light has a radiant flux profile that is substantially constant during a treatment window. In certain embodiments, at least one of the collagen-producing light and ES increasing and/or ES releasing light has a radiant flux profile that increases with time during a treatment window.

In certain embodiments, at least one of the collagen-producing light and ES increasing and/or ES releasing light has a radiant flux profile that decreases with time during a treatment window. In certain embodiments, one of the collagen-producing light and ES increasing and/or ES releasing light has a radiant flux profile that decreases with time during a treatment window, while the other of the collagen-producing light and ES increasing and/or ES releasing light has a radiant flux profile that increases with time during a treatment window.

In certain embodiments, ES increasing and/or ES releasing light is applied to skin tissue during a first time window, and collagen-producing light is applied to skin tissue during a second time window, and the second time window overlaps with the first time window. In other embodiments, ES increasing and/or ES releasing light is applied to skin tissue during a first time window, collagen-producing light is applied to skin tissue during a second time window, and the second time is non-overlapping with the first time window. In certain embodiments, the second time window is initiated more than one minute, more than 5 minutes, more than 10 minutes, more than 30 minutes, or more than one hour after conclusion of the first time window. In certain embodiments, ES increasing and/or releasing light is applied to skin tissue during a first time window, collagen-producing light is applied to skin tissue during a second time window, and the first time window and the second time window are substantially the same. In other embodiments, the second time window is longer than the first time window.

In certain embodiments, one or both of the collagen-producing light and ES increasing light and/or ES releasing light may be provided by a steady state source providing a radiant flux that is substantially constant over a prolonged period without being pulsed.

In certain embodiments, one or both of collagen-producing light and ES increasing light and/or ES releasing light may include more than one discrete pulse of light. In certain embodiments, more than one discrete pulse of ES increasing and/or ES releasing light is impinged on skin tissue during a first time window, and/or more than one discrete pulse of collagen-producing light is impinged on skin tissue during a second time window. In certain embodiments, the first time window and the second time window may be coextensive, may be overlapping but not coextensive, or may be non-overlapping.

In certain embodiments, at least one of radiant flux and pulse duration of ES increasing and/or ES releasing light may be reduced from a maximum value to a non-zero reduced value during a portion of a first time window. In certain embodiments, at least one of radiant flux and pulse duration of ES increasing and/or ES releasing light may be increased from a non-zero value to a higher value during a portion of a first time window. In certain embodiments, at least one of radiant flux and pulse duration of collagen-producing light may be reduced from a maximum value to a non-zero reduced value during a portion of a second time window. In certain embodiments, at least one of radiant flux and pulse duration of collagen-producing light may be increased from a non-zero value to a higher value during a portion of a second time window.

In certain embodiments, each of ES increasing and/or ES releasing light and the collagen-producing light consist of non-coherent light. In certain embodiments, each of the collagen-producing light and the ES increasing light and/or ES releasing light consist of coherent light. In certain embodiments, one of the collagen-producing light and the ES increasing light and/or the ES releasing light consists of non-coherent light, and the other consists of coherent light. In some embodiments, some of the ES increasing light is coherent and some of the ES increasing light is non-coherent, and/or some of the ES releasing light is coherent and some of the ES releasing light is non-coherent.

In certain embodiments, the ES increasing and/or ES releasing light is provided by at least one first light-emitting device and the collagen-producing light is provided by at least one second light-emitting device. In certain embodiments, the ES increasing and/or ES releasing light is provided by a first array of light-emitting devices and the collagen-producing light is provided by a second array of light-emitting devices.

In certain embodiments, at least one of the ES increasing and/or ES releasing light and the collagen-producing light is provided by at least one solid state light-emitting device. Examples of solid state light-emitting devices include (but are not limited to) LEDs, lasers, thin film electroluminescent devices, powdered electroluminescent devices, field induced polymer electroluminescent devices, and polymer light-emitting electrochemical cells. In certain embodiments, the ES increasing and/or ES releasing light is provided by at least one first solid state light-emitting device and the collagen-producing light is provided by at least one second solid state light-emitting device. In certain embodiments, the collagen-producing and the ES increasing light and/or ES releasing light may be generated by different emitters contained in a single solid state emitter package, wherein close spacing between adjacent emitters may provide integral color mixing. In certain embodiments, the collagen-producing light may be provided by a first array of solid state light-emitting devices and the ES increasing and/or ES releasing light may be provided by a second array of solid state light-emitting devices. In certain embodiments, an array of solid state emitter packages each including at least one first emitter and at least one second emitter may be provided, wherein the array of solid state emitter packages embodies a first array of solid state emitters arranged to generate ES increasing and/or ES releasing light and embodies a second array of solid state emitters arranged to generate collagen-producing light. In certain embodiments, an array of solid state emitter packages may embody packages further including third, fourth, and/or fifth solid state emitters, such that a single array of solid state emitter packages may embody three, four, or five arrays of solid state emitters, wherein each array is arranged to generate emissions with respective different peak wavelengths.

In certain embodiments, at least one of collagen-producing light and the ES increasing and/or ES releasing light is provided by at least one light-emitting device devoid of a wavelength conversion material. In other embodiments, at least one of the collagen-producing light and the ES increasing and/or the ES releasing light is provided by at least one light-emitting device arranged to stimulate a wavelength conversion material, such as a phosphor material, a fluorescent dye material, a quantum dot material, and/or a fluorophore material.

In certain embodiments, the collagen-producing light consists of substantially monochromatic light and the ES increasing and/or ES releasing light consists of substantially monochromatic light. In certain embodiments, the ES increasing and/or ES releasing light includes a first spectral output having a first full width at half maximum value of less than 25 nm (or less than 20 nm, or less than 15 nm, or in a range of from 5 nm to 25 nm, or in a range of from 10 nm to 25 nm, or in a range of from 15 nm to 25 nm).

In certain embodiments, the collagen-producing light is produced by one or more second light emitters having a single second peak wavelength, and the ES increasing and/or ES releasing light is produced by one or more first light emitters having a single first peak wavelength. In other embodiments, the collagen-producing light may be produced by at least two light emitters having different peak wavelengths (e.g., differing by at least 5 nm, at least 10 nm, at least 15 nm, at least 20 nm, or at least 25 nm), and/or the ES increasing and/or ES releasing light may be produced by at least two light emitters having different peak wavelengths (e.g., differing by at least 5 nm, at least 10 nm, at least 15 nm, at least 20 nm, or at least 25 nm).

UV light (e.g., UV-A light having a peak wavelength in a range of from 315 nm to 400 nm, and UV-B light having a peak wavelength in a range of from 280 nm to 315 nm, and UV-C light having a peak wavelength in a range from 200 nm to 280 nm) may be effective as ES increasing light; however, overexposure to UV light may lead to detrimental health effects including premature skin aging and potentially elevated risk for certain types of cancer. It may therefore be desirable to use shorter cycles and/or lower doses of UV light than corresponding treatments with only visible light. In certain embodiments, the combination of light at this wavelength with anti-inflammatory light at a third wavelength and a third radiant flux may reduce these effects.

In certain embodiments, UV light (e.g., having peak wavelengths in a range of from 320 nm to 399 nm) may be used as ES increasing light; however, in other embodiments, UV light may be avoided.

In certain embodiments, ES increasing and/or ES releasing light is substantially free of UV light. In certain embodiments, less than 5% of the ES increasing light is in a wavelength range of less than 400 nm, and less than 1% of the ES releasing light is in a wavelength range of less than 400 nm. In certain embodiments, ES increasing light includes a peak wavelength in a range of from 400 nm to 490 nm, or from 400 nm to 450 nm, or from 400 nm to 435 nm, or from 400 nm to 420 nm.

In certain embodiments, ES increasing light includes a peak wavelength in a range of from 400 nm to 490 nm, or from 400 nm to 450 nm, or from 400 nm to 435 nm, or from 400 nm to 420 nm.

In certain embodiments, ES increasing light may include a wavelength range and flux that may alter the presence, concentration, or growth of bacteria or other microbes in or on living skin tissue receiving the light. Light (e.g., having peak wavelengths from 400 nm to 435 nm, or more preferably from 400 nm to 420 nm) in particular may affect microbial growth.

Effects on microbial growth may depend on the wavelength range and dose. In certain embodiments, ES increasing light may include light having a peak wavelength in a range of from 400 nm to 420 nm to provide a bacteriostatic effect (e.g., with pulsed light having a radiant flux of <9 mW/cm$^2$), provide a bactericidal effect (e.g., with substantially steady state light having a radiant flux in a range of from 1 mW/cm$^2$ to 17 mW/cm$^2$), or provide an antimicrobial effect (e.g., with substantially steady state light having a radiant flux in a range of greater than 1 mW/cm$^2$, such as in a range of from 1 mW/cm$^2$ to 60 mW/cm$^2$).

In certain embodiments, ES increasing light in a near-UV range (e.g., from 400 nm to 420 nm) may also affect microbial growth (whether in a bacteriostatic range, bactericidal range, or an antimicrobial range). Such function(s) may be in addition to the function of the ES increasing light to increase endogenous stores of nitric oxide in living skin tissue.

In certain embodiments, ES releasing light may include a peak wavelength in a range of from 500 nm to 900 nm, or in a range of from 490 nm to 570 nm, or in a range of from 510 nm to 550 nm, or in a range of from 520 nm to 540 nm, or in a range of from 525 nm to 535 nm, or in a range of from 528 nm to 532 nm, or in a range of about 530 nm.

As shown in U.S. Pat. No. 10,525,275, the wavelengths identified to be most effective in releasing NO from Hb-NO were determined to be the following, from best to worst: 530 nm, 505 nm, 597 nm, 447 nm, 850 nm, 470 nm, 410 nm, 630 nm, and 850 nm. In certain aspects, wavelengths at 530 nm, 597 nm, 505 nm, 850 nm, 470 nm, 630 nm, 410 nm, 447 nm, and 850 nm demonstrate released nitric oxide from CCO-NO. Notably, 530 nm was determined to be a particularly effective peak wavelength of light for releasing NO from both Hb-NO and CCO-NO. In certain aspects, the wavelength at 850 nm, or wavelength ranges that are inclusive of 850 nm, may promote collagen growth, while also providing anti-inflammatory response and NO releases.

A combination of 410 nm light and 530 nm light, including equal parts among other combinations, may be equally as effective as 530 nm light alone. Such a combination may be beneficial since a 410 nm blue LED may be significantly more efficient than a 530 nm green LED, such that a combination of equal parts of 410 nm LED emissions and 530 nm LED emissions may use 26% less electric power than emissions of a 530 nm LED alone, when operated to provide the same radiant flux.

Light at 850 nm may be significantly less effective than the 530 nm green light at releasing NO from Hb-NO, but may be effective at promoting collagen growth. The release of NO from Hb-NO appears to be the same for 530 nm green light, 850 nm red light, and a combination of 530 nm green and 850 nm red light for the time window of from 0 seconds to about 2000 seconds, but the effectiveness of the different sources diverges thereafter. Without intending to be bound by any particular theory or explanation of this phenomenon, it is suggested that NO binds to Hb-NO at multiple sites, and that removal of a second or subsequent NO molecule from Hb-NO may require more energy than removal of a first NO molecule, perhaps due to a change in shape of the Hb-NO after removal of a first NO molecule.

In certain embodiments, collagen-producing light having a first peak wavelength is impinged on living skin tissue, and ES increasing or ES releasing light that includes light having a second peak wavelength is impinged on the living skin tissue, and furthermore a light having a third peak wavelength (i.e., anti-inflammatory light) may be impinged on the living skin tissue. In certain embodiments, the light having a third peak wavelength may be provided at substantially the same time as (or during a time window overlapping at least one time window of) one or both of the collagen-producing light and the ES increasing and/or ES releasing light.

In certain embodiments, the light having a third peak wavelength differs from each of the first peak wavelength and the second peak wavelength by at least 10 nm. In certain embodiments, the light having a third peak wavelength exceeds the second peak wavelength by at least 20 nm. In certain embodiments, the light having a third peak wavelength is provided with a radiant flux in a range of from 1 mW/cm$^2$ to 60 mW/cm$^2$. In certain embodiments, the third peak wavelength is in a range of from 600 nm to 900 nm, or in a range of from 600 nm to 700 nm.

In certain embodiments, the anti-inflammatory light at the third wavelength is in a range of from about 630 nm to 670 nm (e.g., including specific wavelengths of about 630 nm and about 660 nm), and may be useful to provide anti-inflammatory effects and/or to promote vasodilation.

In addition to various sources of light described above, the principles of the present disclosure may also include one or more other types of directed energy sources. As used herein, a directed energy source may include any of the various light sources previously described, and/or an energy source capable of providing one or more of heat, infrared heating, resistance heating, radio waves, microwaves, soundwaves, ultrasound waves, electromagnetic interference, and electromagnetic radiation that may be directed to a target body tissue. Combinations of visual and non-visual electromagnetic radiation may include peak wavelengths in a range from 180 nm to 4000 nm. Illumination devices as disclosed herein may include a light source and another directed energy source capable of providing directed energy beyond visible and UV light. In other embodiments, the other directed energy source capable of providing directed energy beyond visible and UV light may be provided separately from illumination devices of the present disclosure.

The methods and devices disclosed herein for treating wrinkles in living skin tissue are contemplated for use with a wide variety of skin tissues. In certain embodiments, skin tissue comprises epithelial skin tissue, which, in some aspects, is skin tissue of the scalp.

Some patients have wrinkled skin on their face, neck and/or scalp. Representative types of wrinkled skin in these areas include crows-feet, forehead lines, frown lines, brow droop, tear troughs, bunny lines, nasolabial folds, marionette lines/jowls, vertical lip lines, mouth frown, mental crease, wrinkles on the neck, wrinkles on the forehead, wrinkles between eyebrows, and wrinkles under the eyes.

Wrinkles also appear elsewhere, including but not limited to forearms, underarms, thighs, feet, knees, elbows, and buttocks, sometimes in the form of crepey or saggy skin.

The combination of wavelengths described herein can be administered to wrinkled skin of any type, including the types listed above, for a duration and at a radiant flux sufficient to treat the disorder.

The type of device used to administer the light may depend on the location of the skin to be treated. For example, a helmet can be used to treat wrinkles on the scalp, and a mask or skin plaster can be used to treat wrinkles on the face. Flexible bandages that include LEDs or lasers can be applied to skin elsewhere on the body. Wands can also be used to apply light to the skin. Enclosures can be used, where the hands or feet are to be treated. These devices are discussed in more detail below.

Various devices may be used to deliver light at collagen-promoting and ES increasing and/or ES releasing wavelengths, so long as the appropriate wavelengths of light can be delivered at an appropriate flux, and for an appropriate time, to treat wrinkles.

In some embodiments, the devices will be in the form of a flexible substrate equipped with the ability to emit light at the desired wavelengths.

In some embodiments, the devices will be in the form of helmets, masks or skin plasters. In still other embodiments, the devices will be in the form of conforming or conformable appliances.

In some embodiments, particularly when the devices are used to condition skin of the scalp, the devices can be in the form of a helmet, cap, or other device adapted for applying light to the scalp.

In certain aspects, a device for reconditioning skin as disclosed herein may include a flexible substrate supporting one or more light-emitting elements that may be arranged to conform to at least a portion of a human body. In certain embodiments, a flexible substrate may include a flexible printed circuit board (PCB), and may include at least one polyimide-containing layer and at least one layer of copper or another electrically conductive material.

In other embodiments, a device for reconditioning skin, for example, by reducing wrinkles, as disclosed herein may include a rigid substrate supporting one or more light-emitting elements. In certain embodiments, one or more surfaces of a device for conditioning skin may include a light-transmissive encapsulating material arranged to cover a light emitter(s) and at least a portion of an associated substrate (e.g., flexible PCB). A preferred encapsulating material is silicone, which may be applied by any suitable means such as molding, dipping, spraying, dispensing, or the like. In certain embodiments, one or more functional materials may be added to or coated on an encapsulating material. In certain embodiments, at least one surface, or substantially all surfaces (e.g., front and back surfaces) of a flexible PCB may be covered with encapsulating material.

In certain embodiments, a substrate as described herein may be arranged to support one or more light-emitting elements. In certain embodiments, one or more light-emitting elements may include multi-emitting light-emitting devices such as multi-LED packages. In certain embodiments, one or more light-emitting elements may be arranged for direct illumination, wherein at least a portion of emissions generated by the light-emitting element is arranged to be transmitted directly through a light-transmissive external surface of a device without need for an intervening waveguide or reflector. In certain embodiments, one or more light-emitting elements may be arranged for indirect illumination (e.g., side illumination), wherein emissions generated by the light-emitting element are arranged to be transmitted to a light-transmissive external surface via a waveguide and/or a reflector, without a light-emitting element being in direct line-of-sight arrangement relative to a light-transmissive external surface. In certain embodiments, a hybrid configuration may be employed, including one or more light-emitting elements arranged for direct illumination, and further including one or more light-emitting elements arranged for indirect illumination. In certain embodiments, one or more reflective materials (e.g., reflective flexible PCB or other reflective films) may be provided along selected surfaces of a device to reduce internal absorption of light and to direct light emissions toward an intended light-transmissive surface. In certain embodiments, a flexible light-emitting device may include a substantially uniform thickness. In other embodiments, a flexible light-emitting device may include a thickness that varies with position, such as a thickness that tapers in one direction or multiple directions. In certain embodiments, presence of a tapered thickness may help a flexible light-emitting device to more easily be wrapped against or to conform to areas of a mammalian (e.g., human) body.

In certain embodiments, one or multiple holes or perforations may be formed in a substrate and any associated encapsulating material. In certain embodiments, holes may be formed to permit transit of air, such as may be useful for thermal management. In certain embodiments, one or more holes may be arranged to permit sensing of at least one condition through the hole(s). Holes may be made by any suitable means such as laser perforation, die pressing, slitting, punching, blade cutting, and roller perforation. In certain embodiments, holes may have uniform or non-uniform size, placement, and/or distribution relative to a substrate and encapsulating material.

In certain embodiments, a device for treating wrinkles as disclosed herein may include one or more light-affecting elements such as one or more light extraction features, wavelength conversion materials, light diffusion or scattering materials, and/or light diffusion or scattering features. In certain embodiments, one or more light-affecting elements may be arranged in a layer between a light-emitting element and a light-transmissive surface of a device. In certain embodiments, an encapsulating material (e.g., encapsulating material layer) may be arranged between at least one light-emitting element and one or more light-affecting elements. In certain embodiments, one or more light-affecting elements may be formed or dispersed within an encapsulating material.

In certain embodiments, impingement of light on living skin tissue and/or operation of a device as disclosed herein may be responsive to one or more signals generated by one or more sensors or other elements. Various types of sensors are contemplated, including temperature sensors, photosensors, image sensors, proximity sensors, pressure sensors, chemical sensors, biosensors, accelerometers, moisture sensors, oximeters, current sensors, voltage sensors, and the like. Other elements that may affect impingement of light and/or operation of a device as disclosed herein include a timer, a cycle counter, a manually operated control element, a wireless transmitter and/or receiver (as may be embodied in a transceiver), a laptop or tablet computer, a mobile phone, or another portable digital device. Wired and/or wireless communication between a device as disclosed herein and one or more signal generating or signal receiving elements may be provided.

In certain embodiments, impingement of light on living skin tissue and/or operation of a device as disclosed herein may be responsive to one or more temperature signals. For example, a temperature condition may be sensed on or proximate to (a) a device arranged to emit collagen-producing and/or ES generating/ES releasing light or (b) skin tissue; at least one signal indicative of the temperature condition may be generated; and operation of a lighting device may be controlled responsive to the at least one signal. Such control may include initiation of operation, deviation (or alteration) of operation, or termination of operation of light-emitting elements, such as elements arranged to emit collagen-promoting and ES generating light and/or ES releasing light. In certain embodiments, thermal foldback protection may be provided at a threshold temperature (e.g., >42° Celsius) to prevent a user from experiencing burns or discomfort. In certain embodiments, thermal foldback protection may trigger a light-emitting device to terminate operation, reduce current, or change an operating state in response to receipt of a signal indicating an excess temperature condition.

In certain embodiments, a device for treating wrinkles, as disclosed herein, may include one or more sensors. In certain embodiments, one or more light emitters and photodiodes may be provided to illuminate the skin with one or more selected wavelengths to detect blood flow in or proximate to the skin to be treated. One sensor or multiple sensors may be provided.

In certain embodiments, a device for treating wrinkles as disclosed herein may include a memory element to store information indicative of one or more sensor signals. Such information may be used for diagnosis, assessing patient compliance, assessing patient status, assessing patient improvement, and assessing function of the device. In certain embodiments, information indicative of one or more sensor signals may be transmitted via wired or wireless means (e.g., via Bluetooth, WiFi, Zigbee, or another suitable protocol) to a mobile phone, a computer, a data logging device, or another suitable device that may optionally be connected to a local network, a wide-area network, a telephonic network, or other communication network. In certain embodiments, a data port (e.g., micro USB or other type) may be provided to permit extraction or interrogation of information contained in a memory.

Some embodiments in accordance with the present disclosure comprise at least one substrate. In some of such embodiments, the substrate is rigid, and in some of such embodiments, the substrate is flexible or moldable. Substrates can be made of any suitable material (or combinations of materials), a variety of which are well known to persons of skill in the art, and substrates formed of any such materials are included in the present disclosure.

Some embodiments in accordance with the present disclosure comprise at least one circuit board. In some of such embodiments, the circuit board is flexible or rigid, substantially translucent or not substantially translucent. Persons of skill in the art are familiar with a wide variety of circuit boards, and any such circuit boards can be employed in embodiments according to the present disclosure. As is well known, circuit boards generally comprise electrically-conductive regions and non-electrically-conductive regions, whereby electrical current can be delivered to electronic components as desired. Some embodiments in accordance with the present disclosure comprise circuit boards configured such that light emitters that emit light within different respective wavelength ranges are separately addressable, or in which some or all of the light emitters are separately addressable.

Some embodiments in accordance with the present disclosure comprise light emitters. Persons of skill in the art are familiar with, and have ready access to, a wide variety of light emitters that emit light within different wavelength ranges, and any suitable light emitters can be employed in accordance with the present disclosure.

Persons of skill in the art are familiar with, and have ready access to, a wide variety of solid state light emitters, and any suitable solid state light emitters can be employed in the devices according to the present disclosure. For example, persons of skill in the art are familiar with, and have ready access to, and can readily make, a variety of LEDs, laser diodes, and other solid state light emitters that emit light within desired portions of the respective wavelength ranges described herein, and any of such solid state light emitters can be employed in embodiments in accordance with the present disclosure.

Solid state light emitters employed in the lighting devices and lighting arrangements according to the present inventive subject matter can be selected from among solid state light emitters that have any suitable or desired full width at half max (FWHM) values. Persons of skill in the art are familiar with FWHM values for solid state light emitters.

In embodiments of methods that comprise emitting light and embodiments of devices that comprise light emitters, the light emitters can emit light in any desired temporal way, e.g., any light emitters can emit light in sync or not in sync, light emitters that emit light within a particular wavelength range can emit light in sync or not in sync, light emitters in different areas of the device (e.g., to treat a particular region of a user's skin) can emit light in sync or not in sync, any light emitters can emit light for the entire duration of a treatment, they can emit light in relative short pulses (in any desired pattern) during a treatment, they can emit light in a plurality of sustained sub-treatments during treatment (or a combination of pulses and sub-treatments). Any light emitters can emit light in sync, and any light emitters can emit light in accordance with different emission patterns.

Some embodiments in accordance with the present disclosure comprise one or more light-transmissive elements. Light-transmissive elements can comprise any suitable materials (e.g., in some embodiments, a light-transmissive element can comprise a light-transmissive encapsulating material), and can be of any desired shape and dimensions.

Some embodiments in accordance with the present disclosure comprise one or more waveguides, reflectors (and/or reflective regions), and/or light-affecting elements. Persons of skill in the art are familiar with a wide variety of waveguides, reflectors, reflective regions, and light-affecting elements, and any of such waveguides, reflectors, reflective regions, and light-affecting elements can be included in devices according to the present disclosure. Light-affecting elements encompass any material, structure or feature that affects light, a wide variety of which are well known to persons of skill in the art, representative examples of types of light-affecting elements including wavelength conversion materials, light diffusion or scattering materials, light diffusion or scattering features, light coupling features (e.g., features in which an index of refraction differs from one or more adjacent structures), and light extraction features. In some embodiments, light-affecting elements can be included to make more uniform the light that impinges on the region of skin being treated.

Some embodiments in accordance with the present disclosure comprise one or more lenses (including lenses that comprise numerous lenslets). Persons of skill in the art are familiar with a wide variety of lenses, and any such lenses can be included in devices according to the present disclosure. Some lenses can be considered light-affecting elements. One specific type of lens is a lenticular lens (some of which have a large number of lenslets). A lenticular lens, or any other type of lens, can have any desired thickness and any desired lenslet density, and can be formed of any suitable material or materials. In some embodiments, one or more lenses (and/or lenslets) can be included to make more uniform the light that impinges on the region of skin being treated.

Any or all of the elements (including layers), materials and features in devices in embodiments according to the present disclosure can be provided as separate elements (and there can be any desired number of any particular type of element), and/or any of the elements, materials and features of such devices can be combined in any suitable way. For example, embodiments according to the present disclosure can comprise one or more substrates, one or more circuit boards, one or more light-transmissive elements, one or more waveguides, one or more reflectors (and/or reflective regions), one or more light-affecting elements, and/or one or more lenses, each of which can be in a separate element or any of which can be combined in any suitable way (For example, a circuit board can be included in a substrate, a light-transmissive element or a lens; a reflector and/or a reflective region can be included in a substrate; one or more wavelength conversion materials can be dispersed in or deposited on a substrate, a light-transmissive element or a lens; one or more light diffusing or scattering materials can be dispersed in or deposited on a substrate, a light-transmissive element or a lens; one or more light diffusing or scattering features can be provided in or on a substrate, a light-transmissive element or a lens; one or more light coupling features can be provided in or on a substrate, a light-transmissive element or a lens; one or more light extraction features can be provided in or on a substrate, a light-transmissive element or a lens; and/or one or more of such light-affecting elements can be provided in one or more function material sheets or layers provided in any region of the device, e.g., between two light-transmissive elements, such as two encapsulating material layers).

Some embodiments in accordance with the present disclosure comprise at least a first eyepiece. In some of such embodiments, the eyepiece (or eyepieces) blocks passage of at least some light that is incident on the first eyepiece (and in some cases, blocks at least 75 percent, at least 90 percent or substantially all, of light that is incident on the first eyepiece), e.g., including light emitted by light emitters in or on the device. Persons of skill in the art are familiar with a wide variety of light-blocking materials (e.g., silicone), and any such materials can be used. In some embodiments, the eyepiece (or eyepieces) is removable, whereby different sized eyepieces can readily be substituted into or out of the device to accommodate users of different size and/or to alter the standoff of the mask, i.e., the distance by which the mask, or portions of the mask (in some cases, a nose-conforming portion of the mask and/or a chin-conforming portion of the mask), is/are spaced from the user's face.

Some embodiments in accordance with the present disclosure comprise one or more covering elements. In some of such embodiments, the covering element (or covering elements) can comprise fabric, and in some cases, the covering element can be breathable to permit transport of heat and fluid transport (e.g., evaporation of sweat). Representative examples of fabrics that can be used to make a covering element include cotton, open or closed cell polyethylene foam, polyester, rayon, etc. A covering element can be used to provide a pleasing outer layer to a device (e.g., a layer in a mask that is farthest from the user's face, i.e., the layer that would be most visually apparent to a person who is looking toward a user's face). A covering element (if provided) can be removably engaged to any other part of a device, e.g., to a substrate, e.g., by providing one of a pair of engaging components on the covering element and the other of a pair of engaging components on the element to which the covering element is removably attached (such as by attaching the hooks portion of Velcro® on one and the loops portion of Velcro® on the other, or by attaching one component of a snap or clip on one and the other component of a snap or clip on the other). By providing a removable covering element (or by providing removable covering elements), the covering element can easily be removed for washing, and/or can easily be substituted for, e.g., with a covering element of a different pattern, a covering element that is less worn out and/or a covering element of a different shape or size.

Some embodiments in accordance with the present disclosure comprise a strap or a headband. In some of such embodiments, the strap can be adjustable (e.g., in length), whereby the device can fit on different portions of bodies, different animals, different sized animals, etc., and/or a headband can be adjustable (e.g., in length) to fit on heads of different sizes.

In some embodiments, there is provided a mask that comprises a headband, in which the mask is configured to be engaged with a human user, with a first surface of the mask conforming to the human user's face, and with: a first imaginary line that bisects the headband along a portion of the headband extending away from the first headband engagement feature, and an imaginary line that bisects a region of the mask that conforms to a forehead of a human user with whom the mask is engaged, and that extends vertically, with the human user's head oriented upright (a) intersecting at a location that is below the human user's forehead, with the human user's head oriented upright, and (b) forming an angle in a range of from about 50 degrees to about 70 degrees (and in some embodiments in a range of from about 55 degrees to about 65 degrees, in some embodiments in a range of from about 58 degrees to about 62 degrees, in some embodiments about 60 degrees). Having a headband that provides such an angle in such a range can facilitate a user easily and rapidly removing the mask, e.g., when a person enters the room and the user does not want to be seen wearing the mask, or does not want to be seen wearing the mask for longer than a relatively short period of time. The ease and rapidity with which a mask can be removed can, in some embodiments, be enhanced where a high percentage of force being exerted by the headband and pushing the device toward the user's face is applied against a combination of (1) the human user's forehead and (2) areas of the human user's face that one or more eyepieces of the mask contact, as described elsewhere herein in connection with other features. In addition, with such features, greater airflow can occur between the mask and the user's face, enhancing comfort (e.g., reducing the temperature of the user's face and/or of the mask).

Some embodiments of masks in accordance with the present disclosure comprise one or more eyepieces and a headband, and the mask is configured to be engaged with a human user, with a first surface of the mask conforming to the human user's face, with the headband extending around the human user's head and exerting force that pushes the mask toward the human user's face, and with a relatively high percentage (e.g., at least 50 percent, at least 60 percent, at least 70 percent, at least 80 percent, or at least 90 percent) of said force being applied against a combination of (1) the human user's forehead and (2) areas of the human user's face that the one or more eyepieces contact. In some of such embodiments, as a result of the percentage of force being exerted by the headband and pushing the mask toward the user's face being applied against a combination of (1) the human user's forehead and (2) areas of the human user's face that one or more eyepieces of the mask contact being high, the mask is more comfortable for the user, and/or the mask can be more easily and rapidly removed by the user, e.g., when a person enters the room and the user does not want to be seen wearing the mask, or does not want to be seen wearing the mask for longer than a relatively short period of time, and/or greater airflow can occur between the mask and the user's face, enhancing comfort (e.g., reducing the temperature of the user's face and/or of the mask).

In some embodiments in accordance with the present disclosure, one or more components of the device (e.g., a light-transmissive element, a substrate, a circuit board) is/are moldable to some degree. The provision of such moldability in one or more components in some embodiments can allow the device to be adapted to more closely conform to a user, thereby increasing effectiveness, uniformity of light delivery and/or user comfort.

As noted above, in some aspects of the present disclosure, there are provided devices for treating living skin tissue, each of such devices comprising a substrate and at least first and second groups of light emitters. In some aspects of the present disclosure, there are provided such devices, in which any one of the following features is provided, or in which any combination of two or more of the following features are provided:

the device further comprises a circuit board;
the device further comprises a light-transmissive element;
the circuit board comprises electrically-conductive regions and non-electrically-conductive regions;
the circuit board is in or on the substrate;
the light-transmissive element is on the circuit board;
the circuit board is configured to deliver electrical current to the first group of light emitters and to the second group of light emitters;
each of the first group of light emitters is configured to emit light of wavelength in a range of from about 610 nm to about 630 nm;
each of the second group of light emitters is configured to emit light of wavelength in a range of from about 840 nm to about 860 nm;
the first group of light emitters and the second group of light emitters are configured to emit light of a combined irradiance flux density in the range of from about 1 mW/cm$^2$ to about 60 mW/cm$^2$;
the device comprises at least a first eyepiece;
the first eyepiece is engaged by the substrate;
the first eyepiece (or one or more eyepieces) is removable from the substrate;
the first eyepiece blocks passage of at least some light that is incident on the first eyepiece;
the first eyepiece blocks passage of at least 75 percent of light emitted by the first and second groups of light emitters that is incident on the first eyepiece;
the device is configured to conform to at least a portion of a face of a living being;
the substrate comprises at least a first eye opening;
the first eyepiece is in contact with portions of the substrate that extend around the first eye opening;
the device is configured to conform to at least a portion of a body;
the device configured to conform to at least a portion of a human face;
at least a portion of the device is flexible;
at least a portion of the device is moldable;
the device comprises at least a first lens element that comprises at least a first light scattering region;
the device further comprises at least one wavelength conversion material;
the device further comprises at least one light scattering material;
the device comprises at least a first light scattering feature;
the device comprises at least a first light extraction feature;
the device further comprises at least a first reflective region;
each of the first group of light emitters is a solid state light emitter, and each of the second group of light emitters is a solid state light emitter;
each of the first group of light emitters is a LED or a laser diode, and each of the second group of light emitters is a LED or a laser diode;
for each of the first group of light emitters, at least 70 percent of light emitted by the light emitter is of wavelength in the range of from about 600 nm to about 640 nm, and for each of the second group of light emitters, at least 70 percent of light emitted by the light emitter is of wavelength in the range of from about 830 nm to about 870 nm;
each of the first group of light emitters has a peak wavelength in the range of from about 610 nm to about 630 nm, and each of the second group of light emitters has a peak wavelength in the range of from about 840 nm to about 860 nm;

each of the first group of light emitters has a dominant wavelength in the range of from about 610 nm to about 630 nm;

each of the first group of light emitters has a centroid wavelength in the range of from about 610 nm to about 630 nm, and each of the second group of light emitters has a centroid wavelength in the range of from about 840 nm to about 860 nm;

for each of at least 70 percent of the light emitters in the device, the peak wavelength of the light emitter is in the range of from about 610 nm to about 630 nm or in the range of from about 840 nm to about 860 nm;

the device further comprises a third group of light emitters, and each of the third group of light emitters emits light of wavelength in the range of from about 640 nm to about 660 nm;

for each of at least 70 percent of the light emitters in the device, the peak wavelength of the light emitter is in the range of from about 610 nm to about 630 nm, in the range of from about 840 nm to about 860 nm, or in the range of from about 640 nm to about 660 nm;

the device has a first light emission surface, and for each of at least 70 percent of fifty 1 cm$^2$ imaginary substantially square regions on a 50 cm$^2$ region of the first light emission surface of the device, the irradiance flux density of the imaginary substantially square region is between about 0.5 to about 1.5 times a single irradiance flux density value, upon electrical current flowing to the first and second groups of light emitters;

the device further comprises driver circuitry configured to deliver electrical current to the circuit board so as to cause the first and second groups of light emitters to emit light;

the device comprises a first major surface and a second major surface, and light is emitted from the first major surface, upon electrical current flowing to the first and second groups of light emitters (and in some embodiments, the first major surface is configured to conform to at least a portion of a human face);

the device comprises a plurality of holes extending through the device;

the device further comprises a covering element, the covering element comprises fabric, and the covering element is on the substrate;

the device comprises a first major surface and a second major surface, light is emitted from the first major surface of the device upon electrical current flowing to the first and second groups of light emitters, and the covering element covers at least a portion of the second major surface of the device;

the device further comprises at least a first sensor;

the device further comprises at least a first eyepiece, and any imaginary line that passes through a space defined by a perimeter of the substrate necessarily passes through at least one of: (1) a portion of the substrate, (2) a location that is within 1 cm of a portion of the substrate, (3) through the first eyepiece, and (4) through a region defined by a perimeter of the first eyepiece;

the substrate and the circuit board are both part of a single unitary one-piece element;

the substrate and the circuit board are separate components;

the substrate and the circuit board are in direct contact with each other;

the circuit board and the light-transmissive element are both part of a single unitary one-piece element;

the circuit board and the light-transmissive element are separate components;

the substrate, the circuit board and the light-transmissive element are all part of a single unitary one-piece element;

the device further comprises a strap and at least first and second strap engagement features, a first region of the strap is engaged with the first strap engagement feature, and a second region of the strap is engaged with the second strap engagement feature; and the device further comprises a strap and a covering element, the covering element comprises at least first and second strap engagement features, a first region of the strap is engaged with the first strap engagement feature, a second region of the strap is engaged with the second strap engagement feature, the covering element comprises fabric, and the covering element is on the substrate.

As noted above, in other aspects of the present disclosure, there are provided face-engaging devices, each of such devices comprising a substrate, one or more eyepieces, and a headband. In some aspects of the present disclosure, there are provided such devices, in which any one of the following features is provided, or in which any combination of two or more of the following features are provided:

the device further comprises at least first and second headband engagement features;

the one or more eyepieces are engaged by the substrate;

the substrate comprises one or more eye openings;

the one or more eyepieces are in contact with portions of the substrate that extend around the one or more eye openings;

a first region of the headband is engaged with the first headband engagement feature;

a second region of the headband is engaged with the second headband engagement feature;

the device is configured to be engaged with a human user, with a first surface of the device conforming to the human user's face, with the headband extending around the human user's head and exerting force that pushes the device toward the human user's face, and with at least 80 percent of said force being applied against a combination of (1) the human user's forehead and (2) areas of the human user's face that the one or more eyepieces contact;

the one or more eyepieces block passage of at least some light that is incident on the one or more eyepieces;

at least a portion of the device is flexible;

at least a portion of the device is moldable;

the device comprises a plurality of holes extending through the device;

the device further comprises a covering element, the covering element comprises fabric, and the covering element is on the substrate (and in some cases, the device comprises a first major surface and a second major surface, the first major surface of the device comprises said first surface of the device conforming to the human user's face, and the covering element covers at least a portion of the second major surface of the device);

the device further comprises at least a first sensor;

any imaginary line that passes through a space defined by a perimeter of the substrate necessarily passes through at least one of: (1) a portion of the substrate, (2) a location that is within 1 cm of a portion of the substrate, (3) through the one or more eyepieces, and (4) through a region defined by a perimeter of the one or more eyepieces;

the headband is adjustable, whereby a distance between the first region of the headband and the second region of the headband can be adjusted;

the device is configured to be engaged with a human user, with a first surface of the device conforming to the human user's face, and with: a first imaginary line that bisects the headband along a portion of the headband extending away from the first headband engagement feature, and an imaginary line that bisects a region of the device that conforms to a forehead of a human user with whom the device is engaged, and that extends vertically, with the human user's head oriented upright (a) intersecting at a location that is below the human user's forehead, with the human user's head oriented upright, and (b) forming an angle in a range of from about 50 degrees to about 70 degrees;

the device further comprises a covering element, the covering element comprises the first and second headband engagement features, the covering element comprises fabric, and the covering element is on the substrate.

Details of illustrative devices that may be used for modulating nitric oxide levels, and enhancing collagen production, are described below.

As shown in FIG. 1, a mask 10 includes: a substrate in the form of a housing 12, which can be a polycarbonate mask housing; a light-transmissive element 14 in the form of a lens, which can be a clear polycarbonate lens; a battery 16, which can be a lithium polymer battery; a user interface printed circuit board (UI PCB) bracket 18, which holds a push or activation button 20 and charge connector, wherein the activation button 20 can be made of silicone; an LED PCB assembly 22, which can be a flexible circuit board; an eyepiece 24, for example, an eye shield made of a material, such as silicone that is dark or opaque in color, which protects the eye from damaging light rays when skin around the eye is irradiated to reduce wrinkles; a controller 26, for example, a DBM LED circuit board controller; a user interface 28, which is used to charge and activate the LED PCB assembly 22; and a covering element 30 in the form of a fabric mask placeholder, which can be a sewn fabric mask cover. In certain embodiments, the mask 10 may include a plurality of standoffs 31 positioned between the LED PCB assembly 22 and the light-transmissive element 14. In certain embodiments, the standoffs 31 may be attached to (e.g., by adhesive), or may be integrally formed with, the light-transmissive element 14 (e.g., by molding the standoffs 31 concurrently with the light-transmissive element 14). The standoffs 31 may contact the LED PCB assembly 22 such that other portions of the light-transmissive element 14 may be spaced from the LED PCB assembly 22. Such spacing may be uniform across the mask 10 in certain embodiments. By providing spacing between the light-transmissive element 14 and the LED PCB assembly 22, LEDs mounted on the LED PCB assembly 22 may emit light more uniformly into the light-transmissive element 14, and increased thermal separation may be provided between the LED PCB assembly 22 and a patient's skin. Each of the light-transmissive element 14, the LED PCB assembly 22, the housing 12 and the covering element 30 may include a respective eye opening (32A, 32B, 32C, and 32D, respectively) in which the eyepiece 24 is received. The eyepiece 24 may be arranged to extend through the eye openings 32A-32D such that a portion of the eyepiece 24 extends beyond the light-transmissive element 14 to engage the eye sockets of a user and reduce or block light from reaching the user's eyes. FIG. 2 is an exploded view from the inside of the mask 10 shown in FIG. 1. The parts of the mask 10 are the same as those identified above with respect to FIG. 1.

For illustrative purposes, LED elements are omitted from the LED PCB assembly 22 in FIGS. 1 and 2. In certain embodiments, the LED PCB assembly 22 may include a plurality of LEDs that provide light for treatment and/or conditioning of skin. The light may be provided by applying light of at least two peak wavelengths (each of a respective peak radiant flux) to the skin of interest. Light having a first peak wavelength (and of a first radiant flux, which can be substantially constant or which can be variable, and/or which can be uniform across the treatment area or which can differ in different regions) may be applied to the skin in order (1) to stimulate enzymatic generation of nitric oxide to increase endogenous stores of nitric oxide, and/or (2) to stimulate release of nitric oxide from the endogenous stores. The light of the first peak wavelength may be in a range from 610 to 630 nm, or in a range from 615 to 625 nm. Light having a second peak wavelength (and of a second radiant flux, which can be substantially constant or which can be variable and/or uniform or non-uniform, and which may be the same or different from the first radiant flux) may be provided to stimulate collagen production in the skin. In certain embodiments, the second peak wavelength may be at least 230 nm greater than the first peak wavelength. For example, the second peak wavelength may be provided in a range from 840 to 860 nm. In still further embodiments, light provide by the LED PCB assembly 22 may include light of a third peak wavelength (and of a third radiant flux) that may be applied to reduce inflammation. For example, the third peak wavelength may be provided in a range from 640 nm to 660 nm, or in a range from 645 nm to 655 nm.

FIGS. 3A, 3B, 3C, 3D, 3E, 3F and 3G show a perspective view, a back view, a left side view, a front view, a right side view, a top view, and a bottom view, respectively, of the mask 10 shown in FIGS. 1 and 2. In FIGS. 3A, 3B, 3C, 3D, 3E, and 3G, the covering element 30 is omitted for illustrative purposes. The housing 12 may include one or more recesses 33 formed in a front face thereof for receiving portions of the covering element 30, including additional material and/or components associated with securing the covering element 30 to the remainder of the mask 10. In certain embodiments, the recesses 33 may be arranged around a perimeter of the housing 12 and/or along portions of the housing 12 that surround the eyepiece 24. The recesses 33 may accommodate bulkier portions of the covering element 30 or other components associated with securing the covering element 30. In this regard, portions of the covering element 30 that are outside the recesses 33 may be arranged conformally with the housing 12.

Figure 4B:
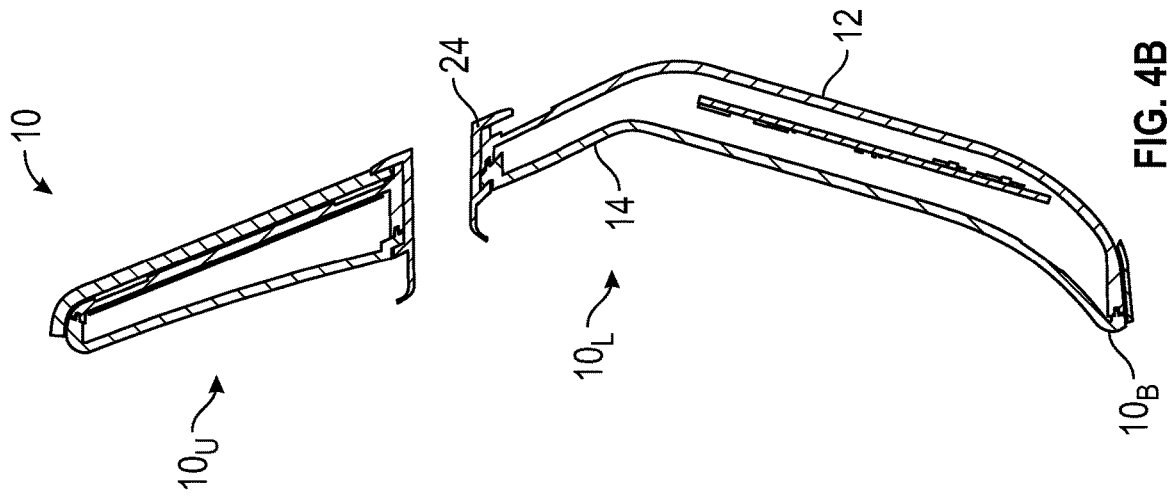
FIGS. 4A and 4B are schematic illustrations of a midline cutaway, which shows internal spacing and dimensions of one embodiment of a mask as described herein.
Figure 4A:
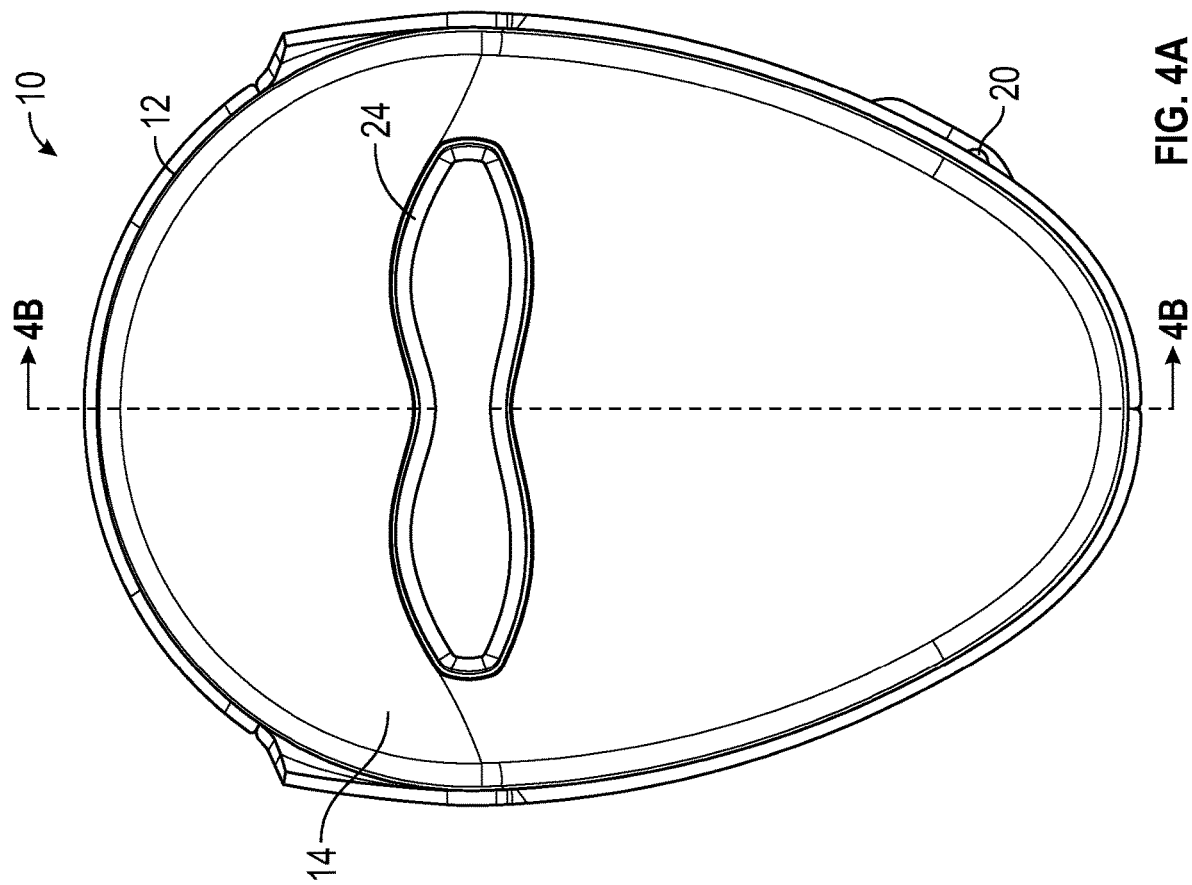

FIGS. 4A and 4B are schematic illustrations of a midline cutaway, which shows internal spacing and dimensions of one embodiment of the mask 10 of FIGS. 3A-3G as described herein. FIG. 4A is similar to FIG. 3B and further includes a section line labeled as 4B-4B. FIG. 4B is a side view of the mask 10 taken along the section line 4B-4B of FIG. 4A. As illustrated in FIG. 4B, an upper portion 10u of the mask 10 may be defined above the eyepiece 24 and a lower portion 10L of the mask 10 may be defined below the eyepiece 24. In order to accommodate a wide variety of face shapes for intended users, the mask may be configured to promote increased contact with a user's face along the upper portion 10u to secure the mask 10 in place during treatment. In this regard, the lower portion 10L may rest lightly against the user's face or even be spaced from the user's face. Accordingly, the mask 10 may apply a sufficient force to the forehead and/or eye socket regions of a user's face while providing increased comfort for the nose, cheeks, and mouth of the user's face. Additionally, the mask 10 may be more easily and rapidly removed by the user when the contact is provided by the upper portion 10u of the mask 10. In still further embodiments, a bottom edge 10B of the mask may curve inward (e.g., to the left in FIG. 4B) so that corresponding portions of the mask 10 may extend below a user's chin and curve toward the user's neck for delivery of light.

Figure 5:
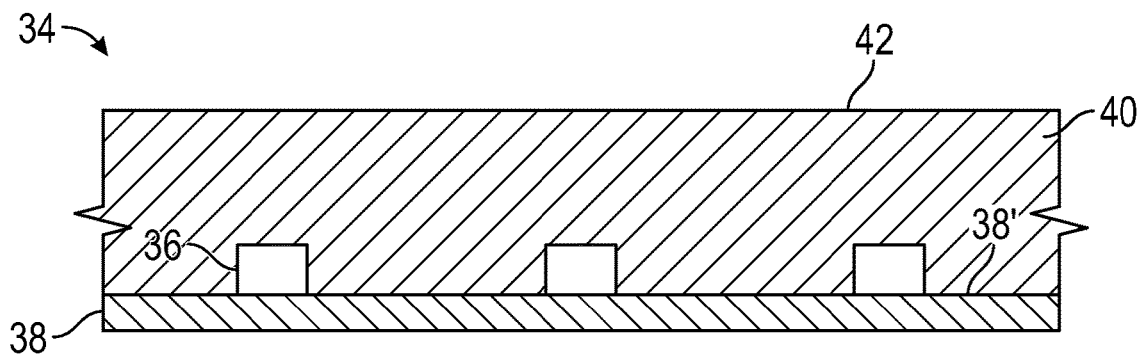
FIG. 5 is a side cross-sectional schematic view of a portion of a device for delivering light energy to living skin tissue.

FIG. 5 is a side cross-sectional schematic view of a portion of a device 34 for delivering light energy to living skin tissue, the device 34 including multiple direct view light-emitting sources 36 supported by a substrate 38 and covered with an encapsulating material 40, which may be embodied in a sheet or layer. In certain aspects, the substrate 38 and light-emitting sources 36 may embody the LED PCB assembly 22 of FIGS. 1 and 2, and the encapsulating material may embody the light-transmissive element 14 or a separate element that is provided on the LED PCB assembly 22 of FIGS. 1 and 2. The substrate 38 preferably includes a flexible PCB, which may include a reflective surface 38' to reflect light toward a light-transmissive outer surface 42 of the device 34. As shown in FIG. 5, the encapsulating material 40 may cover the light-emitting sources 36 and an upper surface of the substrate 38; however, it is to be appreciated that in certain embodiments the encapsulating material 40 may cover any suitable portions of the light-emitting sources 36 and the substrate 38, e.g., the encapsulating material 40 can cover both upper and lower surfaces of the substrate 38. In still further embodiments, the encapsulating material 40 may form a lens that is spaced from one or more portions of the substrate 38 and light-emitting sources 36. In certain embodiments, different light-emitting sources 36 may generate light having different peak wavelengths. In certain embodiments, one or more light-emitting sources 36 may include a multi-emitter package arranged to generate one or multiple peak wavelengths of light. In certain embodiments, one or more light-emitting sources 36 may be arranged to produce one or both of collagen-promoting light and ES increasing and/or ES releasing light.

Figure 6:
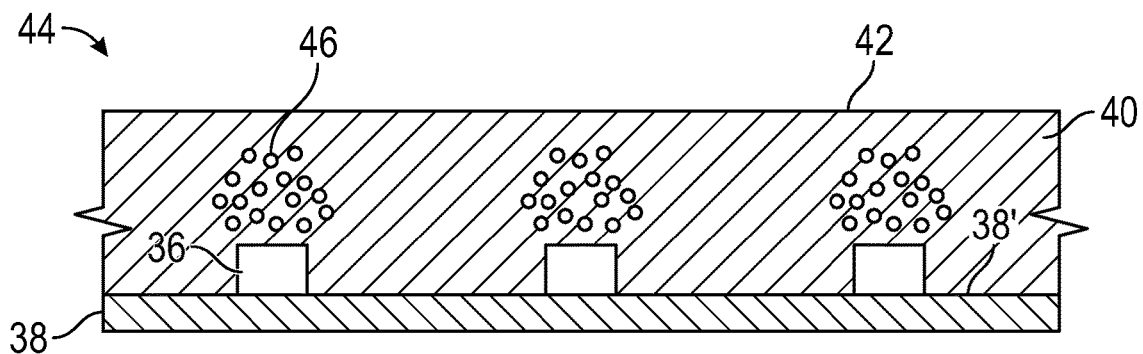
FIG. 6 is a side cross-sectional schematic view of a portion of a device for delivering light energy to living skin tissue, the device including multiple direct view light-emitting sources supported by a substrate and covered with an encapsulating material, which may be embodied in a sheet or layer.

FIG. 6 is a side cross-sectional schematic view of a portion of a device 44 for delivering light energy to living skin tissue, the device 44 including multiple direct view light-emitting sources 36 supported by the substrate 38 and covered with the encapsulating material 40, which may be embodied in a sheet or layer. The substrate 38 preferably includes a flexible PCB, which may include the reflective surface 38' to reflect light toward the light-transmissive outer surface 42 of the device 44. At least one functional material (e.g., wavelength conversion material and/or scattering material) 46 may be disposed within the encapsulating material 40. In certain embodiments, the functional material(s) 46 includes one or more wavelength conversion materials, such as at least one of a phosphor material, a fluorescent dye material, a quantum dot material, and a fluorophore material. In certain embodiments, wavelength conversion materials that emit different respective peak wavelengths may be applied over different light-emitting sources 36. In certain embodiments, the functional material(s) 46 are applied by dispensing or printing. In certain embodiments, one or more of the light-emitting sources 36 may include a multi-emitter package arranged to generate one or multiple peak wavelengths of light. In certain embodiments, one or more light-emitting sources 36 may be arranged to produce one or both of collagen-promoting light and ES increasing and/or ES releasing light.

FIG. 7 is a side cross-sectional schematic view of a portion of a device 48 for delivering light energy to living skin tissue, the device 48 including multiple direct view light-emitting sources 36 supported by the substrate 38 and covered with two encapsulating material layers 40A, 40B, with at least one functional material 46 (e.g., wavelength conversion and/or scattering material) in the form of a sheet or layer disposed between the encapsulating material layers 40A, 40B. The substrate 38 preferably includes a flexible PCB, which may include the reflective surface 38' to reflect light toward the light-transmissive outer surface 42 of the device 48. In certain embodiments, the functional material(s) 46 include one or more wavelength conversion materials, such as at least one of a phosphor material, a fluorescent dye material, a quantum dot material, and a fluorophore material. In certain embodiments, one or more light-emitting sources 36 may include a multi-emitter package arranged to generate one or multiple peak wavelengths of light. In certain embodiments, one or more light-emitting sources 36 may be arranged to produce one or both of collagen-promoting light and ES increasing and/or ES releasing light.

FIG. 8 is a side cross-sectional schematic view of a portion of a device 50 for delivering light energy to living skin tissue, the device 50 including multiple direct view light-emitting sources 36 supported by the substrate 38 and covered by the encapsulating material 40, which may be embodied in a sheet or layer. The substrate 38 preferably includes a flexible PCB, which may include the reflective surface 38' to reflect light toward the light-transmissive outer surface 42 of the device 50. The encapsulating material 40 may be covered with a diffusing or scattering material layer 52. In certain embodiments, the diffusing or scattering material layer 52 may include acrylic, PET, silicone, or a polymeric sheet. In certain embodiments, the diffusing or scattering material layer 52 may include scattering particles such as zinc oxide, silicon dioxide, titanium dioxide, or the like. In certain embodiments, one or more light-emitting sources 36 may include a multi-emitter package arranged to generate one or multiple peak wavelengths of light. In certain embodiments, one or more light-emitting sources 36 may be arranged to produce one or both of collagen-promoting light and ES increasing and/or ES releasing light.

FIG. 9 is a side cross-sectional schematic view of a portion of a device 54 for delivering light energy to living skin tissue, the device 54 including multiple direct view light-emitting sources 36 supported by the substrate 38. The substrate 38 preferably includes a flexible PCB, which may include the reflective surface 38' to reflect light toward the light-transmissive outer surface 42 of the device 54. Multiple molded light scattering features 56 (e.g., molded from silicone) overlie the light-emitting sources 36. The encapsulating material 40 or light coupling material is arranged between the light-emitting sources 36 and molded features 56. In certain embodiments, the encapsulating material 40 or light-coupling material may include a light coupling gel with an index of refraction that differs from an index of refraction of the molded features 56. The molded features 56 may be arranged along the light-transmissive outer surface 42 of the device 54. In certain embodiments, the one or more light-emitting sources 36 may include a multi-emitter package arranged to generate one or multiple peak wavelengths of light. In certain embodiments, the one or more light-emitting sources 36 may be arranged to produce one or both of collagen-promoting light and ES increasing and/or ES releasing light.

FIG. 10 is a side cross-sectional schematic view of a portion of a device 58 for delivering light energy to living skin tissue, the device 58 including the flexible substrate 38, a passive-matrix organic light-emitting diode (OLED) structure (embodied in an anode layer 60A, a cathode layer 60B, and an OLED stack 62 between the anode and cathode layers 60A, 60B). In certain embodiments, the OLED stack 62 may be configured to generate multiple wavelengths of light. The substrate 38 preferably includes a flexible PCB, which may include the reflective surface 38' to reflect light toward the light-transmissive outer surface 42 of the device 58. The encapsulating material 40 or layer is arranged over the cathode layer 60B and preferably defines the light-transmissive outer surface 42 of the device 58. In certain embodiments, one or more light-emitting wavelengths produced by the OLED stack 62 may include one or both of collagen-promoting light and ES increasing and/or ES releasing light.

FIG. 11 is a side cross-sectional schematic view of a portion of a device 64 for delivering light energy to living skin tissue, the device 64 including the flexible substrate 38, multiple direct view light-emitting sources 36 supported by the substrate 38, and encapsulating material layers 40A, 40B arranged above and below the substrate 38, respectively. The substrate 38 preferably includes a flexible PCB, which may include the reflective surface 38' to reflect light toward the light-transmissive outer surface 42 of the device 64. The device 64 further includes or forms holes or perforations 66 defined through both the substrate 38 and the encapsulating material layers 40A, 40B. In certain embodiments, the one or more light-emitting sources 36 may be arranged to produce one or both of collagen-promoting light and ES increasing and/or ES releasing light.

FIG. 12 is a side cross-sectional schematic view of a portion of a device 68 for delivering light energy to living skin tissue, wherein the device 68 includes multiple direct view light-emitting sources 36 supported by the flexible substrate 38 and covered by the encapsulating material 40. The substrate 38 preferably includes a flexible PCB, which may include the reflective surface 38' to reflect light toward the light-transmissive outer surface 42 of the device 68. The device 68 is preferably flexible to permit it to be bent or shaped into a variety of shapes to conform to a portion of a mammalian body. As illustrated, the device 68 is arranged in a concave configuration with the multiple light-emitting sources 36 arranged to direct emissions toward a center of curvature of the device 68. In certain embodiments, the one or more light-emitting sources 36 may be arranged to produce one or both of collagen-promoting light and ES increasing and/or ES releasing light.

FIG. 13 is a side cross-sectional schematic view of a portion of a device 70 for delivering light energy to living skin tissue, wherein the device 70 includes multiple direct view light-emitting sources 36 supported by the flexible substrate 38 and covered by the encapsulating material 40. The substrate 38 preferably includes a flexible PCB, which may include the reflective surface 38' to reflect light toward the light-transmissive outer surface 42 of the device 70. The device 70 is preferably flexible to permit it to be bent or shaped into a variety of shapes to conform to a portion of a mammalian body. As illustrated, the device 70 is arranged in a convex configuration with the multiple light-emitting elements or sources 36 arranged to direct emissions away from a center of curvature of the device 70. In certain embodiments, the one or more light-emitting sources 36 may be arranged to produce one or both of collagen-promoting light and ES increasing and/or ES releasing light.

FIG. 14A is a side cross-sectional schematic view of a portion of a device 72 for delivering light energy to living skin tissue, wherein the device 72 is edge lit with one or more light-emitting sources 36 supported by the substrate 38 (e.g., a flexible PCB) that preferably includes the reflective surface 38'. Other non-light-transmitting surfaces of the device 72 are bounded by a flexible reflective substrate 74 arranged to reflect light toward the light-transmissive outer surface 42 of the device 72. The substrate 38, the light-emitting source(s) 36, and the reflective substrate 74 may be covered with the encapsulating material 40, which may include silicone. As illustrated, the device 72 may have a substantially uniform thickness. In certain embodiments, the one or more light-emitting sources 36 may be arranged to produce one or both of collagen-promoting light and ES increasing and/or ES releasing light.

FIG. 14B is a side cross-sectional schematic view of a portion of a device 76 for delivering light energy to living skin tissue, wherein the device 76 is edge lit with one or more light-emitting sources 36 supported by the substrate 38, or flexible PCB that preferably includes the reflective surface 38'. Other non-light-transmitting surfaces of the device 76 are bounded by the flexible reflective substrate 74 arranged to reflect light toward the light-transmissive outer surface 42 of the device 76. The substrate 38, the light-emitting source(s) 36, and the flexible reflective substrate 74 may be covered with the encapsulating material 40, which may include silicone. As illustrated, the device 76 may have a substantially uniform thickness. The device 76 further comprises a reflective element 78 at an end of the flexible reflective substrate 74 that redirects light toward the light-transmissive outer surface 42. In certain embodiments, the one or more light-emitting sources 36 may be arranged to produce one or both of collagen-promoting light and ES increasing and/or ES releasing light.

FIG. 15 is a side cross-sectional schematic view of a portion of a device 80 for delivering light energy to living skin tissue, wherein the device 80 is edge lit with one or more light-emitting sources 36 supported by the substrate 38, or flexible PCB that preferably includes the reflective surface 38'. A non-light-transmitting face of the device 80 is bounded by the flexible reflective substrate 74 arranged to reflect light toward the light-transmissive outer surface 42 of the device 80. The substrate 38, the light-emitting source(s) 36, and the flexible reflective substrate 74 may be covered with the encapsulating material 40, which may include silicone. As illustrated, the device 80 may have a thickness that is tapered with distance away from the light-emitting sources 36. Such tapered thickness may enable the device 80 to more easily be wrapped against or to conform to areas of a mammalian (e.g., human) body. In certain embodiments, the one or more light-emitting sources 36 may be arranged to produce one or both of collagen-promoting light and ES increasing and/or ES releasing light.

FIG. 16 is a side cross-sectional schematic view of a portion of a device 82 for delivering light energy to living skin tissue, wherein the device 82 is edge lit with one or more light-emitting sources 36 supported by the substrate 38 or flexible PCB that bounds multiple edges and a face of the device 82. The substrate 38 preferably includes a reflective surface 38' arranged to reflect light toward the light-transmissive outer surface 42 of the device 82. The substrate 38 and the light-emitting source(s) 36 may be covered with the encapsulating material 40, which may include silicone. In certain embodiments, the one or more light-emitting sources

36 may be arranged to produce one or both of collagen-promoting light and ES increasing and/or ES releasing light.

FIG. 17 is a side cross-sectional schematic view of a portion of a device 84 for delivering light energy to living skin tissue, wherein the device 84 is edge lit with one or more light-emitting sources 36 supported by the substrate 38 or flexible PCB that bounds one edge and one face of the device 84. The substrate 38 preferably includes the reflective surface 38' arranged to reflect light toward the light-transmissive outer surface 42 of the device 84. The substrate 38 and the light-emitting source(s) 36 are covered with the encapsulating material 40, which may include silicone. As illustrated, the device 84 may have a thickness that is tapered with distance away from the light-emitting sources 36. In certain embodiments, the one or more light-emitting sources 36 may be arranged to produce one or both of collagen-promoting light and ES increasing and/or ES releasing light.

FIG. 18 is a side cross-sectional schematic view of a portion of a device 86 for delivering light energy to living skin tissue, wherein the device 86 is edge lit with one or more light-emitting sources 36 supported by the substrate 38 or flexible PCB that bounds multiple edges and a face of the device 86. In certain embodiments, one or more light-emitting sources 36 may include a multi-emitter package arranged to generate one or multiple peak wavelengths of light. The substrate 38 preferably includes the reflective surface 38' arranged to reflect light toward the light-transmissive outer surface 42 of the device 86. The substrate 38 and the light-emitting source(s) 36 may be covered with the encapsulating material 40, which may include silicone. Between the light-transmitting outer surface 42 and the encapsulating material 40, the device 86 further includes the diffusing and/or scattering material layer 52. In certain embodiments, the diffusing and/or scattering material layer 52 may include a sheet of material; in other embodiments, the diffusing and/or scattering material layer 52 may include particles applied in or on the encapsulating material 40. In certain embodiments, the one or more light-emitting sources 36 may be arranged to produce one or both of collagen-promoting light and ES increasing and/or ES releasing light.

FIG. 19 is a side cross-sectional schematic view of a portion of a device 88 for delivering light energy to living skin tissue, wherein the device 88 is edge lit with one or more light-emitting sources 36 supported by the substrate 38 or flexible PCB that bounds one edge and one face of the device 88. In certain embodiments, one or more light-emitting sources 36 may include a multi-emitter package arranged to generate one or multiple peak wavelengths of light. The substrate 38 preferably includes the reflective surface 38' arranged to reflect light toward the light-transmissive outer surface 42 of the device 88. The substrate 38 and the light-emitting source(s) 36 may be covered with the encapsulating material 40, which may include silicone. Between the light-transmitting outer surface 42 and the encapsulating material 40, the device 88 further includes the diffusing and/or scattering material layer 52. In certain embodiments, the diffusing and/or scattering material layer 52 may include a sheet of material; in other embodiments, the diffusing and/or scattering material layer 52 may include particles applied in or on the encapsulating material 40. As illustrated, the device 88 may have a thickness that is tapered with distance away from the light-emitting sources 36. In certain embodiments, the one or more light-emitting sources 36 may be arranged to produce one or both of collagen-promoting light and ES increasing and/or ES releasing light.

FIG. 20 is a side cross-sectional schematic view of a portion of a device 90 for delivering light energy to living skin tissue, wherein the device 90 is edge lit with one or more light-emitting sources 36 supported by the substrate 38 or flexible PCB that bounds multiple edges and a face of the device 90. In certain embodiments, one or more light-emitting sources 36 may include a multi-emitter package arranged to generate one or multiple peak wavelengths of light. The substrate 38 preferably includes the reflective surface 38' arranged to reflect light toward the light-transmissive outer surface 42 of the device 90. The substrate 38 and the light-emitting source(s) 36 may be covered with the encapsulating material 40, which may include silicone. Between the light-transmitting outer surface 42 and the encapsulating material 40, the device 90 further includes the functional material 46, such as a wavelength conversion material. In certain embodiments, the functional material 46 may include a sheet or layer of material; in other embodiments, the functional material 46 may include particles applied in or on the encapsulating material 40. In certain embodiments, the one or more light-emitting sources 36 may be arranged to produce one or both of collagen-promoting light and ES increasing and/or ES releasing light.

FIG. 21 is a side cross-sectional schematic view of a portion of a device 92 for delivering light energy to living skin tissue, wherein the device 92 is edge lit with one or more light-emitting sources 36 supported by the substrate 38 or flexible PCB that bounds one edge and one face of the device 92. In certain embodiments, one or more light-emitting sources 36 may include a multi-emitter package arranged to generate one or multiple peak wavelengths of light. The substrate 38 preferably includes the reflective surface 38' arranged to reflect light toward the light-transmissive outer surface 42 of the device 92. The substrate 38 and the light-emitting source(s) 36 may be covered with the encapsulating material 40, which may include silicone. Between the light-transmitting outer surface 42 and the encapsulating material 40, the device 92 further includes the functional material 46, such as a wavelength conversion material. In certain embodiments, the functional material 46 may include a sheet or layer of material; in other embodiments, the functional material 46 may include particles applied in or on the encapsulating material 40. As illustrated, the device 92 may have a thickness that is tapered with distance away from the light-emitting sources 36. In certain embodiments, the one or more light-emitting sources 36 may be arranged to produce one or both of collagen-promoting light and ES increasing and/or ES releasing light.

FIG. 22 is a side cross-sectional schematic view of a portion of a device 94 for delivering light energy to living skin tissue, wherein the device 94 is edge lit along multiple edges with multiple light-emitting sources 36 supported by the substrate 38 or flexible PCB having the reflective surfaces 38' arranged to reflect light toward the light-transmissive outer surface 42 of the device 94. The substrate 38 and light-emitting sources 36 may be covered with the encapsulating material 40, and the functional material 46 (e.g., the wavelength conversion material) may be distributed in the encapsulating material 40. In certain embodiments, one or more light-emitting sources 36 may include a multi-emitter package arranged to generate one or multiple peak wavelengths of light. In certain embodiments, the one or more light-emitting sources 36 may be arranged to produce one or both of collagen-promoting light and ES increasing and/or ES releasing light.

FIG. 23A is a side cross-sectional schematic view of a portion of a device 96 for delivering light energy to living skin tissue, wherein the device 96 is edge lit along multiple edges with multiple light-emitting sources 36 supported by the substrate 38 or flexible PCB having reflective surfaces 38' arranged to reflect light toward the light-transmissive outer surface 42 of the device 96. The device 96 further includes raised light extraction features 98 supported by the substrate 38, with such features 98 serving to reflect laterally-transmitted light toward the outer surface 42. The encapsulating material 40 is provided over the substrate 38, the light-emitting sources 36, and the light extraction features 98. In certain embodiments, the one or more light-emitting sources 36 may include a multi-emitter package arranged to generate one or multiple peak wavelengths of light. In certain embodiments, the one or more light-emitting sources 36 may be arranged to produce one or both of collagen-promoting light and ES increasing and/or ES releasing light.

In certain embodiments, the light extraction features 98 may be dispensed, molded, layered, or painted on the substrate 38. In certain embodiments, different light extraction features 98 may include different indices of refraction. In certain embodiments, different light extraction features 98 may include different sizes and/or shapes. In certain embodiments, light extraction features 98 may be uniformly or non-uniformly distributed over the substrate 38. In certain embodiments, light extraction features 98 may include tapered surfaces. In certain embodiments, different light extraction features 98 may include one or more connected portions or surfaces. In certain embodiments, different light extraction features 98 may be discrete or spatially separated relative to one another. In certain embodiments, light extraction features 98 may be arranged in lines, rows, zig-zag shapes, or other patterns. In certain embodiments, one or more wavelength conversion materials may be arranged on or proximate to one or more light extraction features 98.

FIG. 23B is a side cross-sectional schematic view of a portion of a device 100 for delivering light energy to living skin tissue, wherein the device 100 is edge lit along multiple edges with multiple light-emitting sources 36 supported by the substrate 38 or flexible PCB having reflective surfaces 38' arranged to reflect light toward the light-transmissive outer surface 42 of the device 100. The device 100 further includes raised light extraction features 98 supported by the substrate 38, with such features 98 serving to reflect laterally-transmitted light toward the outer surface 42. As shown in FIG. 23B, different light extraction features 98 include different sizes and/or shapes. In particular, from left to right, a first light extraction feature 98 has a first (longer) dimension of x and a second (shorter) dimension of y, a second light extraction feature 98 has a first dimension of x+1 and a second dimension of y+1, a third light extraction feature 98 has a first dimension of x+2 and a second dimension of y+2, a fourth light extraction feature 98 has a first dimension of x+3 and a second dimension of y+3, a fifth light extraction feature 98 is rounded, and sixth, seventh and eight light extraction features 98 have respective first dimensions that differ from respective second dimensions, and are oriented with their longer dimension to the right instead of to the left. The encapsulating material 40 is provided over the substrate 38, the light-emitting sources 36, and the light extraction features 98. In certain embodiments, the one or more light-emitting sources 36 may include a multi-emitter package arranged to generate one or multiple peak wavelengths of light. In certain embodiments, the one or more light-emitting sources 36 may be arranged to produce one or both of collagen-promoting light and ES increasing and/or ES releasing light.

FIG. 24 is a side cross-sectional schematic view of a portion of a device 102 for delivering light energy to living skin tissue, wherein the device 102 is edge lit along multiple edges with multiple light-emitting sources 36 supported by the substrate 38 or flexible PCB having reflective surfaces 38' arranged to reflect light toward the light-transmissive outer surface 42 of the device 102. In certain embodiments, the one or more light-emitting sources 36 may be arranged to produce one or both of collagen-promoting light and ES increasing and/or ES releasing light. Encapsulating material layers 40A, 40B are arranged above and below the substrate 38 and over the light-emitting sources 36. Holes or perforations 66 are defined through the substrate 38 and the encapsulating material layers 40A, 40B. The holes or perforations 66 preferably allow passage of at least one of air and exudate through the device 102.

Holes or perforations defined through a device (e.g., through a PCB and encapsulating layers) as described herein can be of any of various shapes and configurations. Holes may be round, oval, rectangular, square, polygonal, or any other suitable axial shape. Cross-sectional shapes of holes or perforations may be uniform or non-uniform. Cross-sectional shapes that may be employed according to certain embodiments are shown in FIGS. 25A-25C.

FIG. 25A is a cross-sectional view of a first exemplary hole 66-1 definable through the encapsulating material 40 of a device for delivering light energy to living skin tissue. The hole 66-1 has a diameter that is substantially constant with depth and extends to the light-transmissive outer surface 42. FIG. 25B is a cross-sectional view of a second exemplary hole 66-2 definable through the encapsulating material 40 of a device for delivering light energy to living skin tissue, the hole 66-2 having a diameter that increases as it extends away from the light-transmissive outer surface 42. FIG. 25C is a cross-sectional view of a third exemplary hole 66-3 definable through the encapsulating material 40 of a device for delivering light energy to living skin tissue, the hole 66-3 having a diameter that decreases as it extends away from the light-transmissive outer surface 42.

In certain embodiments, perforations or holes may encompass at least 2%, at least 5%, at least 7%, at least 10%, at least 15%, at least 20%, or at least 25% of a facial area of a device for delivering light energy to living skin tissue as disclosed herein. In certain embodiments, one or more of the preceding ranges may be bounded by an upper limit of no greater than 10%, no greater than 15%, no greater than 20%, or no greater than 30%. In certain embodiments, perforations or holes may be provided with substantially uniform size and distribution, with substantially uniform distribution but non-uniform size, with non-uniform size and non-uniform distribution, or any other desired combination of size and distribution patterns.

FIG. 26 is a top schematic view of at least a portion of a device 104 for delivering light energy to living skin tissue, wherein the device 104 is edge lit along multiple edges with multiple light-emitting sources 36 supported by the substrate 38 or flexible PCB. The substrate 38 is preferably encapsulated on one or both sides with an encapsulating material. Multiple holes or perforations 66 of substantially uniform size and substantially uniform distribution across the substrate 38 are defined through the substrate 38 and any associated encapsulating material layers. The substrate 38 preferably includes a reflective material arranged to reflect light toward the light-transmissive outer surface 42 of the device 104. In certain embodiments, one or more light-emitting sources 36 may be provided to produce one or both of collagen-promoting light and ES increasing and/or ES releasing light.

FIG. 27 is a top schematic view of at least a portion of a device 106 for delivering light energy to living skin tissue, wherein the device 106 is edge lit along multiple edges with multiple light-emitting sources 36 supported by the substrate 38 or flexible PCB. The substrate 38 is preferably encapsulated on one or both sides with an encapsulating material as previously described. Multiple holes or perforations 66-1, 66-2 of differing sizes, but with a substantially uniform distribution across the substrate 38, are defined through the substrate 38 and any associated encapsulating material layers. The substrate 38 preferably includes a reflective material arranged to reflect light toward the light-transmissive outer surface 42 of the device 106. In certain embodiments, one or more light-emitting sources 36 may be provided to produce one or both of collagen-promoting light and ES increasing and/or ES releasing light.

FIG. 28 is a top schematic view of at least a portion of a device 108 for delivering light energy to living skin tissue, wherein the device 108 is edge lit along multiple edges with multiple light-emitting sources 36 supported by the substrate 38 or flexible PCB. The substrate 38 is preferably encapsulated on one or both sides with an encapsulating material. The substrate 38 preferably includes a reflective material arranged to reflect light toward the light-transmissive outer surface 42 of the device 108. Multiple holes or perforations 66-1, 66-2 of different sizes are provided in one or more clusters 66A (e.g., proximate to one or more light-emitting sources 36) and defined through the substrate 38 and any associated encapsulating material layers. In certain embodiments, one or more light-emitting sources 36 may be provided to produce one or both of collagen-promoting light and ES increasing and/or ES releasing light.

FIG. 29 is a top schematic view of at least a portion of a device 110 for delivering light energy to living skin tissue, wherein the device 110 is edge lit along multiple edges with multiple light-emitting sources 36 supported by the substrate 38 or flexible PCB. The substrate 38 is preferably encapsulated on one or both sides with an encapsulating material. The substrate 38 preferably includes a reflective material arranged to reflect light toward the light-transmissive outer surface 42 of the device 110. Multiple holes or perforations 66-1, 66-2 of different sizes and with a non-uniform (e.g., random) distribution are defined through the substrate 38 and any associated encapsulating material layers. In certain embodiments, one or more light-emitting sources 36 may be provided to produce one or both of collagen-promoting light and ES increasing and/or ES releasing light.

FIG. 30A is a top schematic view of at least a portion of a light-emitting device 112 for delivering light energy to living skin tissue and at least a portion of a battery/control module 114, wherein an elongated electrical cable 116 is associated with the battery/control module 114 for connecting the battery/control module 114 to the light-emitting device 112. The light-emitting device 112 is edge lit along one edge with a light-emitting region 118 supported by the substrate 38 or flexible PCB. The substrate 38 is preferably encapsulated on one or both sides with an encapsulating material. The substrate 38 preferably includes a reflective material arranged to reflect light toward the light-transmissive outer surface 42 of the device 112. Multiple holes or perforations 66 are defined through the substrate 38 and any associated encapsulating material layers. One or more sensors 120 (e.g., temperature sensors or any other types of sensors disclosed herein) may be arranged in or on the substrate 38. A socket 122 associated with the light-emitting device 112 is arranged to receive a plug 124 to which the electrical cable 116 from the battery/control module 114 is attached. The battery/control module 114 may include a body 126, a battery 128, and a control board 130, which may include an emitter driver circuit and/or any suitable control, sensing, interface, data storage, and/or communication components as disclosed herein. The battery/control module 114 may further include a port or other interface 132 to enable communication with an external device (e.g., laptop or tablet computer, a mobile phone, or another portable digital device) via wired or wireless means.

FIG. 30B is a top schematic view of at least a portion of a light-emitting device 134 for delivering light energy to living skin tissue and at least a portion of a battery/control module 136, wherein an elongated electrical cable 138 is associated with the light-emitting device 134 for connecting the light-emitting device 134 to the battery/control module 136. The light-emitting device 134 is edge lit along one edge with the light-emitting region 118 supported by the substrate 38 or flexible PCB. The substrate 38 is preferably encapsulated on one or both sides with an encapsulating material. The substrate 38 preferably includes a reflective material arranged to reflect light toward the light-transmissive outer surface 42 of the device 134. Multiple holes or perforations 66 may be defined through the substrate 38 and any associated encapsulating material layers. One or more sensors 120 (e.g., temperature sensors or any other types of sensors disclosed herein) may be arranged in or on the substrate 38. A socket 140 associated with the battery/control module 136 is arranged to receive a plug 142 to which the electrical cable 138 from the light-emitting device 134 is attached. The battery/control module 136 may include the body 126, the battery 128, and the control board 130, which may include an emitter driver circuit and/or any suitable control, sensing, interface, data storage, and/or communication components as disclosed herein. The light-emitting device 134 may further include a port or other interface 144 to enable communication with an external device (e.g., laptop or tablet computer, a mobile phone, or another portable digital device) via wired or wireless (e.g., via a transceiver, or via a transmitter and/or a transceiver) means.

FIG. 31 is a top schematic view of at least a portion of a light-emitting device 146 for delivering light energy to living skin tissue and being connected via an electrical cord 148 to a battery/control module 150, wherein the light-emitting device 146 includes multiple light sources 36 supported by the substrate 38 or flexible PCB, multiple holes or perforations 66, and multiple sensors 120A-120C. The substrate 38 is preferably encapsulated on one or both sides with an encapsulating material. The substrate 38 preferably includes a reflective material arranged to reflect light toward the light-transmissive outer surface 42 of the device 146. The multiple holes or perforations 66 are defined through the substrate 38 and any associated encapsulating material layers. The sensors 120A-120C are arranged in or on the substrate 38. In certain embodiments, the sensors 120A-120C may differ in type from one another. In certain embodiments, the sensors 120A-120C may include one or more light emitters and photodiodes to illuminate a wound site with one or more selected wavelengths to detect blood flow in or proximate to a wound site to provide photoplethysmography data. The sensors 120A-120C may alternatively or additionally be arranged to detect blood pressure, bandage or dressing covering pressure, heart rate, temperature, presence or concentration of chemical or biological species (e.g., in wound exudate), or other conditions. A socket 152 associated with the light-emitting device 146 is arranged to receive a plug 154 to which the electrical cord 148 from the battery/control module 150 is attached. The battery/control module 150 may include the body 126, the battery 128, and the control board 130, which may include an emitter driver circuit and/or any suitable control, sensing, interface, data storage, and/or communication components as disclosed herein. The battery/control module 150 may further include a port or other interface 156 to enable communication with an external device (e.g., laptop or tablet computer, a mobile phone, or another portable digital device) via wired or wireless means.

FIGS. 32A-32C illustrate different light pulse profiles that may be used with devices and methods according to the present disclosure. FIG. 32A is a plot of light intensity versus time embodying a first exemplary illumination cycle that may be used with at least one emitter of a light-emitting device for delivering light energy to living skin tissue as disclosed herein. As shown in FIG. 32A, a series of discrete pulses of substantially equal intensity and duration may be provided during at least one time window or a portion thereof. FIG. 32B is a plot of light intensity versus time embodying a second exemplary illumination cycle that may be used with at least one emitter of a light-emitting device disclosed herein. As shown in FIG. 32B, intensity may be reduced from a maximum (or high) value to a reduced but non-zero value during at least one time window. FIG. 32C is a plot of light intensity versus time embodying a third exemplary illumination cycle that may be used with at least one emitter of a light-emitting device disclosed herein. As shown in FIG. 32C, intensity may be steadily reduced from a maximum (or high) value to sequentially reduced values over time. Other pulse profiles may be used according to certain embodiments.

FIG. 33 is a schematic plan view of the LED PCB assembly 22 of FIGS. 1 and 2 for the mask 10 for treating living skin tissue according to the present disclosure. Referring to FIG. 33, the LED PCB assembly 22 includes the substrate 38 (e.g., a flexible PCB) that may be configured for placement of one or more first light sources 36-1 and one or more second light sources 36-2. In certain embodiments, the one or more first light sources 36-1 may embody infrared LEDs that emit light of wavelength in the range of from about 840 nm to about 860 nm. The one or more second light sources 36-2 may embody red LEDs that emit light of a wavelength in a range of from about 610 nm to about 630 nm. As illustrated, the substrate 38 may include one or more notches 158, a tab 160 and a slot 162 to enable the substrate 38 to be flexed into a face-conforming shape and retained in that shape. As illustrated, the substrate 38 may also include the eye opening 32B as previously described.

FIG. 34A is a schematic plan view of the LED PCB assembly 22 of FIG. 33 that only shows placement of the one or more first light sources 36-1. FIG. 34B is a schematic plan view of the LED PCB assembly 22 of FIG. 33 that only shows placement of the one or more second light sources 36-2. As illustrated in FIGS. 33, 34A, and 34B, the first and second light sources 36-1, 36-2 may be non-uniformly arranged across the substrate 38. In this regard, a density of the first and second light sources 36-1, 36-2 may be varied such that higher densities of the first and/or second light sources 36-1, 36-2 may be provided in areas that correspond with target areas of a user's face that may have larger amounts of wrinkles. Such target areas may include the forehead, around the eyes, along portions of the cheeks near the mouth, adjacent the lips, and even towards the neck of the user.

FIG. 35 is a schematic diagram showing interconnections between components of a light-emitting device for delivering light energy to skin tissue of a patient according to one embodiment. A microcontroller 502 is arranged to receive power from a battery 522 (nominally 3.7 V) via a 5V voltage boost circuit 512. The microcontroller 502 may be arranged to control a charging integrated circuit 514 arranged between a microUSB connector 516 and the battery 522, wherein the microUSB connector 516 may be used to receive current for charging the battery 522. In certain embodiments, the microUSB connector 516 may also be used for communicating data and/or instructions to or from the microcontroller 502 and/or an associated memory. The microcontroller 502 is also arranged to control a 12V boost circuit 518 for increasing voltage to one or more LED arrays 520. The microcontroller 502 further controls one or more LED driver circuits 510 arranged to drive the LED array(s) 520. The microcontroller 502 is also arranged to receive inputs from a user input button 504, a temperature sensor 524, and a proximity sensor 526 (which includes an infrared LED 528). The microcontroller 502 is further arranged to provide output signals to a LCD display 506 and a buzzer 508. Certain components are located off-board relative to a controller PCB, as indicated by the vertical dashed line in FIG. 35. In operation of the light-emitting device, a user may depress the button 504 to start operation. If the proximity sensor 526 detects that the device has been placed in suitable proximity to desired skin tissue, then the microcontroller 502 may trigger the LED driver circuit(s) 510 to energize the LED array(s) 520. Temperature during operation is monitored with the temperature sensor 524. If an excess temperature condition is detected, then the microcontroller 502 may take appropriate action to reduce current supplied by the LED driver circuit(s) 510 to the LED array(s) 520. Operation may continue until a timer (e.g., internal to the microcontroller 502) causes operation to terminate automatically. One or more indicator LEDs (not shown) may provide a visible signal indicative of charging status of the battery 522. Audible signals for commencement and termination of operation may be provided by the buzzer 508 or a suitable speaker. Information relating to usage cycles, usage time, or any other suitable parameter may be displayed by the LCD display 506.

FIG. 36 is a schematic diagram depicting an interface between hardware drivers, functional components, and a software application suitable for operating a light-emitting device according to FIG. 35. Application executive functions 503, including timers and counters 507, may be performed with one or more integrated circuits (such as the microcontroller 502 illustrated in FIG. 35). Hardware drivers 505 may be used to interface with various input and output elements, such as the LED array(s) 520, the speaker or buzzer 508, the LCD display 506, the temperature sensor 524, the push button 504, indicator LEDs 509, and the proximity sensor 526.

FIG. 37 is an exploded view of a light-emitting device 405 embodied in a wearable cap for delivering light energy to a scalp of a patient. The device 405 includes multiple light emitters and standoffs supported by a flexible PCB 410 including multiple interconnected panels 412A-412F arranged in a concave configuration. A concave shaping member 430 (including a frame 431, ribs 432A-432D, and curved panels 434A-434D) is configured to receive the flexible PCB 410. The ribs 432A-432D and curved panels 434A-434D project generally outwardly and downwardly from the frame 431. Gaps are provided between portions of adjacent ribs 432A-432D and curved panels 434A-434D to accommodate outward expansion and inward contraction, and to enable transfer of heat and/or fluid (e.g., evaporation of sweat). A fabric covering element 460 is configured to cover the concave shaping member 430 and the flexible PCB 410 contained therein. A battery 450 and a battery holder 451 are arranged between the flexible PCB 410 and the concave shaping member 430. An electronics housing 440 is arranged to be received within an opening 431A defined in the frame 431 of the concave shaping member 430. Pivotal coupling elements 441A, 451A are arranged to pivotally couple the battery holder 451 to the electronics housing 440. An electronics board 441 is insertable into the electronics housing 440, which is enclosed with a cover 442. Arranged on the electronics board 441 are a cycle counter 443, a control button 444, a charging/data port 445, and a status lamp 446. The various elements associated with the electronics housing 440 and the electronics board 441 may be referred to generally as a "control module." Windows 442A defined in the cover 442 provide access to the cycle counter 443, the control button 444, the charging/data port 445, and the status lamp 446. The fabric covering element 460 includes a fabric body 461 and multiple internal pockets 462A-462D arranged to receive portions of the ribs 432A-432D. An opening 468 at the top of the fabric covering element 460 is arranged to receive the cover 442.

FIG. 38 is a bottom plan view of the flexible PCB 410 including light emitters 420 and standoffs 425 arranged thereon. The PCB 410 includes a polyimide substrate 411, an inner surface 411A, and an outer surface 411B. In one embodiment, the light emitters 420 include a total of 280 LEDs arranged as 56 strings of 5 LEDs, with a string voltage of 11 V, a current limit of 5 mA, and a power consumption of 3.08 watts. FIG. 38 illustrates 36 standoffs 425 extending from the inner surface 411A of the PCB 410. The flexible PCB 410 includes six interconnected panels 412A-412F, with the panels 412A-412F being connected to one another via narrowed tab regions 413B-413F. Gaps 414A-414F are provided between various panels 412A-412F, with such gaps 414A-414F (which are extended proximate to the narrowed tab regions 413B-413F) being useful to permit transport of heat and/or fluid (e.g., evaporation of sweat) between the panels 412A-412F. As shown in FIG. 38, holes 415A, 415B are defined through the substrate 411 to receive fasteners (not shown) for joining the PCB 410 to corresponding holes 440A, 440B defined in the electronics housing 440. A further opening 415C may be provided for sensor communication between a proximity sensor (e.g., photosensor) and the interior of the PCB 410 when the PCB 410 is shaped into in a concave configuration.

FIG. 39 schematically depicts a region of a lens 390 (e.g., a lens that can be used as the lens in FIGS. 1 and 2) that comprises a plurality of light scattering regions 391 that are arranged in a similar manner as described for FIG. 23B.

FIG. 40 schematically depicts a region of a lens 392 (e.g., a lens that can be used as the lens in FIGS. 1 and 2) that comprises a lenticular lens region 393. In certain embodiments, the lenticular lens region 393 may be injection molded together with the remainder of the lens 392. In certain embodiments, the lenticular lens region 393 may form the outermost surface of the lens 392, while in other embodiments, a first surface 392' of the lens 392 may cover the lenticular lens region 393. In such embodiments, the lenticular lens region 393 may thereby be formed between the first surface 392' and an opposing second surface 392".

FIG. 41 schematically depicts a face-engaging device 610 that comprises a mask 611 (which can comprise any of, or any combination of, a lens, a flexible PCB, a housing and a fabric mask placeholder as described for FIGS. 1 and 2) and an elastic headband (or strap) 612 (elongated to show the direction in which it extends) attached to the mask 611 by headband engagement features in the form of stitching 613 (only visible on the near side).

FIG. 42 schematically depicts a face-engaging device 620 that comprises a mask 621 and an elastic headband (or strap) 622 (elongated, as in FIG. 41), and that is similar to the face-engaging device 610 shown in FIG. 41. In FIG. 42, a first imaginary line 623 is shown that bisects the headband 622 along a portion of the headband 622 extending away from an eye hole 624 of the mask 621, and a second imaginary line 625 is shown that bisects a region of the device 620 that conforms to a forehead of a human user. In certain embodiments, the second imaginary line 625 is arranged in a parallel manner with portions of the mask 621 (e.g., the housing and/or light-transmissive element) that are configured to contact the user's forehead. The first and second imaginary lines 623, 625 intersect and form an angle A° that is non-perpendicular, such in a range from about 45 degrees to about 75 degrees, or in a range from about 50 degrees to about 70 degrees, or in a range from about 55 degrees to about 65 degrees, or in a range from about 58 degrees to about 62 degrees, or about 60 degrees. By arranging the headband 622 with this orientation, the mask 621 may primarily interact with the user's forehead, which corresponds with the largest surface area of the user's face. Specifically, the forehead may correspond with the largest surface area of bone that is associated with the user's face. In this regard, the mask 621 may primarily contact the user's forehead, thereby relieving pressure around the eyes and nose bridge, among other areas of the user's face. Additionally, having the headband 622 provide such an angle A° may facilitate a user easily and rapidly removing the mask, e.g., in the event a user gets overheated and/or claustrophobic, or if another person enters the room and the user does not want to be seen wearing the mask 621. In certain aspects, the mask 621 may be rapidly deactivated concurrently with mask removal by way of the previously described proximity sensor. The ease and rapidity with which a mask 621 can be removed and deactivated can, in some embodiments, be enhanced where a high percentage of force being exerted by the headband 622 and pushing the device toward the user's face is applied against a combination of (1) the human user's forehead and (2) areas of the human user's face that one or more eyepieces of the mask 621 contact, as described elsewhere herein in connection with other features. In addition, with such features, greater airflow can occur between the mask 621 and the user's face, enhancing comfort (e.g., reducing the temperature of the user's face and/or of the mask 621).

FIG. 43 schematically depicts a face-engaging device 630 that comprises a mask 631 (which can comprise any of, or any combination of, a lens, a flexible PCB, a housing and a fabric mask placeholder as described for FIGS. 1 and 2), a headband (or strap) 632, and first and second headband engagement features 633 (only one of which is visible in FIG. 43), such as a strap and a strap holder that allow adjustment of the mask 631 according to a size of a user's head.

FIG. 44 schematically depicts a face-engaging device 640 that comprises a mask 641 (which can comprise any of, or any combination of, a lens, a flexible PCB, a housing and a fabric mask placeholder as described for FIGS. 1 and 2), a headband (or strap) 642, and first and second headband engagement features in the form of snaps 643 (only one of which is visible in FIG. 44). The snaps 643 may represent a series of snaps that allow adjustment of the mask 631 according to a size of a user's head.

Described above are a wide range of means for impinging light having a first peak wavelength on skin tissue at a first radiant flux, wherein the first peak wavelength is selected to either stimulate enzymatic generation of nitric oxide to increase endogenous stores of nitric oxide or release nitric oxide from the endogenous stores. For example, as described above, any light emitter that emits at least some light of wavelength within the ranges described herein for stimulating enzymatic generation of nitric oxide to increase endogenous stores of nitric oxide and/or releasing nitric oxide from the endogenous stores is such a means. As noted above, persons of skill in the art are familiar with a wide variety of light emitters (e.g., LEDs, laser diodes and other solid state light emitters) that emit light at any of such wavelengths, and any of such light emitters are such means.

Described above are a wide range of means for impinging light having a second peak wavelength on skin tissue at a second radiant flux to increase collagen production in said skin. For example, as described above, any light emitter that emits at least some light of wavelength within the ranges described herein for increase collagen production in skin is such a means. As noted above, persons of skill in the art are familiar with a wide variety of light emitters (e.g., LEDs, laser diodes and other solid state light emitters) that emit light at any of such wavelengths, and any of such light emitters are such means.

Described above are a wide range of means for impinging light having a third peak wavelength on skin tissue, wherein the third peak wavelength differs from the first peak wavelength by at least 30 nm, and wherein the light having a third wavelength provides an anti-inflammatory effect to the skin. For example, as described above, any light emitter that emits at least some light of wavelength within the ranges described herein for providing an anti-inflammatory effect to skin is such a means. As noted above, persons of skill in the art are familiar with a wide variety of light emitters (e.g., LEDs, laser diodes and other solid state light emitters) that emit light at any of such wavelengths, and any of such light emitters are such means.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A device for treating living skin tissue, the device comprising:
   a housing;
   a light-transmissive element;
   a flexible printed circuit board arranged between the housing and the light-transmissive element;
   a plurality of first light-emitting diodes (LEDs) and a plurality of second LEDs that are both mounted on the flexible printed circuit board in an arrangement to provide light through the light-transmissive element to impinge the light on skin tissue; and
   an eyepiece arranged to extend through the flexible printed circuit board and past the light-transmissive element from a side of the light-transmissive element that is opposite the housing, wherein the eyepiece is removable from the housing such that a standoff distance between the light-transmissive element and the skin tissue is adjustable;
   wherein the plurality of first LEDs are configured to emit light of a first peak wavelength that is selected to at least one of stimulate nitric oxide production in the skin tissue and release endogenous stores of nitric oxide in the skin tissue, and the plurality of second LEDs are configured to emit light of a second peak wavelength that stimulates collagen production.

2. The device of claim 1, wherein the housing, the light-transmissive element, and the flexible printed circuit board form an eye opening that extends through the housing, the light-transmissive element, and the flexible printed circuit board.

3. The device of claim 2, wherein the eyepiece resides within the eye opening.

4. The device of claim 3, wherein a portion of the eyepiece extends beyond the light-transmissive element and is configured to engage a user's eye sockets during use.

5. The device of claim 2, further comprising a covering element that is arranged to cover one or more portions of the housing, wherein the eye opening extends through the covering element, and wherein the housing forms a plurality of recesses that are arranged to receive one or more portions of the covering element.

6. The device of claim 2, further comprising a headband that is configured to secure the housing, the light-transmissive element, and the flexible printed circuit board along a forehead of a user.

7. The device of claim 6, wherein the headband is provided at an angle that is non-perpendicular with portions of the light-transmissive element that are parallel with the forehead of the user.

8. The device of claim 7, wherein the angle is in a range from 45 degrees to 75 degrees.

9. The device of claim 7, wherein the angle is in a range from 55 degrees to 65 degrees.

10. The device of claim 1, wherein the first peak wavelength is in a range of from 610 nm to 630 nm and the second peak wavelength is in a range from 840 nm to 860 nm.

11. The device of claim 1, wherein the plurality of first LEDs and the plurality of second LEDs are non-uniformly arranged on the flexible printed circuit board.

12. The device of claim 1, wherein the housing, the light-transmissive element, and the flexible printed circuit board form a mask for delivering light to a face of a user, and a portion of the mask is configured to extend below a chin of the user for delivering the light of the first peak wavelength and the light of the second peak wavelength to a neck of the user.

13. The device of claim 1, further comprising a plurality of third LEDs mounted on the flexible printed circuit board in an arrangement to provide light through the light-transmissive element to impinge the light on the skin tissue.

14. The device of claim 13, wherein the plurality of third LEDs are configured to emit light having a third peak wavelength that is in a range from 640 nm to 660 nm.

15. The device of claim 1, wherein the light-transmissive element comprises a lenticular lens structure.

* * * * *